(12) United States Patent
Diwu et al.

(10) Patent No.: US 9,896,538 B2
(45) Date of Patent: Feb. 20, 2018

(54) POLYFLUORENO[4,5-CDE]OXEPINE POLYMERS AND CONJUGATES THEREOF

(71) Applicants: AAT Bioquest, Inc., Sunnyvale, CA (US); Affymetrix, Inc., Santa Clara, CA (US)

(72) Inventors: Zhenjun Diwu, Sunnyvale, CA (US); Haitao Guo, Sunnyvale, CA (US); Ruogu Peng, San Jose, CA (US); Qin Zhao, Sunnyvale, CA (US); Travis Jennings, Poway, CA (US); Castle Funatake, San Diego, CA (US)

(73) Assignees: AAT Bioquest, Inc., Sunnyvale, CA (US); Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 15/469,952

(22) Filed: Mar. 27, 2017

(65) Prior Publication Data

US 2017/0275418 A1    Sep. 28, 2017

Related U.S. Application Data

(60) Provisional application No. 62/376,941, filed on Aug. 19, 2016, provisional application No. 62/313,977, filed on Mar. 28, 2016.

(51) Int. Cl.
| | | |
|---|---|---|
| G01N 33/533 | (2006.01) | |
| C09K 11/06 | (2006.01) | |
| C08G 61/12 | (2006.01) | |

(52) U.S. Cl.
CPC ............ *C08G 61/128* (2013.01); *C09K 11/06* (2013.01); *G01N 33/533* (2013.01); *C08G 2261/12* (2013.01); *C08G 2261/143* (2013.01); *C08G 2261/1424* (2013.01);
(Continued)

(58) Field of Classification Search
CPC .............. C08G 61/128; C08G 2261/12; C08G 2261/1424; C08G 2261/143; C08G 2261/3142; C08G 2261/3242; C09K 11/06; C09K 2211/1416; C09K 2211/145; G01N 33/533; C07C 2603/18
See application file for complete search history.

(56) References Cited

U.S. PATENT DOCUMENTS

| | | |
|---|---|---|
| 6,353,072 B1 | 3/2002 | Towns et al. |
| 7,144,950 B2 | 12/2006 | Bazan et al. |
| 7,214,489 B2 | 5/2007 | Bazan et al. |

(Continued)

FOREIGN PATENT DOCUMENTS

| | | |
|---|---|---|
| CN | 1683429 A | 10/2005 |
| CN | 101323781 A | 12/2008 |

(Continued)

OTHER PUBLICATIONS

Lim et al. Suppression of Green Emission in a new class of blue-emitting polyfluorene copolymers with twisted biphenyl moieties. Adv. Funct. Mater. 2005, vol. 15, pp. 981-988.*

(Continued)

*Primary Examiner* — Shafiqul Haq
(74) *Attorney, Agent, or Firm* — Banner & Witcoff, Ltd.

(57) ABSTRACT

The invention provides for polyfluoreno[4,5-cde]oxepine conjugates and their use in methods of analyte detection.

26 Claims, 8 Drawing Sheets

(52) U.S. Cl.
CPC ............... *C08G 2261/3142* (2013.01); *C08G 2261/3242* (2013.01); *C09K 2211/145* (2013.01); *C09K 2211/1416* (2013.01)

(56) References Cited

U.S. PATENT DOCUMENTS

| | | | |
|---|---|---|---|
| 7,270,956 | B2 | 9/2007 | Bazan et al. |
| 7,666,594 | B2 | 2/2010 | Bazan et al. |
| 7,811,755 | B2 | 10/2010 | Bazan et al. |
| 7,897,684 | B2 | 3/2011 | Bazan et al. |
| 8,110,673 | B2 | 2/2012 | Bazan et al. |
| 8,158,444 | B2 | 4/2012 | Gaylord et al. |
| 8,227,187 | B2 | 7/2012 | Bazan et al. |
| 8,309,672 | B2 | 11/2012 | Bazan et al. |
| 8,362,193 | B2 | 1/2013 | Gaylord et al. |
| 8,598,306 | B2 | 12/2013 | McKiernan et al. |
| 8,835,113 | B2 | 9/2014 | Bazan et al. |
| 8,841,072 | B2 | 9/2014 | Bazan et al. |
| 8,969,509 | B2 | 3/2015 | Liu et al. |
| 8,993,335 | B2 | 3/2015 | Bazan et al. |
| 9,017,766 | B2 | 4/2015 | Bazan et al. |
| 9,085,799 | B2 | 7/2015 | Bazan et al. |
| 2006/0142522 | A1 | 6/2006 | Liu |
| 2011/0257374 | A1 | 10/2011 | Gaylord et al. |
| 2012/0029155 | A1 | 2/2012 | Gaylord et al. |
| 2014/0350183 | A1 | 11/2014 | Chiu et al. |
| 2015/0226746 | A1 | 8/2015 | Bazan et al. |
| 2016/0169917 | A1 | 6/2016 | Syamakumari et al. |
| 2016/0341720 | A1 | 11/2016 | Bazan et al. |
| 2017/0184571 | A1 | 6/2017 | Bazan et al. |

FOREIGN PATENT DOCUMENTS

| | | |
|---|---|---|
| CN | 101240329 B | 6/2010 |
| CN | 101864042 B | 10/2012 |
| CN | 102020760 B | 10/2012 |
| CN | 102964767 A | 3/2013 |
| CN | 103408728 A | 11/2013 |
| CN | 103588960 A | 2/2014 |
| CN | 103665329 A | 3/2014 |
| CN | 104031477 A | 9/2014 |
| CN | 104532396 A | 4/2015 |
| CN | 104561247 A | 4/2015 |
| CN | 105295007 A | 2/2016 |
| CN | 105330825 A | 2/2016 |
| KR | 20110122316 A | 11/2011 |
| WO | 99/57222 A1 | 11/1999 |
| WO | 01/71317 A1 | 9/2001 |
| WO | 2013/101902 A2 | 7/2013 |

OTHER PUBLICATIONS

Cho, Nam Sung, et al.,"Synthesis, characterization, and electroluminescence of new conjugated polyfluorene derivatives containing various dyes as comonomers," Macromolecules, v 37, n 14, p. 5265-5273, Jul. 13, 2004; ISSN: 00249297; DOI: 10.1021/ma049728g; Publisher: American Chemical Society.

Gaylord, Brent S., "Light emitting conjugated polymers for use in biological detection platforms," University of California, Santa Barbara, ProQuest Dissertations Publishing, 2004. 3159298, 252 pg; ISBN 9780496923403, 0496923404; DAI-B 65/12, Dissertation Abstracts International; ProQuest document ID 305201216.

Gaylord, Brent S., et al.,"DNA hybridization detection with water-soluble conjugated polymers and chromophore-abeled single-stranded DNA," Journal of the American Chemical Society, v 125, n 4, p. 896-900, Jan. 29, 2003; ISSN: 00027863; DOI: 10.1021/ja027152+; Publisher: American Chemical Society.

Hollingsworth, William R., et al.,"Exciton Transfer and Emergent Excitonic States in Oppositely-Charged Conjugated Polyelectrolyte Complexes," Journal of Physical Chemistry B (2016), 120(31), 7767-7774; PB American Chemical Society.

Jia, Yongmei, et al.,"Facile Probe Design: Fluorescent Amphiphilic Nucleic Acid Probes without Quencher Providing Telomerase Activity Imaging Inside Living Cells," Anal. Chem., May 25, 2016, 88 (12), pp. 6621-6626.

Liu, Bin, et al.,"Shape-Adaptable Water-Soluble Conjugated Polymers," J. Am. Chem. Soc., Oct. 10, 2003, 125 (44), pp. 13306-13307; DOI: 10.1021/ja0365072; Publisher: American Chemical Society.

Liu, Bin, et al.,"Effect of Chromophore-Charge Distance on the Energy Transfer Properties of Water-Soluble Conjugated Oligomers," J. Am. Chem. Soc., 2003, 125 (22), pp. 6705-6714; DOI: 10.1021/ja028961w; Publisher: American Chemical Society.

Luo, Wenjuan, et al.,"Nanoprecipitation of Fluorescent Conjugated Polymer onto the Surface of Plasmonic Nanoparticle for Fluorescence/Dark-Field Dual-Modality Single Particle Imaging," Analytical Chemistry (Washington, DC, United States) (2016), 88(13), 6827-6835; PB: American Chemical Society.

Pu, Kan-Yi, et al.,"A Multicolor Cationic Conjugated Polymer for Naked-Eye Detection and Quantification of Heparin," Macromolecules, Aug. 28, 2008, 41 (18), pp. 6636-6640; DOI: 10.1021/ma801269n; Publisher: American Chemical Society.

Pu, Kan-Yi, et al.,"Optimizing the cationic conjugated polymer-sensitized fluorescent signal of dye labeled oligonucleotide for biosensor applications," Biosensors and Bioelectronics, v 24, n 5, p. 1067-1073, Jan. 1, 2009; Publisher: Elsevier Ltd.

Pu, Kan-Yi, et al.,"Optimization of Interactions between a Cationic Conjugated Polymer and Chromophore-Labeled DNA for Optical Amplification of Fluorescent Sensors," J. Phys. Chem. B, Jul. 16, 2008, 112 (31), pp. 9295-9300; DOI: 10.1021/jp8019717; Publisher: American Chemical Society.

Ren, Yan, et al.,"Trifluoromethyl-substituted conjugated oligoelectrolytes," Chemistry—A European Journal, v 16, n 36, p. 11028-11036, Sep. 24, 2010; Publisher: Wiley-VCH Verlag.

Wang, S., et al.,"Size-specific interactions between single- and double-stranded oligonucleotides and cationic water-soluble oligofluorenes," Advanced Functional Materials13.6 (Jun. 2003): 463-467; ISSN 1616-301X; ProQuest document ID 27998371; Publisher: Wiley.

Woo, H. Y., et al.,"Cationic Conjugated Polyelectrolytes with Molecular Spacers for Efficient Fluorescence Energy Transfer to Dye-Labeled DNA," Advanced Functional Materials17.2(Jan. 2007): 290-295; Publisher: Wiley.

Bout, David A. Vanden, et al.,"Discrete Intensity Jumps and Intramolecular Electronic Energy Transfer in the Spectroscopy of Single Conjugated Polymer Molecules," Science, vol. 277, Aug. 22, 1997, pp. 1074-1077.

Chen, Liaohai, et al.,"Highly sensitive biological and chemical sensors based on reversible fluorescence quenching in a conjugated polymer," PNAS, Oct. 26, 1999, vol. 96, No. 22, pp. 12287-12292.

Gaylord, Brent S., et al.,"Water-Soluble Conjugated Oligomers: Effect of Chain Length and Aggregation on Photoluminescence-Quenching Efficiencies," J. Am. Chem. Soc. 2001, 123, 6417-6418.

McQuade, D. Tyler, et al., "Conjugated Polymer-Based Chemical Sensors," Chem. Rev., 2000, 2537-2574.

McQuade, D. Tyler, et al., "Signal Amplification of a "Turn-On" Sensor:? Harvesting the Light Captured by a Conjugated Polymer," J. Am. Chem. Soc., 2000, 122 (49), pp. 12389-12390.

Mishra, Amaresh, et al., "Cyanines during the 1990s:? A Review," Chem. Rev., 2000, 100 (6), pp. 1973-2012.

Nikiforov, Theo T., et al.,"Detection of Hybrid Formation between Peptide Nucleic Acids and DNA by Fluorescence Polarization in the Presence of Polylysine," Analytical Biochemistry 275, 248-253 (1999).

Peng Kang-Yung, et al.,"Efficient Light Harvesting by Sequential Energy Transfer across Aggregates in Polymers of Finite Conjugational Segments with Short Aliphatic Linkages," J. Am. Chem. Soc. 2001, 123, 11388-11397.

Svanvik, Nicke, et al.,"Light-Up Probes: Thiazole Orange-Conjugated Peptide Nucleic Acid for Detection of Target Nucleic Acid in Homogeneous Solution," Analytical Biochemistry 281, 26-35 (2000).

(56) References Cited

OTHER PUBLICATIONS

Swager, Timothy M., et al.,"Fluorescence Studies of Poly(p-phenyleneethynylene)s: The Effect of Anthracene Substitution," J. Phys. Chem. 1995, 99, 4886-4893.
Thomas III, Samuel W., et al.,"Chemical Sensors Based on Amplifying Fluorescent Conjugated Polymers," Chem. Rev., 2007, 107 (4), pp. 1339-1386.
Wang, Deli, et al.,"Photoluminescence quenching of water-soluble conjugated macromolecule by bipyridinium derivatives," Synthetic Metals, 119 (2001), pp. 587-588.
Zhu, Chenlei, et al.,"Water-Soluble Conjugated Polymers for Imaging, Diagnosis, and Therapy," Chem. Rev., 2012, 112 (8), pp. 4687-4735.
Zu, Xu-Hui, et al.,"Solution-processable single-material molecular emitters for organic light-emitting devices," Chem. Soc. Rev., 2011,40, 3509-3524.

\* cited by examiner

POLYFLUORENO[4,5-CDE]OXEPINE POLYMERS AND CONJUGATES THEREOF

RELATED APPLICATION DATA

The present application claims priority from U.S. Provisional Patent Application No. 62/376,941, filed Aug. 19, 2016 and U.S. Provisional Patent Application No. 62/313,977, filed Mar. 28, 2016 each of which is hereby incorporated by reference in their entireties.

FIELD

The invention relates in general to fluorescent polymer conjugates and their use in methods of analyte detection.

BACKGROUND

Fluorescent probes are valuable reagents for the analysis and separation of molecules and cells and for the detection and quantification of other materials. A very small number of fluorescent molecules can be detected under optimal circumstances. Barak and Webb visualized fewer than 50 fluorescent lipid analogs associated with the LDL reception of cells using a SIT camera, J. CELL BIOL., 90, 595-604 (1981). Flow cytometry can be used to detect fewer than 10,000 fluorescein molecules associated with particles or certain cells (Muirhead, Horan and Poste, BIOTECHNOLOGY, 3, 337-356 (1985)). Some specific examples of the application of fluorescent probes are (1) identification and separation of subpopulations of cells in a mixture of cells by the techniques of fluorescence flow cytometry, fluorescence-activated cell sorting and fluorescence microscopy; (2) determination of the concentration of a substance that binds to a second species (e.g., antigen-antibody reactions) in the technique of fluorescence immunoassay; (3) localization of substances in gels and other insoluble supports by the techniques of fluorescence staining. These techniques are described by Herzenberg, et al., "CELLULAR IMMUNOLOGY" 3rd ed., Chapter 22; Blackwell Scientific Publications (1978); and by Goldman, "FLUORESCENCE ANTIBODY METHODS", Academic Press, New York, (1968); and by Taylor, et al., APPLICATIONS OF FLUORESCENCE IN THE BIOMEDICAL SCIENCES, Alan Liss Inc., (1986).

When employing fluorescent polymers for the above purposes, there are many constraints on the choice of the fluorescent polymer. One constraint is the absorption and emission characteristics of the fluorescent polymer, since many ligands, receptors, and materials in the sample under test, e.g. blood, urine, cerebrospinal fluid, will fluoresce and interfere with an accurate determination of the fluorescence of the fluorescent label. This phenomenon is called autofluorescence or background fluorescence. Another consideration is the ability to conjugate the fluorescent polymer to ligands and receptors and other biological and non-biological materials and the effect of such conjugation on the fluorescent polymer. In many situations, conjugation to another molecule may result in a substantial change in the fluorescent characteristics of the fluorescent polymer and, in some cases, substantially destroy or reduce the quantum efficiency of the fluorescent polymer. It is also possible that conjugation with the fluorescent polymer will inactivate the function of the molecule that is labeled. A third consideration is the quantum efficiency of the fluorescent polymers which should be high for sensitive detection. A fourth consideration is the light absorbing capability, or extinction coefficient, of the fluorescent polymers, which should also be as large as possible. Also of concern is whether the fluorescent molecules will interact with each other when in close proximity, resulting in self-quenching. An additional concern is whether there is non-specific binding of the fluorescent polymers to other compounds or container walls, either by themselves or in conjunction with the compound to which the fluorescent polymer is conjugated.

The applicability and value of the methods indicated above are closely tied to the availability of suitable fluorescent compounds. In particular, there is a need for fluorescent substances that have strong absorption at 405 nm, and emit fluorescence with a large Stokes shift, since excitation of these fluorophores produces less autofluorescence and also multiple chromophores fluorescing at different wavelengths can be analyzed simultaneously if the full visible and near infrared regions of the spectrum can be utilized. In recent years violet laser (405 nm) has been increasingly installed in commercial fluorescence instruments since it gives a much larger emission wavelength window than other lasers (e.g., argon laser at 488 nm and He—Ne laser at 633 nm). Phycobiliproteins have made an important contribution because of their high extinction coefficient and high quantum yield. These fluorophore-containing proteins can be covalently linked to many proteins and are used in fluorescence antibody assays in microscopy and flow cytometry. However, the phycobiliproteins have a few disadvantages that limit their biological applications, e.g., (1) the phycobiliproteins are relatively complex and tend to dissociate in highly diluted solutions; (2) They are extremely unstable and fade quickly upon illumination; (3) the phycobiliproteins have very weak absorption at 405 nm.

Brightly fluorescent polymers permit detection or location of the attached materials with great sensitivity. Certain polyfluorene polymers have demonstrated utility as labeling reagents for immunological applications, e.g. U.S. Pat. No. 8,158,444; U.S. Pat. No. 8,455,613; U.S. Pat. No. 8,354,239; U.S. Pat. No. 8,362,193; and U.S. Pat. No. 8,575,303 to Gaylord, et al.; also WO 2013/101902 to Chiu et al. The other biological applications of polyfluorene polymers have been well documented by Thomas III et al. (Chem. Rev. 2007, 107, 1339); Zhu et al (Chem. Rev. 2012, 112, 4687) and Zhu et al. (Chem. Soc. Rev., 2011, 40, 3509). Nevertheless, all the existing water-soluble polyfluorene polymers are based on unsubstituted fluorenes due to the commercial unavailability of the required key intermediates. No efforts have been devoted to explore the biological applications of substituted fluorene polymers. The unsubstituted polyfluorene polymers are known to share certain disadvantages, e.g. (1) the existing polyfluorene polymers have emission wavelength close to the UV edge of visible wavelength (400-800 nm); (2) the existing polyfluorene polymers also have a very strong tendency to self-aggregate (i.e. stack), which can significantly reduce the fluorescence quantum yields, as described in the extensive review by Mishra, et al., CHEM. REV., 100, 1973 (2000); and (3) the existing polyfluorene polymers suffer from free rotation/vibration of two benzene units around the middle single bond that significantly reduce the polymer linearity and planarity. This phenomenon is called 'loose belt effect' that is described in "MODERN MOLECULAR PHOTOCHEMISTRY", Chapters 5 and 6, University Science Books, Sausalito, Calif., authored by Nicholas J. Turro (1991). Thus, there remains a need for fluorescent polymers with improved fluorescent characteristics.

SUMMARY

The present invention addresses this need and is based on the discovery that the so-called 'loose belt effect' can be eliminated by the crosslinking of the two benzene rings. It has been surprisingly found that fluoreno[4,5-cde]oxepine-based polymers unexpectedly yielded the desired biological properties. These polymer conjugates have (1) high fluorescence quantum yield; (2) red-shifted emission; (3) high water solubility; (4) high linearity; (5) high planarity; (6) high fluorescence resonance energy transfer (FRET) efficiency when a second dye is coupled to the polymer; and (7) high photostability.

The core fluorene structure is shown below with the carbons numbered as shown. This numbering has been adopted throughout the specification.

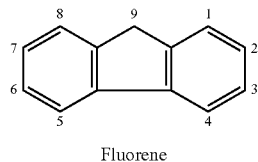

Fluorene

The basic structure of the Fluoreno[4,5-cde]oxepine monomer unit is:

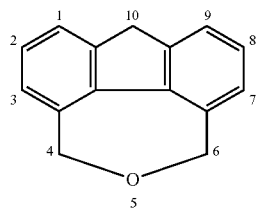

Fluoreno[4,5-cde]oxepine

Such monomers are useful in the invention and define one aspect of the invention. The invention also relates to a polymer comprising at least one Fluoreno[4,5-cde]oxepine monomer unit. The invention further relates to a polymer comprising at least one Fluoreno[4,5-cde]oxepine monomer unit attached to a biological substrate and to methods of using such polymers.

The disclosure provides a polymer comprising one or more monomers selected from the group consisting of monomer of formula A

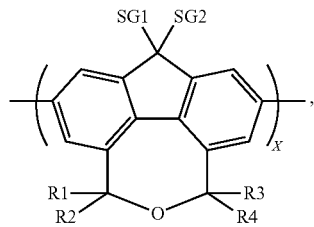

wherein X is the number of monomer A units in the polymer wherein the monomer units are consecutive or nonconsecutive and wherein X is from 6 to 100, monomer of formula B

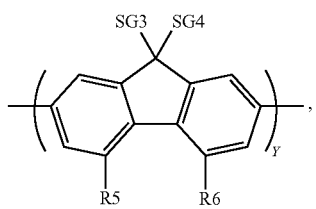

wherein Y is the number of monomer B units in the polymer wherein the monomer units are consecutive or nonconsecutive and wherein Y is from 0 to 99, and monomer of formula C

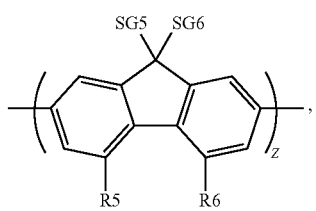

wherein Z is the number of monomer C units in the polymer wherein the monomer units are consecutive or nonconsecutive and wherein Z is from 0 to 99; wherein the ratio of X to Y+Z is >1, wherein the sum of X+Y+Z is >10, wherein R1 to R6 independently is hydrogen, an alkyl, a polyethyleneglycol (PEG), an aryl, a heteroaryl group, or a biological substrate conjugated via a linker (L-BS); wherein SG1 to SG6 independently is an alkyl, a water soluble group or a L-BS; and wherein the polymer includes end groups HG1 and HG2 wherein HG1 and HG2 independently is a hydrogen, an alkyl, a halogen, a boronyl, an aryl, a heteroaryl group or a L-BS. In some embodiments, the water soluble group is selected from a PEG group, a carboxyalkyl, a sulfonylalkyl, a phosphonylalkyl or an aminoalkyl group. A biological substrate (BS) may be an antibody, a peptide, a protein, an oligonucleotide, a nucleic acid or a carbohydrate. The linker comprises an alkyl, a PEG, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenylphosphonyl-benzoamide, an isoxazole or a succinimide group. In particular embodiments, the polymers described herein lack a biological substrate attached thereto. Instead, in particular embodiments, the polymers described herein which lack a biological substrate may be modified to include one or more biological substrates conjugated or otherwise added at one or more of R1, R2, R3, R4, R5, R6, SG1, SG2, SG3, SG4, SG5, SG6, HG1 or HG2. In particular embodiments, where the polymer comprises an L-BS, the ratio of BS to polymer is 0.2-3.

The disclosure provides a polymer comprising one or more monomers selected from the group consisting of monomer of formula D

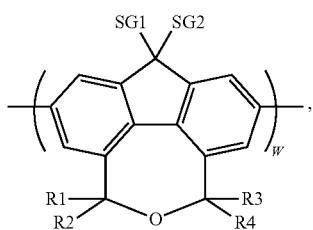

wherein W is the number of monomer D units in the polymer wherein the monomer units are consecutive or nonconsecutive and wherein W is from 6 to 100, monomer of formula E

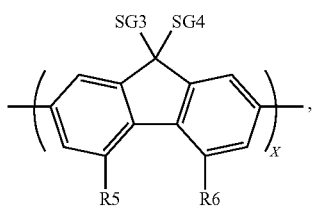

wherein X is the number of monomer E units in the polymer wherein the monomer units are consecutive or nonconsecutive and wherein X is from 0 to 98, monomer of formula F

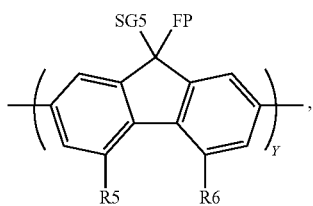

wherein Y is the number of monomer F units in the polymer wherein the monomer units are consecutive or nonconsecutive and wherein Y is from 1 to 20, fluorophore (FP) is a fluorescent dye with an exemplary fluorescent dye having an absorption maximum longer than 450 nm, and emission maximum longer than 500 nm with fluorescence quantum yield larger than 5%, and monomer of formula G

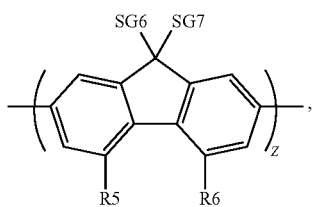

wherein Z is the number of monomer G units in the polymer wherein the monomer units are consecutive or nonconsecutive and wherein Z is from 0 to 98, and wherein the ratio of W to X+Y+Z is >1, wherein the sum of W+X+Y+Z is >10, wherein FP is a fluorophore or fluorescent dye that has absorption maximum longer than 450 nm and emission maximum longer than 500 nm with fluorescence quantum yield greater than 5%, wherein R1 to R6 independently is hydrogen, an alkyl, a polyethyleneglycol (PEG), an aryl, a heteroaryl group, or a biological substrate conjugated via a linker (L-BS), wherein SG1 to SG7 independently is an alkyl, a water soluble group or a L-BS, and wherein the polymer includes end groups HG1 and HG2 wherein HG1 and HG2 independently is a hydrogen, an alkyl, a halogen, a boronyl, an aryl, a heteroaryl group or a L-BS. In some embodiments, the water soluble group is selected from a PEG group, a carboxyalkyl, a sulfonylalkyl, a phosphonylalkyl or an aminoalkyl group. A biological substrate (BS) may be an antibody, a peptide, a protein, an oligonucleotide, a nucleic acid or a carbohydrate. The linker comprises an alkyl, a PEG, a carboxamide, and FP group, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenyl-phosphonyl-benzoamide, an isoxazole or a succinimide group. In particular embodiments, the polymers described herein lack a biological substrate attached thereto. Instead, in particular embodiments, the polymers described herein which lack a biological substrate may be modified to include one or more biological substrates conjugated or otherwise added at one or more of R1, R2, R3, R4, R5, R6, SG1, SG2, SG3, SG4, SG5, SG6, SG7, HG1 or HG2. In particular embodiments, where the polymer comprises an L-BS, the ratio of BS to polymer is 0.2-3.

The disclosure provides a polymer comprising one or more monomers selected from the group consisting of monomer of formula H

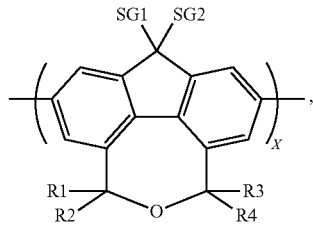

wherein X is the number of monomer H units in the polymer wherein the monomer units are consecutive or nonconsecutive and wherein X is from 0 to 100, monomer of formula I

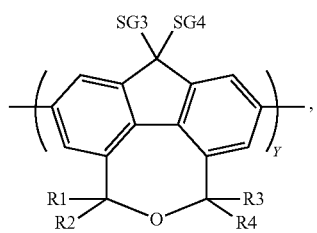

wherein Y is the number of monomer I units in the polymer wherein the monomer units are consecutive or nonconsecutive and wherein Y is from 0 to 100, and monomer of formula J

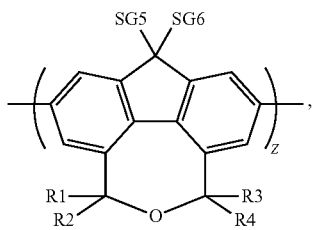

wherein Z is the number of monomer J units in the polymer wherein the monomer units are consecutive or nonconsecutive and wherein Z is from 0 to 100, wherein the sum of X+Y+Z is >10, wherein R1 to R4 independently is hydrogen, an alkyl, a polyethyleneglycol (PEG), an aryl, a heteroaryl group, or a biological substrate conjugated via a linker (L-BS), wherein SG1 to SG6 independently is an alkyl, a water soluble group or a L-BS, and wherein the polymer includes end groups HG1 and HG2 wherein HG1 and HG2 independently is a hydrogen, an alkyl, a halogen, a boronyl, an aryl, a heteroaryl group or a L-BS. In some embodiments, the water soluble group is selected from a PEG group, a carboxyalkyl, a sulfonylalkyl, a phosphonylalkyl or an aminoalkyl group. A biological substrate (BS) may be an antibody, a peptide, a protein, an oligonucleotide, a nucleic acid or a carbohydrate. The linker comprises an alkyl, a PEG, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenylphosphonyl-benzoamide, an isoxazole or a succinimide group. In particular embodiments, the polymers described herein lack a biological substrate attached thereto. Instead, in particular embodiments, the polymers described herein which lack a biological substrate may be modified to include one or more biological substrates conjugated or otherwise added at one or more of R1, R2, R3, R4, SG1, SG2, SG3, SG4, SG5, SG6, HG1 or HG2. In particular embodiments, where the polymer comprises an L-BS, the ratio of BS to polymer is 0.2-3.

The disclosure provides a polymer comprising one or more monomers selected from the group consisting of monomer of formula K

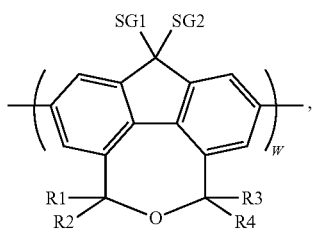

wherein W is the number of monomer K units in the polymer wherein the monomer units are consecutive or nonconsecutive and wherein W is from 0 to 100, monomer of formula L

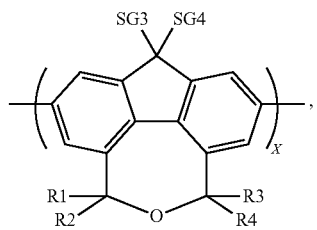

wherein X is the number of monomer L units in the polymer wherein the monomer units are consecutive or nonconsecutive and wherein X is from 0 to 100, monomer of formula M

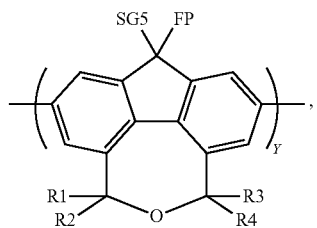

wherein Y is the number of monomer M units in the polymer wherein the monomer units are consecutive or nonconsecutive and wherein Y is from 1 to 20, fluorophore (FP) is a fluorescent dye with an exemplary fluorescent dye having an absorption maximum longer than 450 nm, and emission maximum longer than 500 nm with fluorescence quantum yield larger than 5%, and monomer of formula N

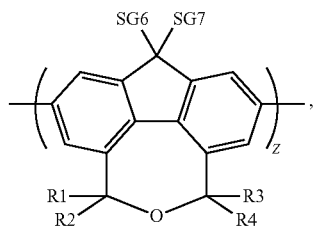

wherein Z is the number of monomer N units in the polymer wherein the monomer units are consecutive or nonconsecutive and wherein Z is from 0 to 100, wherein the sum of W+X+Y+Z is >10, wherein fluorophore (FP) is a fluorescent dye that has absorption maximum longer than 450 nm, and emission maximum longer than 500 nm with fluorescence quantum yield larger than 5%, wherein R1 to R4 independently is hydrogen, an alkyl, a polyethyleneglycol (PEG), an aryl, a heteroaryl group, or a biological substrate conjugated via a linker (L-BS), wherein SG1 to SG7 independently is an alkyl, a water soluble group or a L-BS, and wherein the polymer includes end groups HG1 and HG2 wherein HG1 and HG2 independently is a hydrogen, an alkyl, a halogen, a boronyl, an aryl, a heteroaryl group or a L-BS. In some embodiments, the water soluble group is selected from a PEG group, a carboxyalkyl, a sulfonylalkyl, a phosphonylalkyl or an aminoalkyl group. A biological substrate (BS) may be an antibody, a peptide, a protein, an oligonucleotide, a nucleic acid or a carbohydrate. The linker comprises an alkyl, a PEG, a carboxamide, an FP group, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenyl-phosphonyl-benzoamide, an isoxazole or a succinimide group. In particular embodiments, the polymers described herein lack a biological substrate attached thereto. Instead, in particular embodiments, the polymers described herein which lack a biological substrate may be modified to include one or more biological substrates conjugated or otherwise added at one or more of R1, R2, R3, R4, SG1, SG2, SG3, SG4, SG5, SG6, SG7, HG1 or HG2. In particular embodiments, where the polymer comprises an L-BS, the ratio of BS to polymer is 0.2-3.

The present disclosure provides a polymer conjugate of Formula I:

a sulfonamides, a sulfonate ester, a 1,2,3-triazole, a pyradazine, a thiazolidinea pyradazine, a thiazolidine, a 2-diphenylphosphonyl-benzoamide, an isoxazole or a succinimide group. In preferred embodiments, the linker comprises or is an alkyl or a PEG group. For embodiments which comprise multiple linkers, the linkers may be the same or different.

In particular embodiments, R1 to R6 independently represent hydrogen, methyl, or ethyl. In specific embodiments, R1 to R6 each represent hydrogen.

In some embodiments, the water soluble group is selected from a PEG group, a carboxyalkyl, a sulfonylalkyl, a phosphonylalkyl or an aminoalkyl group. Thus, in particular embodiments, SG1 to SG6 independently represent a PEG group, an alkyl, a carboxyalkyl, a sulfonylalkyl, a phosphonylalkyl, an aminoalkyl group or L-BS. In further embodiments, SG1 and SG2 are both a PEG group and SG3 to SG6

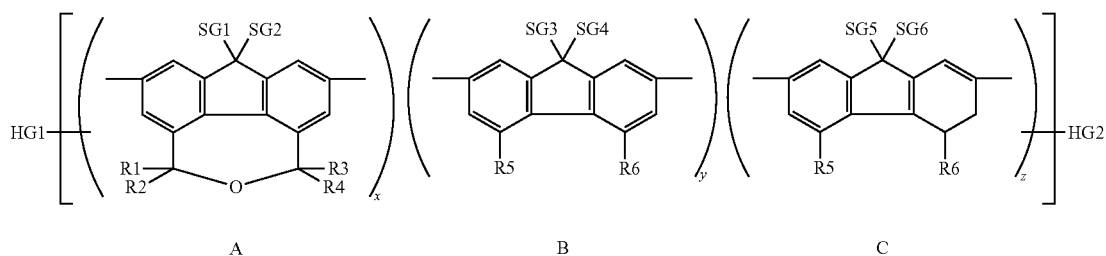

Formula I wherein the polymer conjugate comprises three monomer units represented by A, B and C that are randomly distributed along the polymer main chain;
wherein R1 to R6 independently represent hydrogen, an alkyl, a polyethyleneglycol (PEG), an aryl, a heteroaryl group, or a biological substrate conjugated via a linker (L-BS);
wherein SG1 to SG6 independently represent an alkyl, a water soluble group or a L-BS;
wherein HG1 and HG2 independently represent a hydrogen, an aryl, a halogen or a boronyl, an aryl, a heteroaryl group, or a L-BS; and
wherein x is an integer from 6-100 and y and z are each an integer independently selected from 0-99, provided that
(1) when a biological substrate is present at one or more locations within Formula I, the ratio of BS/polymer is 0.2-3,
(2) the ratio of $x/(y+z)$ is $>1$, and
(3) the sum of $x+y+z$ is $>10$.

In preferred embodiments according to all relevant aspects, monomer unit B and monomer unit C are different monomer units and are therefore non-identical. In particular embodiments, at least one SG1, SG2, SG3, SG4, SG5 and SG6 substituent is different from the remaining SG1, SG2, SG3, SG4, SG5 or SG6 substituents.

In particular embodiments, according to all relevant aspects, the monomer units selected from A-C are directly connected to one another in any sequence of monomer units (as described elsewhere herein).

In particular embodiments, the linker comprises an alkyl, a PEG, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, independently represent a PEG, an alkyl, a carboxyalkyl, a sulfonylalkyl, a phosphonylalkyl, an aminoalkyl or a L-BS.

In some embodiments, the biological substrate (BS) is an antibody, a peptide, a protein, an oligonucleotide, a nucleic acid or a carbohydrate. For those embodiments in which the polymer conjugate comprises more than one BS, each BS may be independently selected from an antibody, a peptide, a protein, an oligonucleotide, a nucleic acid or a carbohydrate.

In particular embodiments, HG1 and HG2 independently represent a hydrogen, an aryl, a halogen or a boronyl group.

In further embodiments, x is an integer from 11-80 and y and z are each an integer independently selected from 0-80. In particular embodiments, the sum of $x+y+z$ is $>20$.

In further embodiments, y and z are each an integer independently selected from 0-80.

In further embodiments, the ratio of BS/polymer is 1-2.

Thus, in particular embodiments, R1 to R6 independently represent hydrogen, methyl, or ethyl; wherein SG1 to SG6 independently represent a PEG, an alkyl, a carboxyalkyl, a sulfonylalkyl, a phosphonylalkyl, an aminoalkyl group or L-BS; wherein L comprises or is an alkyl chain or a PEG chain; BS is an antibody, a peptide, a protein, an oligonucleotide, a nucleic acid or a carbohydrate; wherein HG1 and HG2 independently represent a hydrogen, an aryl, a halogen or a boronyl; and wherein x is an integer from 11-80 and y and z are an integer independently selected from 0-80, provided that (1) the ratio of BS/polymer is 1-2, (2) the ratio of $x/(y+z)$ is $>1$, and (3) the sum of $x+y+z$ is $>20$.

In other embodiments, the disclosure provides the polymer conjugate of formula I, wherein R1 to R6 are hydrogen; wherein SG1 and SG2 are PEG; wherein SG3 to SG6 independently represent a PEG, an alkyl, a carboxyalkyl, a sulfonylalkyl, a phosphonylalkyl, an aminoalkyl or a L-BS;

wherein L comprises or is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x is an integer from 11-80 and y and z are each an integer independently selected from 0-80, provided that (1) the ratio of BS/polymer is 1-2, (2) the ratio of x/(y+z) is >1, and (3) the sum of x+y+z is >20.

In some embodiments, SG3 to SG6 independently represent a PEG group, an alkyl, a carboxyalkyl, or a L-BS.

In other embodiments, SG3 to SG6 independently represent a PEG group, an alkyl, an aminoalkyl or a L-BS.

In some embodiments, SG1 and SG2 are independently PEG6 to PEG18.

In some embodiments, the ratio of BS/polymer is 1; and the sum of x+y+z is 30-80. Thus, in these embodiments x is an integer from 16-80 and y and z are each an integer independently selected from 0-64, as appropriate. In particular embodiments, SG3 to SG6 independently represent a PEG, a methyl, a carboxyalkyl or a L-BS.

In particular embodiments, SG3 to SG6 independently represent a PEG, a methyl, an aminoalkyl or a L-BS.

Thus, in further embodiments, the disclosure provides the polymer conjugate of formula I, wherein R1 to R6 are hydrogen; wherein SG1 to SG6 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L comprises or is an alkyl chain or a PEG chain; wherein BS is an antibody, a peptide, a protein, an oligonucleotide, a nucleic acid or a carbohydrate; and wherein x is an integer from 11-80 and y and z are each an integer selected from 0-80, provided that (1) the ratio of BS/polymer is 1-2, (2) the ratio of x/(y+z) is >1, and (3) the sum of x+y+z is >20.

In some embodiments, HG1 and HG2 independently represent a hydrogen, a carboxyaryl, or a L-BS.

In other embodiments, HG1 and HG2 independently represent a halogen, a boronyl, a carboxyaryl, or a L-BS.

For the avoidance of doubt, the embodiments of R1 to R6, SG1 to SG6, HG1, HG2, L and BS as described above apply mutatis mutandis to polymer conjugates II-IV as described herein and are specifically contemplated. They also apply to the polymers of the invention defined in relation to the monomer components. Not all embodiments described above are necessarily repeated below for reasons of conciseness only.

Thus, in a further aspect, the present disclosure provides a polymer conjugate of Formula II:

wherein the polymer conjugate comprises four monomer units represented by D, E, F and G that are randomly distributed along the polymer main chain;

wherein fluorophore (FP) is a fluorescent dye that has absorption maximum longer than 450 nm, and emission maximum longer than 500 nm with fluorescence quantum yield larger than 5%;

wherein R1 to R6 independently represent hydrogen, an alkyl, a PEG, an aryl, a heteroaryl group, or a L-BS (as defined above);

wherein SG1 to SG7 independently represent an alkyl, a water soluble group or a L-BS;

wherein HG1 and HG2 independently represent an hydrogen, a halogen, a boronyl, an alkyl, an aryl, a heteroaryl group, or a L-BS;

wherein w is an integer from 6-100, x and z are each integers independently selected from 0-98; and wherein y is an integer from 1 to 20, provided that
  (1) when a biological substrate is present at one or more locations within Formula II, the ratio of BS/polymer is 0.2-3,
  (2) the ratio of w/(x+y+z) is >1, and
  (3) the sum of w+x+y+z is >10.

In preferred embodiments according to all relevant aspects, monomer unit E and monomer unit G are different monomer units and are therefore non-identical. In particular embodiments, at least one SG1, SG2, SG3, SG4, SG5, SG6 and SG7 substituent is different from the remaining SG1, SG2, SG3, SG4, SG5, SG6 or SG7 substituents.

In particular embodiments, according to all relevant aspects, the monomer units selected from D-G are directly connected to one another in any sequence of monomer units (as described elsewhere herein).

In particular embodiments, the linker comprises an alkyl, a PEG, an FP, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidinea pyradazine, a thiazolidine, a 2-diphenylphosphonyl-benzoamide, an isoxazole or a succinimide group. In preferred embodiments, the linker comprises or is an alkyl, a PEG group or an FP. For embodiments which comprise multiple linkers, the linkers may be the same or different.

In some embodiments, FP is a fluorescein, a rhodamine, a rhodol, a cyanine, a bodipy, a squaraine, a coumarin, a perylenediimide, a diketopyrrolopyrrole, a porphyrin or a phthalocyanine. For those embodiments in which the polymer conjugate comprises more than one FP, each FP may be independently selected from a fluorescein, a rhodamine, a Formula II

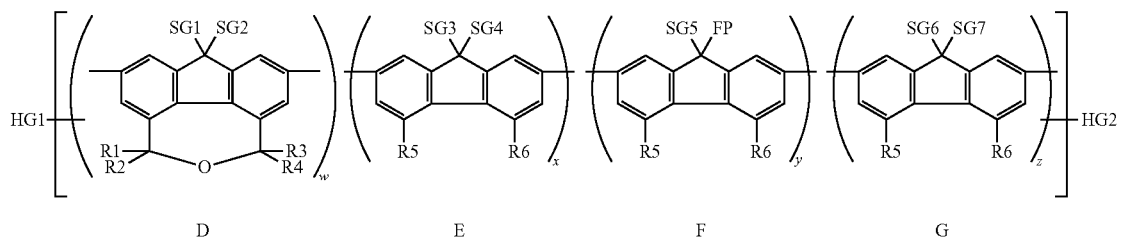

rhodol, a cyanine, a bodipy, a squaraine, a coumarin, a perylenediimide, a diketopyrrolopyrrole, a porphyrin or a phthalocyanine.

In some embodiments, R1 to R6 independently represent hydrogen, methyl, or ethyl.

In some embodiments, the water soluble group is selected from a PEG group, a carboxyalkyl, a sulfonylalkyl, a phosphonylalkyl or an aminoalkyl group. Thus, in particular embodiments, SG1 to SG7 independently represent a PEG, an alkyl, a carboxyalkyl, a sulfonylalkyl, a phosphonylalkyl, an aminoalkyl or a L-BS.

In some embodiments, BS is an antibody, a peptide, a protein, an oligonucleotide, a nucleic acid or a carbohydrate. For those embodiments in which the polymer conjugate comprises more than one BS, each BS may be independently selected from an antibody, a peptide, a protein, an oligonucleotide, a nucleic acid or a carbohydrate.

In some embodiments, HG1 and HG2 independently represent a hydrogen, an aryl, a halogen or a boronyl.

In some embodiments, w is an integer from 11-80 and x and z are each integers independently selected from 0-80. In particular embodiments, the sum of w+x+y+z is >20.

In further embodiments, x and z are each an integer independently selected from 0-80.

In further embodiments, y is an integer from 1 to 10.

In further embodiments, the ratio of BS/polymer is 1-2.

Thus, in particular embodiments, the disclosure provides the polymer conjugate of formula II, wherein FP is a fluorescein, a rhodamine, a rhodol, a cyanine, a bodipy, a squaraine, a coumarin, a perylenediimide, a diketopyrrolopyrrole, a porphyrin or a phthalocyanine; wherein R1 to R6 independently represent hydrogen, methyl, or ethyl; wherein SG1 to SG7 independently represent a PEG, an alkyl, a carboxyalkyl, a sulfonylalkyl, a phosphonylalkyl, an aminoalkyl or a L-BS; wherein L comprises or is an alkyl chain, a FP or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; wherein w is an integer from 11-80, x and z are each an integer selected from 0-80; and wherein y is an integer from 1 to 10, provided that (1) the ratio of BS/polymer is 1-2, (2) the ratio of w/(x+y+z) is >1, and (3) the sum of w+x+y+z is >20.

In some embodiments, R1 to R6 are hydrogen.

In further embodiments, the ratio of BS/polymer is 1. In further embodiments, the sum of w+x+y+z is 30-80. In particular embodiments, when the ratio of BS/polymer is 1, the sum of w+x+y+z is 30-80. Thus, in these embodiments w is an integer from 16-79 and x and z are each integers independently selected from 0-63 as appropriate.

In particular embodiments, FP is a fluorescein, a rhodamine, a cyanine, a bodipy, a squaraine, a perylenediimide, or a phthalocyanine. For those embodiments in which the polymer conjugate comprises more than one FP, each FP may be independently selected from a fluorescein, a rhodamine, a cyanine, a bodipy, a squaraine, a perylenediimide, or a phthalocyanine.

In specific embodiments, FP is a rhodamine including rhodamine 110, rhodamine 123, rhodamine 6G, rhodamine B, rhodamine Green, and rhodamine Red.

In other embodiments, FP is a cyanine including Cy2, Cy3, Cy3.5, Cy5, Cy5.5 and Cy7.

In particular embodiments, FP is a fluorescein, a rhodamine, a rhodol, a cyanine, a bodipy, a squaraine, a coumarin, a perylenediimide, a diketopyrrolopyrrole, a porphyrin or a phthalocyanine; R1 to R6 are hydrogen; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl or a L-BS; wherein L comprises or is an alkyl chain, a FP or a PEG chain; wherein BS is an antibody, a peptide, a protein, an oligonucleotide, a nucleic acid or a carbohydrate; wherein w is an integer from 11-80, x and z are each an integer selected from 0-80; and wherein y is an integer from 1 to 10, provided that (1) the ratio of BS/polymer is 1-2, (2) the ratio of w/(x+y+z) is >1, and (3) the sum of w+x+y+z is >20.

In further embodiments, the ratio of BS/polymer is 1 and the sum of x+y+z is 30-80.

In further embodiments, HG1 and HG2 independently represent a hydrogen, a carboxyaryl, or a L-BS.

In other embodiments, HG1 and HG2 independently represent a halogen, a boronyl, a carboxyaryl, or a L-BS.

In another aspect, the present disclosure provides a polymer conjugate of Formula III:

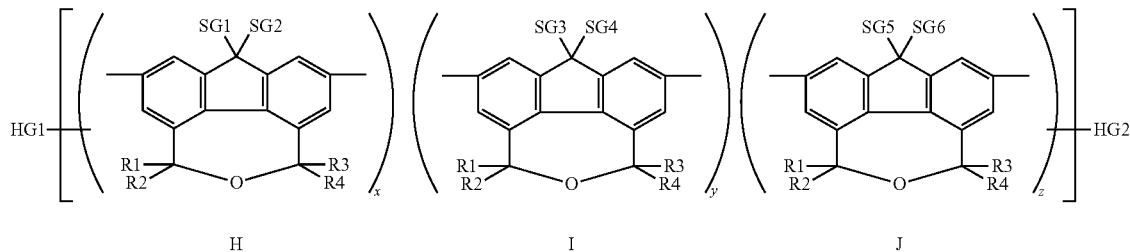

Formula III wherein the polymer conjugate comprises three monomer units represented by H, I and J that are randomly distributed along the polymer main chain;

wherein R1 to R4 independently represent hydrogen, an alkyl, a polyethyleneglycol (PEG), an aryl, a heteroaryl group, or a biological substrate conjugated via a linker (L-BS);

wherein SG1 to SG6 independently represent an alkyl, a water soluble group or a L-BS;

wherein HG1 and HG2 independently represent a hydrogen, an aryl, a halogen or a boronyl, an aryl, a heteroaryl group, or a L-BS; and wherein x, y and z are each an integer independently selected from 0-100, provided that
(1) when a biological substrate is present at one or more locations within Formula III, the ratio of BS/polymer is 0.2-3, and
(2) the sum of x+y+z is >10.

In preferred embodiments according to all relevant aspects, monomer units H-J are different monomer units and are therefore non-identical. In particular embodiments, at least one SG1, SG2, SG3, SG4, SG5 and SG6 substituent is different from the remaining SG1, SG2, SG3, SG4, SG5 or SG6 substituents.

In particular embodiments, according to all relevant aspects, the monomer units selected from H-J are directly connected to one another in any sequence of monomer units (as described elsewhere herein).

In particular embodiments, the linker comprises an alkyl, a PEG, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidinea pyradazine, a thiazolidine, a 2-diphenylphosphonyl-benzoamide, an isoxazole or a succinimide group. In preferred embodiments, the linker comprises or is an alkyl or a PEG group. For embodiments which comprise multiple linkers, the linkers may be the same or different.

In some embodiments, R1 to R4 independently represent hydrogen, methyl, or ethyl.

In some embodiments, the water soluble group is selected from a PEG group, a carboxyalkyl, a sulfonylalkyl, a phosphonylalkyl or an aminoalkyl group. Thus, in particular embodiments, SG1 to SG6 independently represent a PEG, an alkyl, a carboxyalkyl, a sulfonylalkyl, a phosphonylalkyl, an aminoalkyl or L-BS.

In further embodiments, BS is an antibody, a peptide, a protein, an oligonucleotide, a nucleic acid or a carbohydrate. For those embodiments in which the polymer conjugate comprises more than one BS, each BS may be independently selected from an antibody, a peptide, a protein, an oligonucleotide, a nucleic acid or a carbohydrate.

In further embodiments, HG1 and HG2 independently represent a hydrogen, an aryl, a halogen or a boronyl.

In further embodiments, x, y and z are each an integer independently selected from 0-80. In particular embodiments, the sum of x+y+z is >20.

In further embodiments, the ratio of BS/polymer is 1-2.

Thus, in particular embodiments, the disclosure provides the polymer conjugate of formula III, wherein R1 to R4 independently represent hydrogen, methyl, or ethyl; wherein SG1 to SG6 independently represent a PEG, an alkyl, a carboxyalkyl, a sulfonylalkyl, a phosphonylalkyl, an aminoalkyl or L-BS; wherein L comprises or is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are integer from 0-80, provided that (1) the ratio of BS/polymer is 1-2, and (2) the sum of x+y+z is >20.

In further embodiments, R1 to R4 are hydrogen.

In further embodiments, SG1 and SG2 are PEG. Thus, in particular embodiments, when SG1 and SG2 are PEG, SG3 to SG6 independently represent a PEG, an alkyl, a carboxyalkyl, a sulfonylalkyl, a phosphonylalkyl, an aminoalkyl or a L-BS.

Thus, in particular embodiments, the disclosure provides the polymer conjugate of formula III, wherein R1 to R4 are hydrogen; wherein SG1 and SG2 are PEG; wherein SG3 to SG6 independently represent a PEG, an alkyl, a carboxyalkyl, a sulfonylalkyl, a phosphonylalkyl, an aminoalkyl or a L-BS; wherein L comprises or is an alkyl chain or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; and wherein x, y and z are each an integer independently selected from 0-80, provided that (1) the ratio of BS/polymer is 1-2, and (2) the sum of x+y+z is >20.

In further embodiments, SG3 to SG6 independently represent a PEG, an alkyl, a carboxyalkyl, or a L-BS.

In other embodiments, SG3 to SG6 independently represent a PEG, an alkyl, an aminoalkyl or a L-BS.

In further embodiments, the ratio of BS/polymer is 1. In yet further embodiments, the sum of x+y+z is 30-80.

In further embodiments, SG3 to SG6 independently represent a PEG, a methyl, a carboxyalkyl or a L-BS.

In further embodiments, SG3 to SG6 independently represent a PEG, a methyl, an aminoalkyl or a L-BS.

In further embodiments, R1 to R4 are hydrogen; wherein SG1 to SG6 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L comprises or is an alkyl chain or a PEG chain; wherein BS is an antibody, a peptide, a protein, an oligonucleotide, a nucleic acid or a carbohydrate; and wherein x is an integer selected from 11-80 and y and z are each an integer independently selected from 0-80, provided that (1) the ratio of BS/polymer is 1-2, (2) the ratio of x/(y+z) is >1, and (3) the sum of x+y+z is >20.

In further embodiments, the ratio of BS/polymer is 1 and the sum of x+y+z is 30-80.

In yet further embodiments, HG1 and HG2 independently represent a hydrogen, a carboxyaryl, or a L-BS. In other embodiments, HG1 and HG2 independently represent a halogen, a boronyl, a carboxyaryl, or a L-BS.

In a further aspect, the present disclosure provides a polymer conjugate of Formula IV:

Formula IV

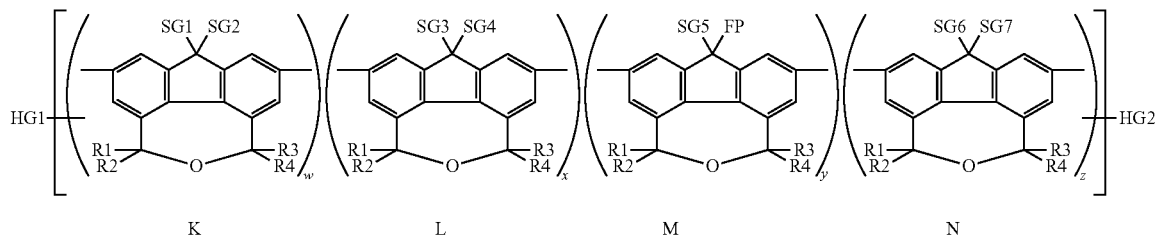

K  L  M  N wherein the polymer conjugate comprises four monomer units represented by K, L, M and N that are randomly distributed along the polymer main chain;
wherein fluorophore (FP) is a fluorescent dye that has absorption maximum longer than 450 nm, and emission maximum longer than 500 nm with fluorescence quantum yield larger than 5%;
wherein R1 to R4 independently represent hydrogen, an alkyl, a PEG, an aryl, a heteroaryl group, or a L-BS (as defined above);
wherein SG1 to SG7 independently represent an alkyl, a water soluble group or a L-BS;
wherein HG1 and HG2 independently represent an hydrogen, a halogen, a boronyl, an alkyl, an aryl, a heteroaryl group, or a L-BS;
wherein w, x and z are each an integer independently selected from 0-100; and
wherein y is an integer from 1 to 20, provided that
  (1) when a biological substrate is present at one or more locations within Formula IV, the ratio of BS/polymer is 0.2-3, and
  (2) the sum of w+x+y+z is >10.

In preferred embodiments according to all relevant aspects, monomer units K, L and N are different monomer units and are therefore non-identical. In particular embodiments, at least one SG1, SG2, SG3, SG4, SG5, SG6 and SG7 substituent is different from the remaining SG1, SG2, SG3, SG4, SG5, SG6 or SG7 substituents.

In particular embodiments, according to all relevant aspects, the monomer units selected from K-N are directly connected to one another in any sequence of monomer units (as described elsewhere herein).

In particular embodiments, the linker comprises an alkyl, a PEG, an FP, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidinea pyradazine, a thiazolidine, a 2-diphenylphosphonyl-benzoamide, an isoxazole or a succinimide group. In preferred embodiments, the linker comprises or is an alkyl, a PEG group or an FP. For embodiments which comprise multiple linkers, the linkers may be the same or different.

In some embodiments, FP is a fluorescein, a rhodamine, a rhodol, a cyanine, a bodipy, a squaraine, a coumarin, a perylenediimide, a diketopyrrolopyrrole, a porphyrin or a phthalocyanine. For those embodiments in which the polymer conjugate comprises more than one FP, each FP may be independently selected from a fluorescein, a rhodamine, a rhodol, a cyanine, a bodipy, a squaraine, a coumarin, a perylenediimide, a diketopyrrolopyrrole, a porphyrin or a phthalocyanine.

In further embodiments, R1 to R4 independently represent hydrogen, methyl, or ethyl.

In some embodiments, the water soluble group is selected from a PEG group, a carboxyalkyl, a sulfonylalkyl, a phosphonylalkyl or an aminoalkyl group. Thus, in particular embodiments, SG1 to SG7 independently represent a PEG, an alkyl, a carboxyalkyl, a sulfonylalkyl, a phosphonylalkyl, an aminoalkyl or a L-BS.

In further embodiments, BS is an antibody, a peptide, a protein, an oligonucleotide, a nucleic acid or a carbohydrate. For those embodiments in which the polymer conjugate comprises more than one BS, each BS may be independently selected from an antibody, a peptide, a protein, an oligonucleotide, a nucleic acid or a carbohydrate.

In further embodiments, HG1 and HG2 independently represent a hydrogen, an aryl, a halogen or a boronyl.

In further embodiments, w, x and z are each an integer independently selected from 0-80. In particular embodiments, the sum of w+x+y+z is >20.

In further embodiments, y is an integer from 1 to 10.

In yet further embodiments, the ratio of BS/polymer is 1-2. In particular embodiments, the ratio of BS/polymer is 1.

Thus, in particular embodiments, the disclosure provides the polymer conjugate of formula IV, wherein FP is a fluorescein, a rhodamine, a rhodol, a cyanine, a bodipy, a squaraine, a coumarin, a perylenediimide, a diketopyrrolopyrrole, a porphyrin or a phthalocyanine; wherein R1 to R4 independently represent hydrogen, methyl, or ethyl; wherein SG1 to SG7 independently represent a PEG, an alkyl, a carboxyalkyl, a sulfonylalkyl, a phosphonylalkyl, an aminoalkyl or a L-BS; wherein L comprises or is an alkyl chain, a FP or a PEG chain; wherein BS is an antibody, a peptide, a protein, an oligonucleotide, a nucleic acid or a carbohydrate; wherein HG1 and HG2 independently represent a hydrogen, an aryl, a halogen or a boronyl; wherein w, x and z are each an integer independently selected from 0-80; and wherein y is an integer from 1 to 10, provided that (1) the ratio of BS/polymer is 1-2, and (2) the sum of w+x+y+z is >20.

In further embodiments, R1 to R4 are hydrogen.

In further embodiments, the sum of w+x+y+z is 30-80. In particular embodiments, when the ratio of BS/polymer is 1, the sum of w+x+y+z is 30-80. In such embodiments, w, x and z are each an integer independently selected from 0-80.

In further embodiments, FP is a fluorescein, a rhodamine, a cyanine, a bodipy, a squaraine, a perylenediimide, or a phthalocyanine. For those embodiments in which the polymer conjugate comprises more than one FP, each FP may be independently selected from a fluorescein, a rhodamine, a cyanine, a bodipy, a squaraine, a perylenediimide, or a phthalocyanine. In particular embodiments, FP is a rhodamine including rhodamine 110, rhodamine 123, rhodamine 6G, rhodamine B, rhodamine Green, and rhodamine Red. In some embodiments, FP is a cyanine including Cy2, Cy3, Cy3.5, Cy5, Cy5.5 and Cy7.

Thus, in particular embodiments, the disclosure provides the polymer conjugate of formula IV, wherein FP is a fluorescein, a rhodamine, a rhodol, a cyanine, a bodipy, a squaraine, a coumarin, a perylenediimide, a diketopyrrolopyrrole, a porphyrin or a phthalocyanine; wherein R1 to R4 are hydrogen; wherein SG1 to SG7 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L comprises or is an alkyl chain, a FP or a PEG chain; wherein BS is an antibody, a peptide, a protein, an oligonucleotide, a nucleic acid or a carbohydrate; wherein w, x and z are each an integer independently selected from 0-80; and wherein y is an integer from 1 to 10, provided that (1) the ratio of BS/polymer is 1-2, and (2) the sum of w+x+y+z is >20.

In further embodiments, the ratio of BS/polymer is 1 and the sum of x+y+z is 30-80.

In further embodiments, HG1 and HG2 independently represent a hydrogen, a carboxyaryl, or a L-BS. In alternative embodiments, HG1 and HG2 independently represent a halogen, a boronyl, a carboxyaryl, or a L-BS.

All of the features and embodiments described above and herein are combinable unless the context makes clear otherwise. All possible combinations of the features and embodiments explicitly recited in respect of polymer conjugates according to Formulae I-IV described herein are contemplated and are to be considered to be disclosed in relation to polymer conjugates of the other formulae and the polymers of the invention defined in relation to the monomer components as relevant. Not all possible combinations are explicitly stated solely for the sake of conciseness but these combinations will be clearly and unambiguously evident to the person skilled in the art.

In a further aspect, the present disclosure provides a method of detecting an analyte in a sample, comprising a) combining said sample with a detection reagent comprising a polymer conjugate or polymer of the invention, in particular a polymer conjugate having the structure of any one of Formulae I-IV as described and further defined herein, or a polymer defined in relation to the monomer components as described and further defined herein, under conditions under which said detection reagent will bind said analyte; and b) detecting the detection reagent bound analyte by fluorescence.

The present disclosure provides a method of detecting an analyte in a sample, comprising a) combining said sample with a detection reagent comprising a polymer conjugate having the structure of Formula I under conditions under which said detection reagent will bind said analyte; and b) detecting the detection reagent bound analyte by fluorescence, Formula I

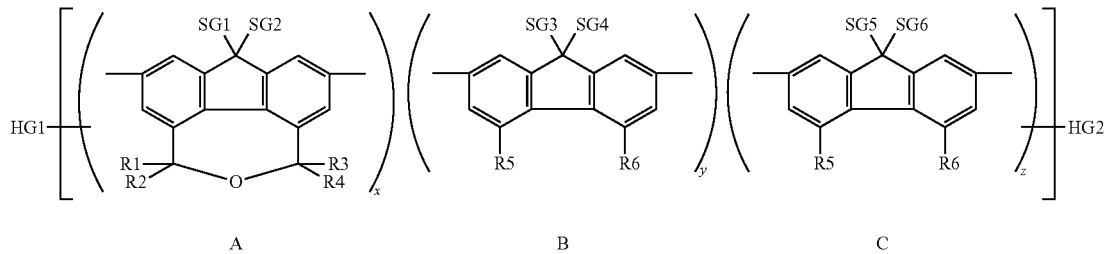

wherein the polymer conjugate comprises three monomer units represented by A, B and C that are randomly distributed along the polymer main chain;

wherein R1 to R6 independently represent hydrogen, an alkyl, a polyethyleneglycol (PEG), an aryl, a heteroaryl group, or a biological substrate (L-BS) conjugated via a linker;

wherein SG1 to SG6 independently represent an alkyl, a water soluble group or a L-BS;

wherein HG1 and HG2 independently represent a hydrogen, an aryl, a halogen or a boronyl, an aryl, a heteroaryl group, or a L-BS; and wherein x is an integer from 6-100 and y and z are each an integer independently selected from 0-99, provided that (1) the ratio of BS/polymer is 0.2-3,
(2) the ratio of x/(y+z) is >1, and
(3) the sum of x+y+z is >10.

In another aspect, the present disclosure provides a method of detecting an analyte in a sample, comprising a) combining said sample with a detection reagent comprising a polymer conjugate having the structure of Formula II under conditions under which said detection reagent will bind said analyte; and b) detecting the detection reagent bound analyte by fluorescence, Formula II

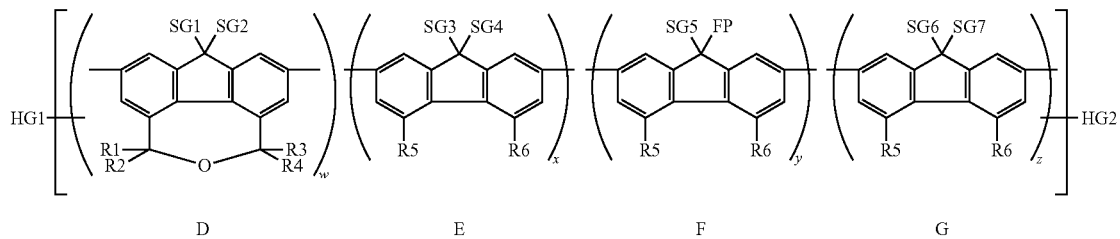

wherein the polymer conjugate comprises four monomer units represented by D, E, F and G that are randomly distributed along the polymer main chain;
wherein fluorophore (FP) is a fluorescent dye that has absorption maximum longer than 450 nm, and emission maximum longer than 500 nm with fluorescence quantum yield larger than 5%;
wherein R1 to R6 independently represent hydrogen, an alkyl, a PEG, an aryl, a heteroaryl group, or a L-BS (as defined herein);
wherein SG1 to SG7 independently represent an alkyl, a water soluble group or a L-BS;

wherein HG1 and HG2 independently represent a hydrogen, an aryl, a halogen or a boronyl, an aryl, a heteroaryl group, or a L-BS; and
wherein x, y and z are each an integer independently selected from 0-100, provided that
(1) the ratio of BS/polymer is 0.2-3, and
(2) the sum of x+y+z is >10.

In a further aspect, the present disclosure provides a method of detecting an analyte in a sample, comprising
a) combining said sample with a detection reagent comprising a polymer conjugate having the structure of Formula IV under conditions under which said detection reagent will bind said analyte; and
b) detecting the detection reagent bound analyte by fluorescence,

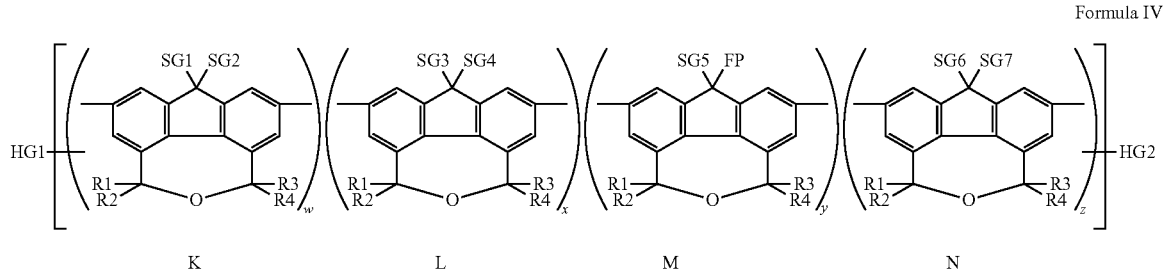

Formula IV wherein HG1 and HG2 independently represent an hydrogen, a halogen, a boronyl, an alkyl, an aryl, a heteroaryl group, or a L-BS;
wherein w is an integer from 6-100, x and z are each integers independently selected from 0-98; and wherein y is an integer from 1 to 20, provided that
(1) the ratio of BS/polymer is 0.2-3,
(2) the ratio of w/(x+y+z) is >1, and
(3) the sum of w+x+y+z is >10.

In another aspect, the present disclosure further provides a method of detecting an analyte in a sample, comprising
a) combining said sample with a detection reagent comprising a polymer conjugate having the structure of Formula III under conditions under which said detection reagent will bind said analyte; and
b) detecting the detection reagent bound analyte by fluorescence, wherein the polymer conjugate comprises four monomer units represented by K, L, M and N that are randomly distributed along the polymer main chain;
wherein fluorophore (FP) is a fluorescent dye that has absorption maximum longer than 450 nm, and emission maximum longer than 500 nm with fluorescence quantum yield larger than 5%;
wherein R1 to R4 independently represent hydrogen, an alkyl, a PEG, an aryl, a heteroaryl group, or a L-BS (as defined herein);
wherein SG1 to SG7 independently represent an alkyl, a water soluble group or a L-BS;
wherein HG1 and HG2 independently represent an hydrogen, a halogen, a boronyl, an alkyl, an aryl, a heteroaryl group, or a L-BS;

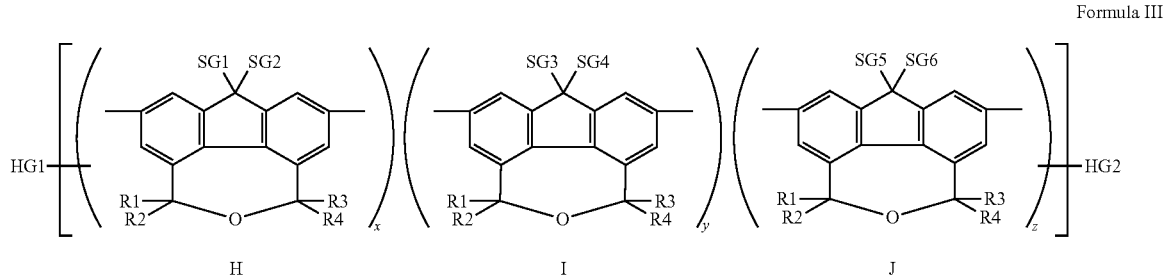

Formula III wherein the polymer conjugate comprises three monomer units represented by H, I and J that are randomly distributed along the polymer main chain;
wherein R1 to R4 independently represent hydrogen, an alkyl, a polyethyleneglycol (PEG), an aryl, a heteroaryl group, or a biological substrate conjugated via a linker (L-BS);
wherein SG1 to SG6 independently represent an alkyl, a water soluble group or a L-BS;

wherein w, x and z are each an integer independently selected from 0-100; and wherein y is an integer from 1 to 20, provided that
(1) the ratio of BS/polymer is 0.2-3, and
(2) the sum of w+x+y+z is >10.

For all polymer conjugates and polymers of the invention the position of the connection between each monomer and the main polymer chain in which the monomer is comprised is shown as a bond extending from the relevant monomer positions. Monomer units may be directly connected to one another in particular embodiments. Thus, with regard to the connection between monomer units, if the connection is between two fluorene monomers (for example, between monomers B and C of Formula I), then the connection is between the C7 of one monomer and the C2 of the other monomer as shown in the example below.

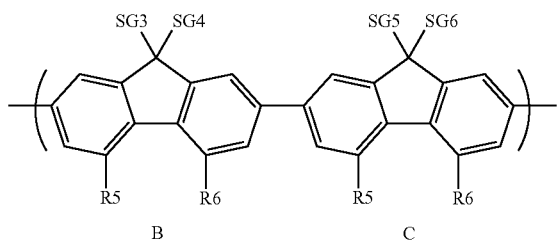

If the connection is between two fluoreno[4,5-cde]oxepine monomers (for example, monomers H and I of Formula III), then the connection is between the C2 of one monomer and the C8 of the other monomer as shown in the example below.

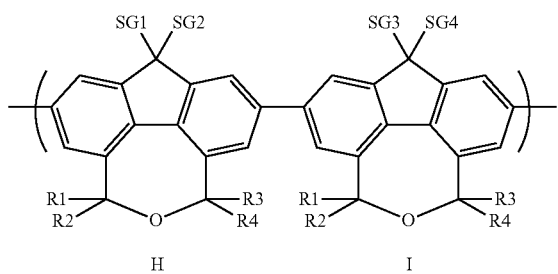

In the situation where a fluorene monomer is connected to a fluoreno[4,5-cde]oxepine monomer (for example, monomers D and E of Formula II), two types of connection are possible depending on the orientation of the monomer sequence relative to the HG1 to HG2 axis. In one orientation, the connection is made between the C8 of the fluoreno [4,5-cde]oxepine monomer to the C7 of the fluorene, for instance in the monomer sequence D-E (from HG1 terminus to HG2 terminus) as shown below.

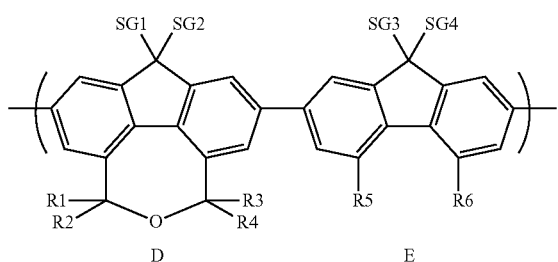

Likewise, in the other orientation, the connection between the fluorene monomer and the fluoreno[4,5-cde]oxepine monomer would be between the C2 of the fluorene and the C2 of the fluoreno[4,5-cde]oxepine, for instance in the monomer sequence E-D (from HG1 terminus to HG2 terminus) as shown in the example below.

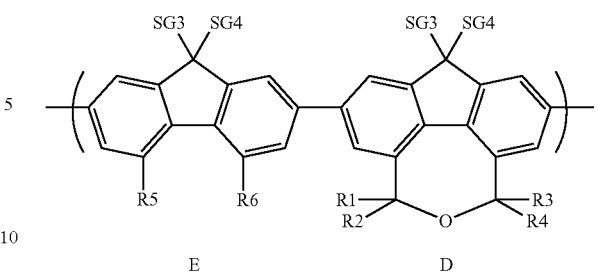

For reference, the carbon numbers for the fluorene core structure and the fluoreno[4,5-cde]oxepine basic structure discussed here and throughout are provided in the Summary of the application.

All specific embodiments of the polymer conjugates disclosed herein apply mutatis mutandis to the methods of the invention.

In some embodiments, the method comprises the use of a polymer conjugate of formula I, II, III or IV, or a polymer defined in relation to the monomer components as described and further defined herein, wherein one or more up to all of the BS present in the polymer conjugate or polymer is an antibody. In particular embodiments, one or more up to all of the BS present in the polymer conjugate or polymer is an anti-digoxigenin antibody. In alternative embodiments, one or more up to all of the BS present in the polymer conjugate or polymer is independently selected from a goat anti-mouse IgG antibody, goat anti-rabbit IgG antibody, goat anti-human IgG antibody, donkey anti-mouse IgG antibody, donkey anti-rabbit IgG antibody, donkey anti-human IgG antibody, chicken anti-mouse IgG antibody, chicken anti-rabbit IgG antibody, or chicken anti-human IgG antibody.

In yet further embodiments, the method comprises the use of a polymer conjugate of formula I, II, III or IV, or a polymer defined in relation to the monomer components as described and further defined herein, wherein one or more up to all of the BS present in the polymer conjugate or polymer is independently selected from an avidin, streptavidin, neutravidin, avidinDN, or avidinD molecule.

In yet further embodiments, the analyte detected by the methods disclosed herein is a target protein expressed on a cell surface.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

BRIEF DESCRIPTION OF THE DRAWINGS

The foregoing and other features and advantages of the present embodiments will be more fully understood from the following detailed description of illustrative embodiments taken in conjunction with the accompanying drawings in which.

DETAILED DESCRIPTION

Figure 1:
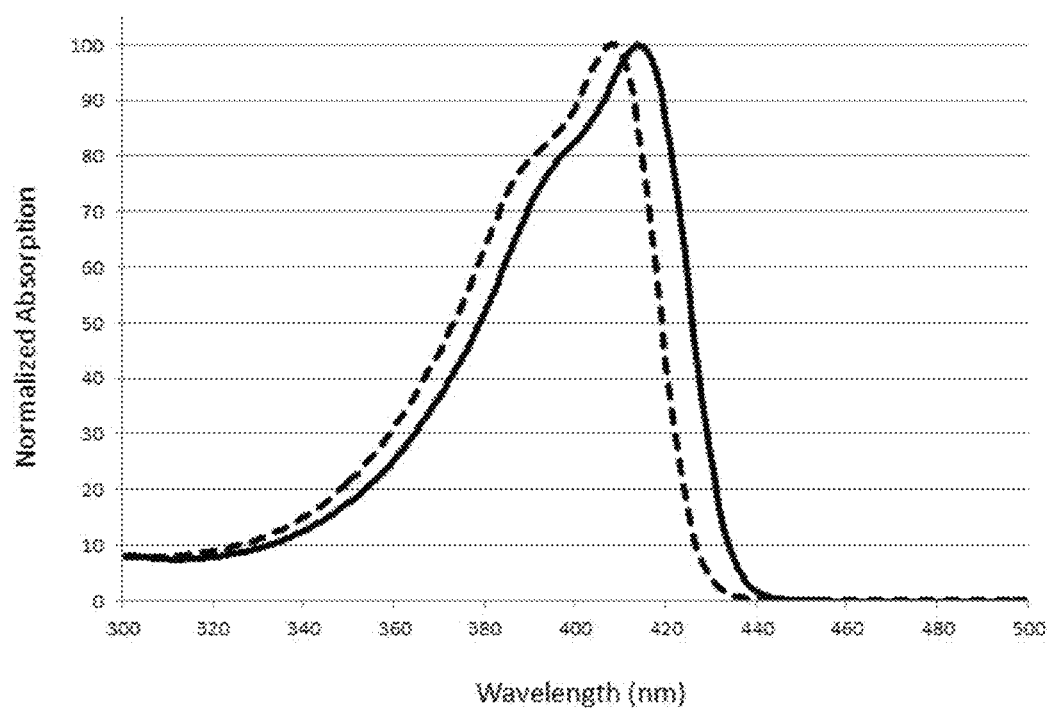
FIG. 1. The normalized absorption spectra of polyfluorene (dashed line) and polyfluoreno[4,5-cde]oxepine (PFO, solid line) in PBS buffer (pH=7.4). PFO has stronger absorption (extinction coefficient=3,500,000 cm$^{-1}$M$^{-1}$) than polyfluorene (extinction coefficient=2,100,000 cm$^{-1}$M$^{-1}$). PFO also has longer absorption wavelength than that of polyfluorene.
Figure 2:
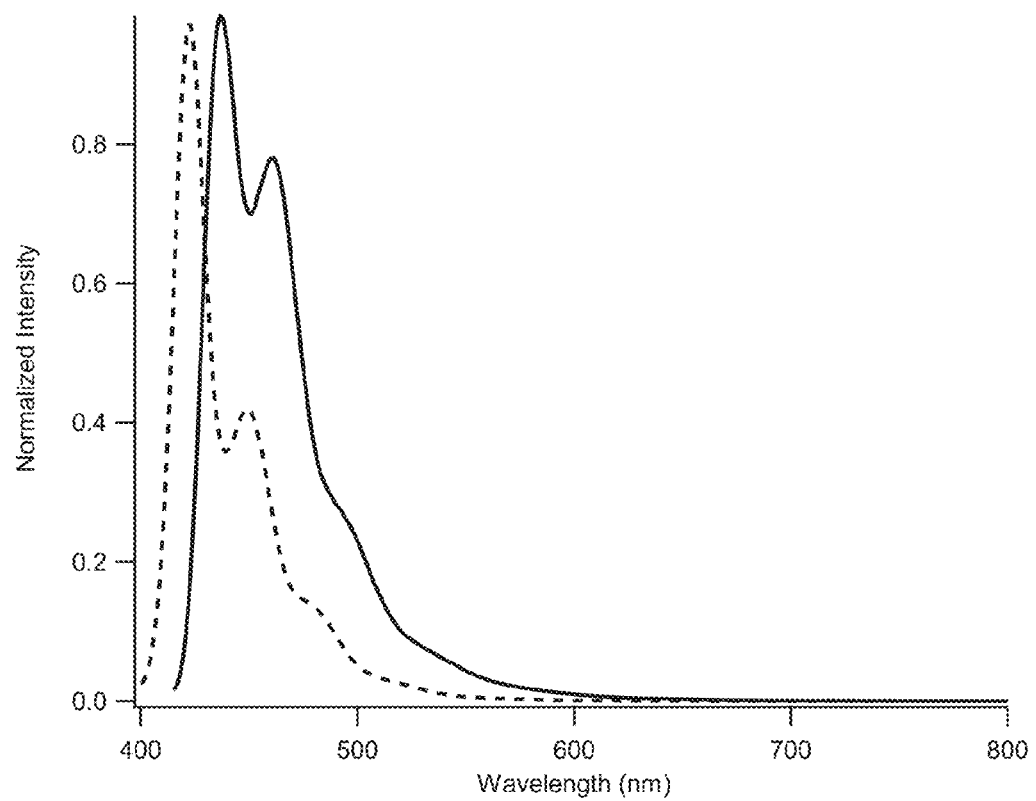
FIG. 2. The normalized fluorescence spectra of polyfluorene (dashed line) and polyfluoreno[4,5-cde]oxepine (PFO, solid line) in PBS buffer (pH=7.4). PFO has longer emission wavelengths than that of polyfluorene.

All the existing water-soluble polyfluorene polymers are based on unsubstituted fluorenes due to the commercial unavailability of the required key intermediates. No efforts have been devoted to explore the biological applications of substituted fluorene polymers. U.S. Pat. No. 8,598,306 (to Mary McKiernan and Jonathan Pillow) disclosed a hypothetic fluoreno[4,5-cde]oxepine monomer. However, the monomer is irrelevant to this invention for a few reasons. (1). The one skilled in the art cannot use the monomer described by Mary McKieman and Jonathan Pillow to make a useful biological polymer. The polymers that Mary McKieman and Jonathan Pillow specifically designed for electronic devices (e.g., OLED) are extremely hydrophobic. The polymers resulted from the hypothetic fluoreno [4,5-cde] oxepine monomers are insoluble in water, thus cannot be used in a biological system that always requires a aqueous environment. (2). It is evident that even the hypothetic fluoreno[4,5-cde]oxepine monomer cannot be made by the method disclosed by Mary McKiernan and Jonathan Pillow. U.S. Pat. No. 8,598,306 disclosed the synthesis method catalyzed by AlCl$_3$ and BF$_3$. Under these conditions the oxepine ring would be destroyed. (3). No spectral and biological studies of the hypothetic fluoreno[4,5-cde]oxepine polymers has been described by Mary McKiernan and Jonathan Pillow. (4). It is impossible to conjugate the hypothetic fluoreno[4,5-cde]oxepine polymers of Mary McKieman and Jonathan Pillow to a biological substrate for at least three reasons. (a). Mary McKiernan and Jonathan Pillow's hypothetic polymers lack a biologically compatible functional group for connecting to a biological substrate. (b). Their extremely poor water solubility would make any biological conjugates resulted from the hypothetic fluoreno [4,5-cde]oxepine polymers useless. (c). The aggregation of the hypothetic fluoreno[4,5-cde]oxepine polymers would make it impossible to explore their biological applications since all the biological conjugates are used in aqueous systems.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Use of the singular forms "a," "an," and "the" include plural references unless the context clearly dictates otherwise. Thus, for example, reference to "a probe" includes a plurality of probes, and the like. Additionally, use of specific plural references, such as "two," "three," etc., read on larger numbers of the same subject unless the context clearly dictates otherwise.

Terms such as "connected," "attached," "conjugated" and "linked" are used interchangeably herein and encompass direct as well as indirect connection, attachment, linkage or conjugation unless the context clearly dictates otherwise. As used herein, the terms "polymer conjugate" and "conjugated polymer" refer to a polymer of the invention in direct or indirect connection, attachment, linkage or conjugation with a biological substrate as defined herein.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

length emission, so they are particularly useful for samples that are transparent to infrared wavelengths.

The present disclosure provides polymer conjugates comprising fluoreno[4,5-cde]oxepine-based polymer conjugates. These biological conjugates are used to locate or detect the interaction or presence of analytes or ligands in a sample. Also contemplated are kits incorporating such polymers or polymer conjugates for use in the methods disclosed herein.

Thus, the present disclosure provides polymer conjugates comprising a fluoreno[4,5-cde]oxepine-based polymer conjugate that contains: 1) a polyfluoreno[4,5-cde]oxepine; and optionally, 2) a biological substrate (BS). The polymer conjugates of the invention typically have the structure of Formula I:

Formula I

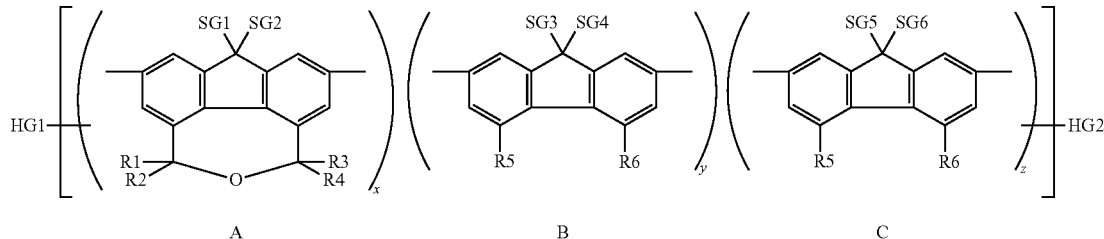

In arriving at the invention, a variety of chemical modifications of fluorene polymers have been tried in order to explore their biological detection applications. It has been noted that any substitutions at positions 1, 2, 3, 6, 7, and 8 significantly decrease the fluorescence intensity of the resulting polymer conjugates. In addition, these substituted fluorene polymer conjugates also have poor water solubility. Efforts were focused on positions 4 and 5. The initial efforts on different substitutions and different crosslinkings at positions 4 and 5 did not generate the desired polymers. The halogenation, alkylation, amination of positions 4 and 5 and the cross-linkings of positions 4 and 5 by 5, 6 and 8-membered groups gave undesired fluorene polymer conjugates. However, fluoreno[4,5-cde]oxepine-based polymer conjugates unexpectedly gave the desired biological properties. It has been found that these polymer conjugates have the following advantageous properties:

(1) High fluorescence quantum yield;
(2) Red-shifted emission;
(3) High water solubility;
(4) High linearity;
(5) High planarity;
(6) High fluorescence resonance energy transfer (FRET) efficiency when a second fluorophore is coupled to the polymer; and
(7) High photostability.

It has been discovered that the fluoreno[4,5-cde]oxepine polymers unexpectedly mitigated problems discussed in the background section and resulted in fluorescent polymer conjugates that are substantially more fluorescent when conjugated to proteins, nucleic acids and other biopolymers. The enhanced fluorescence intensity of polymer-biomolecule conjugates of the invention results in greater assay sensitivity.

Furthermore, the disclosure provides polymer conjugates that typically exhibit absorbance maxima around 405 nm, so these polymer conjugates can be selected to match the principal emission lines of the violet laser (405 nm). Some polymer conjugates of the invention exhibit very long wavewherein the polymer conjugate comprises three monomer units represented by A, B and C that are randomly distributed along the polymer main chain;

wherein R1 to R6 independently represent hydrogen, an alkyl, a polyethyleneglycol (PEG), an aryl, a heteroaryl group, or a biological substrate conjugated via a linker (L-BS);

wherein SG1 to SG6 independently represent an alkyl, a water soluble group or a L-BS;

wherein HG1 and HG2 independently represent a hydrogen, an aryl, a halogen or a boronyl, an aryl, a heteroaryl group, or a L-BS; and wherein x is an integer from 6-100 and y and z are each an integer independently selected from 0-99, provided that
(1) when a biological substrate is present at one or more locations within Formula I, the ratio of BS/polymer is 0.2-3,
(2) the ratio of x/(y+z) is >1, and
(3) the sum of x+y+z is >10.

As used herein, the term "alkyl" (alone or in combination with another term(s)) means a straight- or branched-chain saturated hydrocarbyl substituent typically containing 1 to 15 carbon atoms, such as 1 to 10, 1 to 8, 1 to 6, or 1 to 4 carbon atoms. A "$C_n$ alkyl" group refers to an aliphatic group containing n carbon atoms. For example, a $C_1$-$C_{10}$ alkyl group contains 1, 2, 3, 4, 5, 6, 7, 8, 9 or 10 carbon atoms. Attachment to the alkyl group occurs through a carbon atom. Examples of such substituents include methyl, ethyl, n-propyl, isopropyl, n-butyl, isobutyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched). The term "alkyl" also includes cycloalkyl groups meaning a saturated cyclic hydrocarbon substituent typically containing 3 to 14 carbon ring atoms. A cycloalkyl may be a single carbon ring, which typically contains 3 to 8 carbon ring atoms and more typically 3 to 6 ring atoms. It is understood that attachment to a cycloalkyl group is via a ring atom of the cycloalkyl group. Examples of single-ring cycloalkyls include cyclopropyl (cyclopropanyl), cyclobutyl (cyclobutanyl), cyclopentyl (cyclopentanyl), cyclohexyl (cyclohexanyl). A cycloalkyl may alternatively be polycyclic or contain more than one ring. Examples of polycyclic cycloalkyls include bridged, fused, and spirocyclic cycloalkyl. In a spirocyclic cycloalkyl, one atom is common to two different rings. An example of a spirocyclic cycloalkyl is spiropentanyl. In a bridged cycloalkyl, the rings share at least two common non-adjacent atoms. Examples of bridged cycloalkyls include bicyclo[2.2.1]heptanyl, bicyclo[2.2.1]hept-2-enyl, and adamantanyl. In a fused-ring cycloalkyl system, two or more rings may be fused together, such that two rings share one common bond. Examples of two- or three-fused ring cycloalkyls include naphthalenyl, tetrahydronaphthalenyl (tetralinyl), indenyl, indanyl (dihydroindenyl), anthracenyl, phenanthrenyl, and decalinyl.

As used herein, a "polyethyleneglycol (PEG)" group is well-known in the art and is a polymer of variable chain length composed of ethylene oxide monomer units, the radical of which can be represented by the following formula: —(O—CH$_2$—CH$_2$)$_n$—OH. In particular embodiments, n=8-20. In preferred embodiments, n=12. The term includes branched PEGs, star PEGs and comb PEGs, all of which are known in the art. Specific examples of PEG groups for use in the invention are PEG6-PEG18.

As used herein, the term "aryl" (alone or in combination with another term(s)) means an aromatic cycloalkyl containing from 6 to 14 carbon ring atoms, or 3 to 8, 3 to 6 or 5 to 6 carbon ring atoms. An aryl may be monocyclic or polycyclic (i.e., may contain more than one ring). In the case of polycyclic aromatic rings, only one ring in the polycyclic system is required to be unsaturated while the remaining ring(s) may be saturated, partially saturated or unsaturated. Attachment to the aryl group occurs through a carbon atom contained in the ring. Examples of aryl groups include phenyl, naphthyl, indenyl, indanyl, and tetrahydronapthyl.

As used herein, the term "heteroaryl" (alone or in combination with another term(s)) means an aryl group wherein at least one of the ring atoms is a heteroatom (i.e. oxygen, nitrogen, or sulfur). A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl; and 6/6-membered fused rings such as benzopyranyl, quinolinyl, isoquinolinyl, cinnolinyl, quinazolinyl, and benzoxazinyl.

As used herein, "HG1" and "HG2" represent the terminal ends of the polymer conjugate and they independently represent a hydrogen, an aryl, a halogen or a boronyl, an aryl, a heteroaryl group, or a L-BS (as defined herein).

The "biological substrate" is as defined elsewhere herein.

As used herein, a "water soluble group" includes a hydrophilic functional group. The hydrophilic functional group is used to increase or enhance solubility of the polymer in water. The polymers described herein include one or more water soluble groups, i.e. hydrophilic functional groups, at one or more monomers as described herein so as to impart sufficient water solubility to the polymer to facilitate functioning in an aqueous environment. Exemplary water-soluble groups useful to create water-soluble conjugated polymers as described herein and the concept of water solubility as it applies to conjugated polymers are described in Liu et al., Chem. Mater., 2004, 16(23), pp. 4467-4476 and Feng et al., Chem. Soc. Rev., 2010, 39, pp. 2411-2419 each of which are hereby incorporated by reference in their entireties. Specific examples of a "water soluble group" or a hydrophilic functional group include a PEG group, a carboxyalkyl, a sulfonylalkyl, a phosphonylalkyl or an aminoalkyl group.

As used herein, the term "halogen" or "halo" refers to a group selected from chlorine, fluorine, bromine and iodine.

As used herein, the term "sulfonyl" or "sulfo" means a sulfonic acid substituent (—S(O)$_2$OH), or salt of sulfonic acid (sulfonate). The term includes sulfonic acid groups wherein the OH of the sulfonyl group has been replaced with another substituent.

Similarly, by "carboxy" is meant a carboxylic acid substituent or salt of carboxylic acid.

"Phosphonyl", as used herein, means a phosphonic acid substituent and includes salts of phosphonate. The term also includes phosphonyl radicals such as —P(O)(R$_1$)R$_2$ wherein R$_1$ and R$_2$ are each another substituent such as an alkyl group, wherein R$_1$ and R$_2$ may be the same or different.

"Boronyl", as used herein, means boronic acid and includes salts of boronate. The term includes radicals of the formula —B(R)OH, —B(R$_1$)OR$_2$ or —B(R)$_2$ wherein R$_1$ and R$_2$ are each another substituent such as an alkyl group, wherein R$_1$ and R$_2$ may be the same or different.

As used herein, unless otherwise specified, the alkyl portions of substituents such as alkyl, alkoxy, arylalkyl, alkylamino, dialkylamino, trialkylammonium (—N$^+$(R$_1$)(R$_2$)(R$_3$) wherein R$_1$-R$_3$ are each the same or different alkyl), or perfluoroalkyl are optionally saturated, unsaturated, linear or branched, and all alkyl, alkoxy, alkylamino, and dialkylamino substituents are themselves optionally further substituted by carboxy, sulfo, amino, or hydroxy.

As used herein, the term "amino" refers to the —NH$_2$ group. The amino group can be optionally substituted (a "substituted amino") with one or more substituents, which can be the same or different. Amino group substituents may be, but are not limited to, an alkyl, aryl and/or a heterocyclyl group.

As used herein, the term "alkoxy" refers to an —O-alkyl group. The alkoxy group can refer to linear, branched, or cyclic, saturated or unsaturated hydrocarbon chains, including, for example, methoxyl, ethoxyl, propoxyl, isopropoxyl, butoxyl, t-butoxyl and pentoxyl. The alkoxy group can be optionally substituted (a "substituted alkoxy") with one or more substituents.

The term "hydroxyl" refers to an —OH group.

In particular embodiments, according to all relevant aspects, the monomer units selected from A-C are directly connected to one another in any sequence of monomer units (as described elsewhere herein).

In particular embodiments, the linker comprises an alkyl, a PEG, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenylphosphonyl-benzoamide, an isoxazole or a succinimide group. In preferred embodiments, the linker comprises or is an alkyl or a PEG group. For embodiments which comprise multiple linkers, the linkers may be the same or different.

In preferred embodiments, R1 to R6 independently represent hydrogen, methyl, or ethyl; SG1 to SG6 independently represent a PEG, an alkyl, a carboxyalkyl, a sulfonylalkyl, a phosphonylalkyl, an aminoalkyl or L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl; x is an integer from 11-80 and y and z are each an integer independently selected from 0-80, provided that (1) the ratio of BS/polymer is 1-2, (2) the ratio of x/(y+z) is >1, and (3) the sum of x+y+z is >20.

In other preferred embodiments, R1 to R6 are hydrogen; SG1 and SG2 are PEG; SG3 to SG6 independently represent a PEG, an alkyl, a carboxyalkyl, a sulfonylalkyl, a phosphonylalkyl, an aminoalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl; x is an integer from 11-80 and y and z are each an integer independently selected from 0-80, provided that (1) the ratio of BS/polymer is 1-2, (2) the ratio of x/(y+z) is >1, and (3) the sum of x+y+z is >20.

In other preferred embodiments, R1 to R6 are hydrogen; SG1 and SG2 are PEG; SG3 to SG6 independently represent a PEG, an alkyl, a carboxyalkyl, a sulfonylalkyl, a phosphonylalkyl, or an aminoalkyl; HG1 and HG2 independently represent a hydrogen, an aryl, a halogen, boronyl, or a L-BS; L comprises or is an alkyl chain or a PEG chain; BS is an antibody, a peptide, a protein, an oligonucleotide, a nucleic acid or a carbohydrate; x is an integer from 11-80 and y and z are each an integer independently selected from 0-80, provided that (1) the ratio of BS/polymer is 1-2, (2) the ratio of x/(y+z) is >1, and (3) the sum of x+y+z is >20.

In other preferred embodiments, R1 to R6 are hydrogen; SG1 and SG2 are PEG; SG3 to SG6 independently represent a PEG, an alkyl, a carboxyalkyl, or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; x is an integer from 11-80 and y and z are each an integer independently selected from 0-80, provided that (1) the ratio of BS/polymer is 1-2, (2) the ratio of x/(y+z) is >1, and (3) the sum of x+y+z is >20.

In other preferred embodiments, R1 to R6 are hydrogen; SG1 and SG2 are PEG; SG3 to SG6 independently represent a PEG, an alkyl, a sulfonylalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; x is an integer from 11-80 and y and z are each an integer independently selected from 0-80, provided that (1) the ratio of BS/polymer is 1-2, (2) the ratio of x/(y+z) is >1, and (3) the sum of x+y+z is >20.

In other preferred embodiments, R1 to R6 are hydrogen; wherein SG1 and SG2 are PEG; SG3 to SG6 independently represent a PEG, an alkyl, a phosphonylalkyl, or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; x is an integer from 11-80 and y and z are each an integer independently selected from 0-80, provided that (1) the ratio of BS/polymer is 1-2, (2) the ratio of x/(y+z) is >1, and (3) the sum of x+y+z is >20.

In other preferred embodiments, R1 to R6 are hydrogen; SG1 and SG2 are PEG; SG3 to SG6 independently represent a PEG, an alkyl, an aminoalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; x is an integer from 11-80 and y and z are each an integer independently selected from 0-80, provided that (1) the ratio of BS/polymer is 1-2, (2) the ratio of x/(y+z) is >1, and (3) the sum of x+y+z is >20.

In other preferred embodiments, R1 to R6 are hydrogen; SG1 and SG2 are PEG; SG3 to SG6 independently represent a PEG, an alkyl, a carboxyalkyl, or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; x is an integer from 16-80 and y and z are each an integer independently selected from 0-64, provided that (1) the ratio of BS/polymer is 1, (2) the ratio of x/(y+z) is >1, and (3) the sum of x+y+z is 30-80.

In other preferred embodiments, R1 to R6 are hydrogen; SG1 and SG2 are PEG; SG3 to SG6 independently represent a PEG, an alkyl, a sulfonylalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; x is an integer from 16-80 and y and z are each an integer independently selected from 0-64, provided that (1) the ratio of BS/polymer is 1, (2) the ratio of x/(y+z) is >1, and (3) the sum of x+y+z is 30-80.

In other preferred embodiments, R1 to R6 are hydrogen; SG1 and SG2 are PEG; SG3 to SG6 independently represent a PEG, an alkyl, a phosphonylalkyl, or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; x is an integer from 16-80 and, y and z are each an integer independently selected from 0-64, provided that (1) the ratio of BS/polymer is 1, (2) the ratio of x/(y+z) is >1, and (3) the sum of x+y+z is 30-80.

In other preferred embodiments, R1 to R6 are hydrogen; SG1 and SG2 are PEG; SG3 to SG6 independently represent a PEG, an alkyl, an aminoalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; x is an integer from 16-80 and, y and z are each an integer independently selected from 0-64, provided that (1) the ratio of BS/polymer is 1, (2) the ratio of x/(y+z) is >1, and (3) the sum of x+y+z is 30-80.

A preferred embodiment is a compound of Formula II:

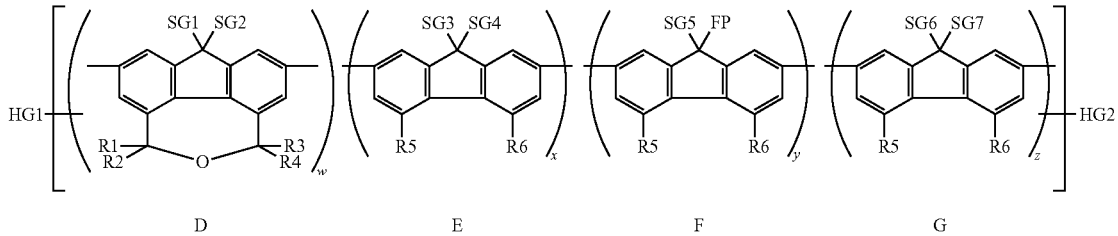

Formula II wherein the polymer conjugate comprises four monomer units represented by D, E, F and G that are randomly distributed along the polymer main chain;

wherein fluorophore (FP) is a fluorescent dye that has absorption maximum longer than 450 nm, and emission maximum longer than 500 nm with fluorescence quantum yield larger than 5%;

wherein R1 to R6 independently represent hydrogen, an alkyl, a PEG, an aryl, a heteroaryl group, or a L-BS (as defined herein);

wherein SG1 to SG7 independently represent an alkyl, a water soluble group or a L-BS;

wherein HG1 and HG2 independently represent an hydrogen, a halogen, a boronyl, an alkyl, an aryl, a heteroaryl group, or a L-BS;

wherein w is an integer from 6-100 and x and z are each integers independently selected from 0-98; and wherein y is an integer from 1 to 20, provided that
(1) when a biological substrate is present at one or more locations within Formula II, the ratio of BS/polymer is 0.2-3,
(2) the ratio of w/(x+y+z) is >1, and
(3) the sum of w+x+y+z is >10.

In particular embodiments, according to all relevant aspects, the monomer units selected from D-G are directly connected to one another in any sequence of monomer units (as described elsewhere herein).

In particular embodiments, the linker comprises an alkyl, a PEG, an FP, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenylphosphonyl-benzoamide, an isoxazole or a succinimide group. In preferred embodiments, the linker comprises or is an alkyl, a PEG group or an FP. For embodiments which comprise multiple linkers, the linkers may be the same or different.

In preferred embodiments, FP is a fluorescein, a rhodamine, a rhodol, a cyanine, a bodipy, a squaraine, a coumarin, a perylenediimide, a diketopyrrolopyrrole, a porphyrin or a phthalocyanine; R1 to R6 independently represent hydrogen, methyl, or ethyl; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; HG1 and HG2 independently represent a hydrogen, an aryl, a halogen or a boronyl; w is an integer from 11-80 and x and z are each integers independently selected from 0-80; and wherein y is an integer from 1 to 10, provided that (1) the ratio of BS/polymer is 1-2, (2) the ratio of w/(x+y+z) is >1, and (3) the sum of w+x+y+z is >20.

In other preferred embodiments, FP is a fluorescein, a rhodamine, a rhodol, a cyanine, a bodipy, a squaraine, a coumarin, a perylenediimide, a diketopyrrolopyrrole, a porphyrin or a phthalocyanine; R1 to R6 independently represent hydrogen, methyl, or ethyl; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; w is an integer from 11-80 and x and z are each integers independently selected from 0-80; and wherein y is an integer from 1 to 10, provided that (1) the ratio of BS/polymer is 1-2, (2) the ratio of w/(x+y+z) is >1, and (3) the sum of w+x+y+z is >20.

In other preferred embodiments, FP is a fluorescein, a rhodamine, a rhodol, a cyanine, a bodipy, a squaraine, a coumarin, a perylenediimide, a diketopyrrolopyrrole, a porphyrin or a phthalocyanine; R1 to R6 are hydrogen; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; HG1 and HG2 independently represent a hydrogen, an aryl, a halogen or a boronyl; w is an integer from 11-80 and x and z are each integers independently selected from 0-80; and wherein y is an integer from 1 to 10, provided that (1) the ratio of BS/polymer is 1-2, (2) the ratio of w/(x+y+z) is >1, and (3) the sum of w+x+y+z is >20.

In other preferred embodiments, FP is a fluorescein, a rhodamine, a rhodol, a cyanine, a bodipy, a squaraine, a coumarin, a perylenediimide, a diketopyrrolopyrrole, a porphyrin or a phthalocyanine; R1 to R6 are hydrogen; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; w is an integer from 11-80 and x and z are each integers independently selected from 0-80; and wherein y is an integer from 1 to 10, provided that (1) the ratio of BS/polymer is 1-2, (2) the ratio of w/(x+y+z) is >1, and (3) the sum of w+x+y+z is >20.

In other preferred embodiments, FP is a fluorescein, a rhodamine, a cyanine, a bodipy, a squaraine, a perylenediimide, a diketopyrrolopyrrole, or a phthalocyanine; R1 to R6 are hydrogen; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; HG1 and HG2 independently represent a hydrogen, an aryl, a halogen or a boronyl; w is an integer from 11-80 and x and z are each integers independently selected from 0-80; and wherein y is an integer from 1 to 10, provided that (1) the ratio of BS/polymer is 1-2, (2) the ratio of w/(x+y+z) is >1, and (3) the sum of w+x+y+z is >20.

In other preferred embodiments, FP is a fluorescein, a rhodamine, a cyanine, a bodipy, a squaraine, a coumarin, a perylenediimide, a diketopyrrolopyrrole, or a phthalocyanine; R1 to R6 are hydrogen; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; w is an integer from 11-80 and x and z are each integers independently selected from 0-80; and wherein y is an integer from 1 to 10, provided that (1) the ratio of BS/polymer is 1-2, (2) the ratio of w/(x+y+z) is >1, and (3) the sum of w+x+y+z is >20.

In other preferred embodiments, FP is a fluorescein, a rhodamine, a cyanine, a bodipy, a squaraine, a perylenediimide, a diketopyrrolopyrrole, or a phthalocyanine; R1 to R6 are hydrogen; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; HG1 and HG2 independently represent a hydrogen, an aryl, a halogen or a boronyl; w is an integer from 16-79 and x and z are each integers independently selected from 0-63; and wherein y is an integer from 1 to 10, provided that (1) the ratio of BS/polymer is 1, (2) the ratio of w/(x+y+z) is >1, and (3) the sum of w+x+y+z is 30-80.

In other preferred embodiments, FP is a fluorescein, a rhodamine, a cyanine, a bodipy, a squaraine, a coumarin, a perylenediimide, a diketopyrrolopyrrole, or a phthalocyanine; R1 to R6 are hydrogen; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; w is an integer from 16-79 and x and z are each integers independently selected from 0-63; and wherein y is an integer from 1 to 10, provided that (1) the ratio of BS/polymer is 1, (2) the ratio of w/(x+y+z) is >1, and (3) the sum of w+x+y+z is 30-80.

In other preferred embodiments, FP is a fluorescent dye selected from Table 1; R1 to R6 are hydrogen; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; wherein HG1 and HG2 independently represent a hydrogen, an aryl, a halogen or a boronyl; w is an integer from 16-79 and x and z are each integers independently selected from 0-63; and wherein y is an integer from 1 to 10, provided that (1) the ratio of BS/polymer is 1, (2) the ratio of w/(x+y+z) is >1, and (3) the sum of w+x+y+z is 30-80.

In other preferred embodiments, FP is a fluorescent dye selected from Table 1; R1 to R6 are hydrogen; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; w is an integer from 16-79 and x and z are each integers independently selected from 0-63; and wherein y is an integer from 1 to 10, provided that (1) the ratio of BS/polymer is 1, (2) the ratio of w/(x+y+z) is >1, and (3) the sum of w+x+y+z is 30-80.

A preferred embodiment is a compound of Formula III:

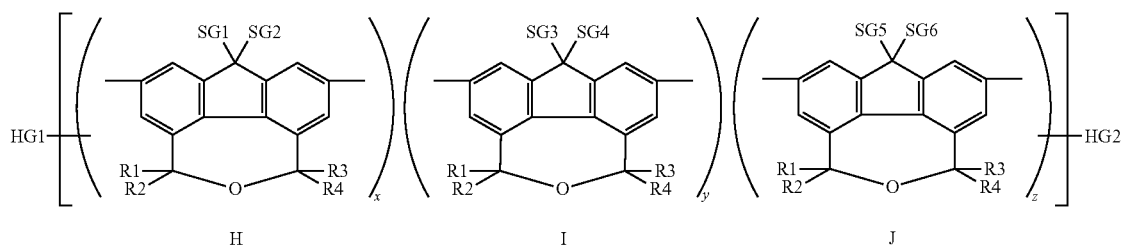

Formula III wherein the polymer conjugate comprises three monomer units represented by H, I and J that are randomly distributed along the polymer main chain;

wherein R1 to R4 independently represent hydrogen, an alkyl, a polyethyleneglycol (PEG), an aryl, a heteroaryl group, or a biological substrate (L-BS) conjugated via a linker;

wherein SG1 to SG6 independently represent an alkyl, a water soluble group or a L-BS;

wherein HG1 and HG2 independently represent a hydrogen, an aryl, a halogen or a boronyl, an aryl, a heteroaryl group, or a L-BS; and wherein x, y and z are each an integer independently selected from 0-100, provided that
(1) when a biological substrate is present at one or more locations within Formula III, the ratio of BS/polymer is 0.2-3, and
(2) the sum of x+y+z is >10.

In particular embodiments, according to all relevant aspects, the monomer units selected from H-J are directly connected to one another in any sequence of monomer units (as described elsewhere herein).

In particular embodiments, the linker comprises an alkyl, a PEG, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenylphosphonyl-benzoamide, an isoxazole or a succinimide group. In preferred embodiments, the linker comprises or is an alkyl or a PEG group. For embodiments which comprise multiple linkers, the linkers may be the same or different.

In preferred embodiments, R1 to R4 independently represent hydrogen, methyl, or ethyl; SG1 to SG6 independently represent a PEG, an alkyl, a carboxyalkyl, a sulfonylalkyl, a phosphonylalkyl, an aminoalkyl or L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl; and x, y and z are each an integer independently selected from 0-80, provided that (1) the ratio of BS/polymer is 1-2, and (2) the sum of x+y+z is >20.

In other preferred embodiments, R1 to R4 are hydrogen; SG1 and SG2 are PEG; SG3 to SG6 independently represent a PEG, an alkyl, a carboxyalkyl, a sulfonylalkyl, a phosphonylalkyl, an aminoalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl; and x, y and z are each an integer independently selected from 0-80, provided that (1) the ratio of BS/polymer is 1-2, and (2) the sum of x+y+z is >20.

In other preferred embodiments, R1 to R4 are hydrogen; SG1 and SG2 are PEG; SG3 to SG6 independently represent a PEG, an alkyl, a carboxyalkyl, a sulfonylalkyl, a phosphonylalkyl, or an aminoalkyl; HG1 and HG2 independently represent a hydrogen, an aryl, a halogen, boronyl, or a L-BS; L comprises or is an alkyl chain or a PEG chain; BS is an antibody, a peptide, a protein, an oligonucleotide, a nucleic acid or a carbohydrate; and x, y and z are each an integer independently selected from 0-80, provided that (1) the ratio of BS/polymer is 1-2, and (2) the sum of x+y+z is >20.

In other preferred embodiments, R1 to R4 are hydrogen; SG1 and SG2 are PEG; SG3 to SG6 independently represent a PEG, an alkyl, a carboxyalkyl, or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; and x, y and z are each an integer independently selected from 0-80, provided that (1) the ratio of BS/polymer is 1-2, and (2) the sum of x+y+z is >20.

In other preferred embodiments, R1 to R4 are hydrogen; SG1 and SG2 are PEG; SG3 to SG6 independently represent a PEG, an alkyl, a sulfonylalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; and x, y and z are each an integer independently selected from 0-80, provided that (1) the ratio of BS/polymer is 1-2, and (2) the sum of x+y+z is >20.

In other preferred embodiments, R1 to R4 are hydrogen; SG1 and SG2 are PEG; SG3 to SG6 independently represent a PEG, an alkyl, a phosphonylalkyl, or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; and x, y and z are each an integer independently selected from 0-80, provided that (1) the ratio of BS/polymer is 1-2, and (2) the sum of x+y+z is >20.

In other preferred embodiments, R1 to R4 are hydrogen; SG1 and SG2 are PEG; SG3 to SG6 independently represent a PEG, an alkyl, an aminoalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; and x, y and z are each an integer independently selected from 0-80, provided that (1) the ratio of BS/polymer is 1-2, and (2) the sum of x+y+z is >20.

In other preferred embodiments, R1 to R4 are hydrogen; SG1 and SG2 are PEG; SG3 to SG6 independently represent a PEG, an alkyl, a carboxyalkyl, or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; and x, y and z are each an integer independently selected from 0-80, provided that (1) the ratio of BS/polymer is 1, and (2) the sum of x+y+z is 30-80.

In other preferred embodiments, R1 to R4 are hydrogen; SG1 and SG2 are PEG; SG3 to SG6 independently represent a PEG, an alkyl, a sulfonylalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; and x, y and z are each an integer independently selected from 0-80, provided that (1) the ratio of BS/polymer is 1, and (2) the sum of x+y+z is 30-80.

In other preferred embodiments, R1 to R4 are hydrogen; SG1 and SG2 are PEG; SG3 to SG6 independently represent a PEG, an alkyl, a phosphonylalkyl, or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; and x, y and z are each an integer independently selected from 0-80, provided that (1) the ratio of BS/polymer is 1, and (2) the sum of x+y+z is 30-80.

In other preferred embodiments, R1 to R4 are hydrogen; SG1 and SG2 are PEG; SG3 to SG6 independently represent a PEG, an alkyl, an aminoalkyl or a L-BS; L comprises or is an alkyl chain or a PEG chain; BS is an antibody, a peptide, a protein, an oligonucleotide, a nucleic acid or a carbohydrate; HG1 and HG2 independently represent a hydrogen, an aryl, a halogen or a boronyl, or a L-BS; and x, y and z are each an integer independently selected from 0-80, provided that (1) the ratio of BS/polymer is 1, and (2) the sum of x+y+z is 30-80.

A preferred embodiment is a compound of Formula IV:

Formula IV

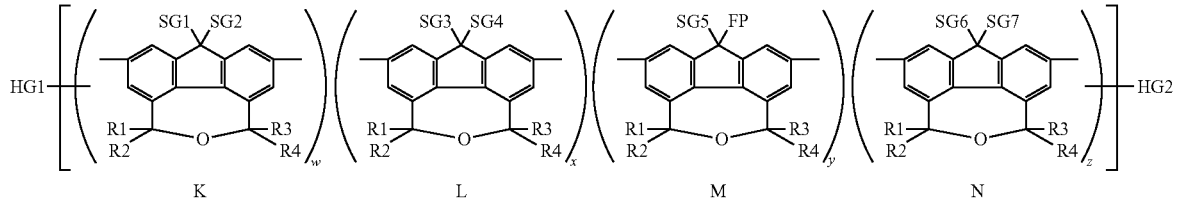

wherein the polymer conjugate comprises four monomer units represented by K, L, M and N that are randomly distributed along the polymer main chain;

wherein fluorophore (FP) is a fluorescent dye that has absorption maximum longer than 450 nm, and emission maximum longer than 500 nm with fluorescence quantum yield larger than 5%;

wherein R1 to R4 independently represent hydrogen, an alkyl, a PEG, an aryl, a heteroaryl group, or a L-BS (as defined herein);

wherein SG1 to SG7 independently represent an alkyl, a water soluble group or a L-BS;

wherein HG1 and HG2 independently represent an hydrogen, a halogen, a boronyl, an alkyl, an aryl, a heteroaryl group, or a L-BS;

wherein w, x and z are each an integer independently selected from 0-100; and wherein y is an integer from 1 to 20, provided that (1) when a biological substrate is present at one or more locations within Formula IV, the ratio of BS/polymer is 0.2-3, and (2) the sum of w+x+y+z is >10.

In particular embodiments, according to all relevant aspects, the monomer units selected from K-N are directly connected to one another in any sequence of monomer units (as described elsewhere herein).

In particular embodiments, the linker comprises an alkyl, a PEG, an FP, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenylphosphonyl-benzoamide, an isoxazole or a succinimide group. In preferred embodiments, the linker comprises or is an alkyl, a PEG group or a FP. For embodiments which comprise multiple linkers, the linkers may be the same or different.

The monomer units of the polymer conjugates of Formulae I-IV are randomly distributed along the polymer main chain. Thus, the monomer units can be found in any sequence throughout the polymer main chain. The monomer units may also, in particular embodiments be directly connected to one another. That is to say, using Formula I as an example, while the polymer main chain is depicted as a sequence of monomer units A-B-C (in the direction of the HG1 terminus to the HG2 terminus), this is for illustrative purposes only and the sequence of monomer units can be in any order. This is because a polymer according to the invention is, in actuality, entirely random with respect to the sequence of the component monomers (for example, a particular three monomer sequence may actually be something like A-B-C, A-C-B, C-B-A, C-A-B, B-A-C, B-C-A, etc. in the direction of the HG1 terminus to the HG2 terminus).

The position of the connection between each monomer and the main polymer chain is shown as a bond extending from the relevant monomer positions. Thus, if the connection is between two fluorene monomers (for example, monomers B and C of Formula I), then the connection is between the C7 of one monomer and the C2 of the other monomer. If the connection is between two fluoreno[4,5-cde]oxepine monomers (for example, monomers H and I of Formula III), then the connection is between the C2 of one monomer and the C8 of the other monomer. In the situation where a fluorene monomer is connected to a fluoreno[4,5-cde]oxepine monomer (for example, monomers D and E of Formula II), two types of connection are possible depending on the orientation of the monomer sequence relative to the HG1 to HG2 axis. In one orientation, the connection is made between the C8 of the fluoreno[4,5-cde]oxepine monomer to the C7 of the fluorene, for instance in the monomer sequence D-E (from HG1 terminus to HG2 terminus). Likewise, in the other orientation, the connection between the fluorene monomer and the fluoreno[4,5-cde]oxepine monomer would be between the C2 of the fluorene and the C2 of the fluoreno[4,5-cde]oxepine, for instance in the monomer sequence E-D (from HG1 terminus to HG2 terminus). For reference, the carbon numbers for the fluorene core structure and the fluoreno[4,5-cde]oxepine basic structure discussed here and throughout are provided in the Summary of the application. Direct connection between the monomers preserves a violet laser excitable functionality of the polymer conjugates.

In preferred embodiments, FP is a fluorescein, a rhodamine, a rhodol, a cyanine, a bodipy, a squaraine, a coumarin, a perylenediimide, a diketopyrrolopyrrole, a porphyrin or a phthalocyanine; R1 to R4 independently represent hydrogen, methyl, or ethyl; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; HG1 and HG2 independently represent a hydrogen, an aryl, a halogen or a boronyl; wherein w, x and z are each an integer independently selected from 0-80; and wherein y is an integer from 1 to 10, provided that (1) the ratio of BS/polymer is 1-2, and (2) the sum of w+x+y+z is >20.

In other preferred embodiments, FP is a fluorescein, a rhodamine, a rhodol, a cyanine, a bodipy, a squaraine, a coumarin, a perylenediimide, a diketopyrrolopyrrole, a porphyrin or a phthalocyanine; R1 to R4 independently represent hydrogen, methyl, or ethyl; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; wherein w, x and z are each an integer independently selected from 0-80; and wherein y is an integer from 1 to 10, provided that (1) the ratio of BS/polymer is 1-2, and (2) the sum of w+x+y+z is >20.

In other preferred embodiments, FP is a fluorescein, a rhodamine, a rhodol, a cyanine, a bodipy, a squaraine, a coumarin, a perylenediimide, a diketopyrrolopyrrole, a porphyrin or a phthalocyanine; R1 to R4 are hydrogen; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; HG1 and HG2 independently represent a hydrogen, an aryl, a halogen or a boronyl; w, x and z are each an integer independently selected from 0-80; and wherein y is an integer from 1 to 10, provided that (1) the ratio of BS/polymer is 1-2, and (2) the sum of w+x+y+z is >20.

In other preferred embodiments, FP is a fluorescein, a rhodamine, a rhodol, a cyanine, a bodipy, a squaraine, a coumarin, a perylenediimide, a diketopyrrolopyrrole, a porphyrin or a phthalocyanine; R1 to R4 are hydrogen; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; w, x and z are each an integer independently selected from 0-80; and wherein y is an integer from 1 to 10, provided that (1) the ratio of BS/polymer is 1-2, and (2) the sum of w+x+y+z is >20.

In other preferred embodiments, FP is a fluorescein, a rhodamine, a cyanine, a bodipy, a squaraine, a perylenediimide, a diketopyrrolopyrrole, or a phthalocyanine; R1 to R4 are hydrogen; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; HG1 and HG2 independently represent a hydrogen, an aryl, a halogen or a boronyl; w, x and z are each an integer independently selected from 0-80; and wherein y is an integer from 1 to 10, provided that (1) the ratio of BS/polymer is 1-2, and (2) the sum of w+x+y+z is >20.

In other preferred embodiments, FP is a fluorescein, a rhodamine, a cyanine, a bodipy, a squaraine, a coumarin, a perylenediimide, a diketopyrrolopyrrole, or a phthalocyanine; R1 to R4 are hydrogen; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; w, x and z are each an integer independently selected from 0-80; and wherein y is an integer from 1 to 10, provided that (1) the ratio of BS/polymer is 1-2, and (2) the sum of w+x+y+z is >20.

In other preferred embodiments, FP is a fluorescein, a rhodamine, a cyanine, a bodipy, a squaraine, a perylenediimide, a diketopyrrolopyrrole, or a phthalocyanine; R1 to R4 are hydrogen; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; HG1 and HG2 independently represent a hydrogen, an aryl, a halogen or a boronyl; w, x and z are each an integer independently selected from 0-80; and wherein y is an integer from 1 to 10, provided that (1) the ratio of BS/polymer is 1, and (2) the sum of w+x+y+z is 30-80.

In other preferred embodiment, FP is a fluorescein, a rhodamine, a cyanine, a bodipy, a squaraine, a coumarin, a perylenediimide, a diketopyrrolopyrrole, or a phthalocyanine; R1 to R4 are hydrogen; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; w, x and z are each an integer independently selected from 0-80; and wherein y is an integer from 1 to 10, provided that (1) the ratio of BS/polymer is 1, and (2) the sum of w+x+y+z is 30-80.

In other preferred embodiments, FP is a fluorescent dye selected from Table 1; R1 to R4 are hydrogen; SG1 to SG7 independently represent a PEG, an alkyl, a carboxyalkyl, a sulfonylalkyl, a phosphonylalkyl, an aminoalkyl or a L-BS; L comprises or is an alkyl chain, a FP or a PEG chain; BS is an antibody, a peptide, a protein, an oligonucleotide, a nucleic acid or a carbohydrate; HG1 and HG2 independently represent a hydrogen, an aryl, a halogen or a boronyl; w, x and z are each an integer independently selected from 0-80; and wherein y is an integer from 1 to 10, provided that (1) the ratio of BS/polymer is 1, and (2) the sum of w+x+y+z is 30-80.

In other preferred embodiments, FP is a fluorescent dye selected from Table 1; R1 to R4 are hydrogen; SG1 to SG7 independently represent a PEG, an alkyl, a carboxyalkyl, a sulfonylalkyl, a phosphonylalkyl, or an aminoalkyl; HG1 and HG2 independently represent a hydrogen, an aryl, a halogen, a boronyl, or a L-BS; L comprises or is an alkyl chain, a FP or a PEG chain; BS is an antibody, a peptide, a protein, an oligonucleotide, a nucleic acid or a carbohydrate; w, x and z are each an integer independently selected from 0-80; and wherein y is an integer from 1 to 10, provided that (1) the ratio of BS/polymer is 1, and (2) the sum of w+x+y+z is 30-80.

The fluorophore (FP) linked to the polymers of the invention is typically a fluorescent dye that has absorption maximum longer than 450 nm, and emission maximum longer than 500 nm with fluorescence quantum yield larger than 10%. They are typically selected from coumarins, fluoresceins, rhodamines, cyanines, bodipys or other polycyclic aromatics. Many of them are commercially available as selectively listed in Table 1 as some non-limiting examples.

TABLE 1

The typical fluorophores that can be linked to the PFO polymers

| Fluorophore | Absorption (nm) | Emission (nm) |
| --- | --- | --- |
| ATTO 465 | 453 | 508 |
| ATTO 488 | 501 | 523 |
| ATTO 495 | 495 | 527 |
| ATTO 514 | 511 | 533 |
| ATTO 532 | 532 | 553 |
| ATTO 550 | 554 | 576 |
| ATTO 565 | 563 | 592 |
| ATTO 590 | 594 | 624 |
| ATTO 594 | 601 | 627 |
| ATTO 610 | 615 | 634 |
| ATTO 620 | 619 | 643 |
| ATTO 633 | 629 | 657 |
| ATTO 647 | 645 | 669 |
| ATTO 647N | 644 | 669 |
| ATTO 655 | 663 | 684 |
| ATTO 665 | 663 | 684 |
| ATTO 680 | 680 | 700 |
| ATTO 700 | 700 | 719 |
| ATTO 725 | 729 | 752 |
| ATTO 740 | 740 | 764 |
| 5-carboxy-2,7-dichlorofluorescein | 504 | 529 |
| 5-Carboxyfluorescein (5-FAM) | 492 | 518 |
| 5-Carboxynapthofluorescein | 598 | 668 |
| 5-Carboxytetramethylrhodamine (5-TAMRA) | 542 | 568 |
| 5-FAM (5-Carboxyfluorescein) | 492 | 518 |
| 5-ROX | 578 | 604 |
| 6-TAMRA | 548 | 568 |
| 6-Carboxyrhodamine 6G | 518 | 543 |
| 6-CR6G | 518 | 543 |
| 6-JOE | 520 | 548 |
| 6-FAM | 494 | 517 |
| 6-ROX | 570 | 591 |
| Alexa Fluor 488 | 492 | 520 |
| Alexa Fluor 532 | 532 | 554 |
| Alexa Fluor 546 | 557 | 573 |
| Alexa Fluor 568 | 578 | 603 |
| Alexa Fluor 594 | 594 | 618 |
| Alexa Fluor 633 | 632 | 650 |
| Alexa Fluor 647 | 647 | 666 |
| Alexa Fluor 660 | 668 | 698 |
| Alexa Fluor 680 | 679 | 702 |
| Bodipy 492/515 | 490 | 515 |
| Bodipy 493/503 | 533 | 549 |
| Bodipy 500/510 | 509 | 515 |
| Bodipy 505/515 | 502 | 510 |
| Bodipy 530/550 | 528 | 547 |
| Bodipy 542/563 | 543 | 563 |
| Bodipy 558/568 | 558 | 569 |
| Bodipy 564/570 | 564 | 570 |
| Bodipy 576/589 | 579 | 590 |
| Bodipy 581/591 | 584 | 592 |
| Bodipy 630/650-X | 625 | 642 |
| Bodipy 650/665-X | 647 | 665 |
| Bodipy 665/676 | 605 | 676 |
| Bodipy F2 | 505 | 513 |
| Bodipy R6G | 528 | 547 |
| Bodipy TMR | 542 | 574 |
| Bodipy TR | 589 | 617 |
| CF 488A | 490 | 515 |
| CF 555 | 555 | 565 |
| CF 568 | 562 | 583 |
| CF 594ST | 593 | 614 |
| CF 633 | 630 | 650 |

TABLE 1-continued

The typical fluorophores that can be linked to the PFO polymers

| Fluorophore | Absorption (nm) | Emission (nm) |
|---|---|---|
| CF 640R | 642 | 662 |
| CF 647 | 650 | 665 |
| CF 660C | 667 | 685 |
| CF 680 | 681 | 698 |
| CF680R | 680 | 701 |
| CF 750 | 755 | 777 |
| CF 770 | 770 | 797 |
| CF 790 | 784 | 806 |
| CL-NERF | 504 | 540 |
| CMFDA | 494 | 520 |
| Cy2 | 489 | 506 |
| Cy3 | 554 | 568 |
| Cy3.5 | 581 | 598 |
| Cy5 | 649 | 666 |
| Cy5.5 | 675 | 695 |
| Cy7 | 743 | 767 |
| DDAO | 646 | 659 |
| DiA | 456 | 591 |
| DiD | 644 | 665 |
| DiI | 549 | 565 |
| DyLight 488 | 493 | 518 |
| DyLight 550 | 562 | 576 |
| DyLight 594 | 593 | 618 |
| DyLight 633 | 638 | 658 |
| DyLight 650 | 652 | 672 |
| DyLight 680 | 692 | 712 |
| DyLight 755 | 754 | 776 |
| DyLight 800 | 777 | 794 |
| DiO | 487 | 502 |
| DiR | 748 | 780 |
| DM-NERF | 497 | 540 |
| DsRed | 558 | 583 |
| DTAF | 494 | 520 |
| DY-490 | 491 | 515 |
| DY-495 | 494 | 521 |
| DY-505 | 507 | 528 |
| DY-530 | 533 | 554 |
| DY-547 | 558 | 573 |
| DY-548 | 558 | 572 |
| DY-549 | 562 | 577 |
| DY-549P1 | 563 | 578 |
| DY-550 | 562 | 577 |
| DY-554 | 544 | 570 |
| DY-555 | 547 | 573 |
| DY-556 | 548 | 574 |
| DY-560 | 560 | 578 |
| DY-590 | 581 | 600 |
| DY-591 | 581 | 598 |
| DY-594 | 594 | 615 |
| DY-605 | 600 | 624 |
| DY-610 | 610 | 632 |
| DY-615 | 623 | 643 |
| DY-630 | 638 | 658 |
| DY-631 | 637 | 657 |
| DY-632 | 636 | 658 |
| DY-633 | 638 | 658 |
| DY-634 | 636 | 657 |
| DY-635 | 648 | 670 |
| DY-636 | 647 | 670 |
| DY-647 | 653 | 673 |
| DY-648 | 655 | 676 |
| DY-649 | 656 | 670 |
| DY-649P1 | 654 | 672 |
| DY-650 | 656 | 676 |
| DY-651 | 655 | 677 |
| DY-652 | 653 | 676 |
| DY-654 | 653 | 677 |
| DY-675 | 675 | 699 |
| DY-676 | 675 | 699 |
| DY-677 | 674 | 698 |
| DY-678 | 674 | 694 |
| DY-679 | 679 | 698 |
| DY-679P1 | 679 | 697 |
| DY-680 | 691 | 709 |
| DY-681 | 692 | 709 |
| DY-682 | 692 | 709 |
| DY-700 | 707 | 728 |
| DY-701 | 709 | 730 |
| DY-703 | 705 | 721 |
| DY-704 | 706 | 721 |
| DY-730 | 734 | 755 |
| DY-731 | 736 | 755 |
| DY-732 | 735 | 756 |
| DY-734 | 733 | 755 |
| DY-749 | 759 | 780 |
| DY-750 | 751 | 774 |
| DY-751 | 752 | 772 |
| DY-752 | 750 | 771 |
| DY-754 | 748 | 771 |
| DY-776 | 772 | 787 |
| DY-777 | 770 | 788 |
| DY-778 | 767 | 787 |
| DY-780 | 783 | 799 |
| DY-781 | 784 | 796 |
| DY-782 | 785 | 794 |
| DY-800 | 777 | 791 |
| DY-831 | 844 | 875 |
| Eosin | 524 | 545 |
| Erythrosin | 529 | 555 |
| FITC | 490 | 520 |
| Fluo-3 | 506 | 520 |
| Fluo-4 | 494 | 516 |
| Fluor-Ruby | 555 | 582 |
| FluorX | 494 | 520 |
| FM 1-43 | 479 | 598 |
| FM 4-46 | 515 | 640 |
| iFluor 488 | 498 | 520 |
| iFluor 555 | 558 | 578 |
| iFluor 594 | 588 | 610 |
| iFluor 647 | 649 | 670 |
| iFluor 680 | 686 | 702 |
| iFluor 700 | 696 | 720 |
| iFluor 750 | 755 | 785 |
| iFluor 780 | 787 | 808 |
| Lyso Tracker Green | 504 | 511 |
| Lyso Tracker Yellow | 551 | 576 |
| Mitotracker Green | 490 | 516 |
| Mitotracker Orange | 551 | 576 |
| Mitotracker Red | 578 | 599 |
| NBD | 466 | 539 |
| Oregon Green 488 | 494 | 517 |
| Oregon Green 514 | 506 | 526 |
| PKH26 | 551 | 567 |
| PKH67 | 496 | 520 |
| Resorufin | 571 | 584 |
| RH 414 | 532 | 716 |
| Rhod-2 | 552 | 576 |
| Rhodamine | 550 | 573 |
| Rhodamine 110 | 496 | 520 |
| Rhodamine 123 | 507 | 529 |
| Rhodamine 6G | 525 | 555 |
| Rhodamine B | 540 | 625 |
| Rhodamine Green | 502 | 527 |
| Rhodamine Red | 570 | 590 |
| Rose Bengal | 525 | 550 |
| Spectrum Green | 497 | 538 |
| Spectrum Orange | 559 | 588 |
| Spectrum Red | 587 | 612 |
| SYTO 11 | 508 | 527 |
| SYTO 12 | 499 | 522 |
| SYTO 13 | 488 | 509 |
| SYTO 14 | 517 | 549 |
| SYTO 15 | 516 | 546 |
| SYTO 16 | 488 | 518 |
| SYTO 17 | 621 | 634 |
| SYTO 18 | 490 | 507 |
| SYTO 20 | 512 | 530 |
| SYTO 21 | 494 | 517 |
| SYTO 22 | 515 | 535 |
| SYTO 23 | 499 | 520 |

TABLE 1-continued

The typical fluorophores that can be linked to the PFO polymers

| Fluorophore | Absorption (nm) | Emission (nm) |
|---|---|---|
| SYTO 24 | 490 | 515 |
| SYTO 25 | 521 | 556 |
| SYTO 40 | 420 | 441 |
| SYTO 41 | 430 | 454 |
| SYTO 42 | 433 | 460 |
| SYTO 43 | 436 | 467 |
| SYTO 44 | 446 | 471 |
| SYTO 45 | 452 | 484 |
| SYTO 59 | 622 | 645 |
| SYTO 60 | 652 | 678 |
| SYTO 61 | 628 | 645 |
| SYTO 62 | 652 | 676 |
| SYTO 63 | 657 | 673 |
| SYTO 64 | 599 | 619 |
| SYTO 80 | 531 | 545 |
| SYTO 81 | 530 | 544 |
| SYTO 82 | 541 | 560 |
| SYTO 83 | 543 | 559 |
| SYTO 84 | 567 | 582 |
| SYTO 85 | 567 | 583 |
| SYTOX Blue | 445 | 470 |
| SYTOX Green | 504 | 523 |
| SYTOX Orange | 547 | 570 |
| Texas Red | 595 | 620 |
| Tide Fluor 2 (TF2) | 500 | 527 |
| Tide Fluor 2WS (TF2WS) | 502 | 525 |
| Tide Fluor 3 (TF3) | 555 | 584 |
| Tide Fluor 3WS(TF3WS) | 555 | 565 |
| Tide Fluor 4 (TF4) | 590 | 618 |
| Tide Fluor 5WS (TF5WS) | 649 | 664 |
| Tide Fluor 6WS (TF6WS) | 676 | 695 |
| Tide Fluor 7WS (TF7WS) | 749 | 775 |
| Tide Fluor 8WS (TF8WS) | 775 | 807 |
| TRITC | 550 | 573 |
| XTRITC | 582 | 601 |

In one aspect of the invention, alkylcarboxy is represented by Formula V:

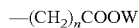
—(CH$_2$)$_n$COOW      Formula V

Wherein n is 1-20,
W is a hydrogen, an alkali metal ion, an ammonium or other biologically compatible counter ion.

In one aspect of the invention, alkylsulfonate is represented by Formula VI:

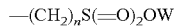
—(CH$_2$)$_n$S(=O)$_2$OW      Formula VI

Wherein n is 2-10,
W is a hydrogen, an alkali metal ion, an ammonium or other biologically compatible counter ion.

In one aspect of the invention, alkylphosphonate is represented by Formula VII:

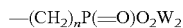
—(CH$_2$)$_n$P(=O)O$_2$W$_2$      Formula VII

Wherein n is 2-10,
W is a hydrogen, an alkali metal ion, an ammonium or other biologically compatible counter ion.

In one aspect of the invention, alkylammonium is represented by Formula VIII:

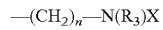
—(CH$_2$)$_n$—N(R$_3$)X      Formula VIII

Wherein n is 1-20,
R is a short alkyl (e.g. C$_1$-C$_{12}$ alkyl);
X is a biologically compatible anion such as F$^-$, Cl$^-$, Br$^-$ or I$^-$.

In one aspect of the invention, the linker L is represented by Formula IX:

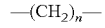
—(CH$_2$)$_n$—      Formula IX

Wherein n is 1-20.

In one aspect of the invention, the linker L is represented by Formula X:

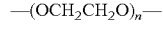
—(OCH$_2$CH$_2$O)$_n$—      Formula X

Wherein n is 2-20.

Many embodiments of the compounds of the invention possess an overall electronic charge. It is to be understood that when such electronic charges are shown to be present, they are balanced by the presence of appropriate counterions, which may or may not be explicitly identified. A biologically compatible counterion, which is preferred for some applications, is not toxic in biological applications, and does not have a substantially deleterious effect on biomolecules. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium or pyridinium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

It is to be understood that the polymer conjugates of the invention have been drawn in one or another particular electronic resonance structure. Every aspect of the instant invention applies equally to polymer conjugates that are formally drawn with other permitted resonance structures, as the electronic charge on the subject polymer conjugates is delocalized throughout the polymer conjugate itself.

In particular embodiments of the invention, the polymer conjugate contains at least one L-BS, to encompass L-FP-BS, where BS is attached to the polymer by any suitable reaction. According to the invention, BS is typically conjugated to the polymer via a covalent linkage. Some such well-known reactions are listed in Table 2 by way of example. In certain embodiments, the covalent linkage attaching the polymer to BS contains multiple intervening atoms that serve as a Linker (L). The linker may incorporate a FP in some embodiments, thus giving rise to L-FP-BS. The polymers can be used to label a wide variety of biological, organic or inorganic substances that contain or are modified to contain functional groups with suitable reactivity, resulting in chemical attachment of the conjugated substances.

TABLE 2

Examples of functional groups for preparing covalent linkages of L-BS or FP-BS

| Functional Group (FG) | Matching Functional Group | Resulting covalent linkages |
|---|---|---|
| activated esters | amines/anilines | carboxamides |
| acrylamides | thiols | thioethers |

TABLE 2-continued

Examples of functional groups for preparing covalent linkages of L-BS or FP-BS

| Functional Group (FG) | Matching Functional Group | Resulting covalent linkages |
| --- | --- | --- |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thioethers |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |
| azides | alkynes | 1,2,3-triazoles |
| 1,2,4,5-tetrazines | cyclooctynes | pyradazines |
| hydroxylamines | aldehydes/ketones | oxamines |
| hydrazines | aldehydes/ketones | hydrazones |
| cysteines | aldehydes/ketones | thiazolidines |
| aryl azides | methyl 2-diphenylphosphinobenzon | 2-diphenylphosphonyl-benzoamides |
| Nitrile-N- oxides | cycloalkynes | isoxazoles |
| anthracenes | maleimides | succinimides |

Choice of the linkage used to attach the polymer to a biological substrate to be conjugated typically depends on the functional group on the biological substrate to be conjugated and the type or length of covalent linkage desired. The types of functional groups typically present on the organic or inorganic biological substrates include, but are not limited to: amines, amides, thiols, alcohols, phenols, aldehydes, ketones, phosphonates, imidazoles, hydrazines, hydroxylamines, disubstituted amines, halides, epoxides, carboxylate esters, sulfonate esters, purines, pyrimidines, carboxylic acids, olefinic bonds, azide, alkyne, tetrazine or a combination of these groups. A single type of reactive site may be available on the biological substrate (typical for polysaccharides), or a variety of sites may occur (e.g. amines, thiols, alcohols, phenols, as is typical for proteins. A conjugated biological substrate may be conjugated to more than one polymer conjugate, which may be the same or different, or to a biological substrate that is additionally modified by a hapten, such as biotin. Alternatively multiple substrates might be conjugated to a single polymer. Although some selectivity can be obtained by careful control of the reaction conditions, selectivity of labeling is best obtained by selection of an appropriate reactive polymer conjugate.

Typically, the polymers of the invention will react with an amine, a thiol, an alcohol, an aldehyde or a ketone, contained for example as a substituent or part of the biological substrate. Preferably polymers of the invention are able to react with an amine, a thiol functional or a clickable group. In some embodiments, the functional group(s) of the polymer is an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, tetrazine, azide, alkyne or a thiol group. By "reactive platinum complex" is particularly meant chemically reactive platinum complexes such as described in U.S. Pat. Nos. 5,580,990; 5,714,327 and U.S. Pat. No. 5,985,566.

Where the functional group(s) of the polymer is a photoactivatable, such as an azide, diazirinyl, azidoaryl, or psoralen derivative, the polymer becomes chemically reactive only after illumination with light of an appropriate wavelength. Where the functional group(s) of the polymer is an activated ester of a carboxylic acid, the reactive polymer is particularly useful for preparing polymer conjugates of proteins, nucleotides, oligonucleotides, or haptens. Where the functional group(s) of the polymer is a maleimide or haloacetamide the reactive polymer is particularly useful for conjugation to thiol-containing biological substrates. Where the functional group(s) of the polymer is a hydrazide, the reactive polymer is particularly useful for conjugation to periodate-oxidized carbohydrates and glycoproteins, and in addition is an aldehyde-fixable polar tracer for cell microinjection. Where the functional group(s) of the polymer is clickable the reactive polymer is particularly useful for conjugation to the complimentary clickable substrate. Preferably, the functional group(s) of the polymer is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. More preferably, the functional group(s) of the polymer is a succinimidyl ester of a carboxylic acid, a maleimide, an iodoacetamide, or a reactive platinum complex.

Based on the above-mentioned attributes, the appropriate reactive polymers of the invention are selected for the preparation of the desired polymer conjugates, whose advantageous properties make them useful for a wide variety of applications. Particularly useful polymer conjugates include, among others, conjugates where the biological substrate is a peptide, a nucleotide, an antigen, a steroid, a vitamin, a drug, a hapten, a metabolite, a toxin, an environmental pollutant, an amino acid, a protein, a nucleic acid, a nucleic acid polymer (such as an oligonucleotide), a carbohydrate, a lipid or an ion-complexing moiety. Alternatively, the biological substrate is a cell, a cellular system, a cellular fragment, or a subcellular particle (e.g. inter alia), a virus particle, a bacterial particle, a virus component, a biological cell (such as animal cell, plant cell, bacteria, yeast, or protist), or a cellular component. Reactive polymers typically label functional groups at the cell surface, in cell membranes, organelles, or cytoplasm.

Typically the biological substrate is an amino acid, a peptide, a protein, a tyramine, a polysaccharide, an ion-complexing moiety, a nucleoside, a nucleotide, an oligonucleotide, a nucleic acid, a hapten, a psoralen, a drug, a hormone, a lipid, a lipid assembly, a polymer, a polymeric microparticle, a biological cell or virus. More typically, the biological substrate is a peptide, a protein, a nucleotide, an oligonucleotide, or a nucleic acid. When conjugating polymer conjugates of the invention to such biopolymers, it is possible to incorporate more polymers per molecule to increase the fluorescent signal. For polymer-antibody conjugates, one polymer/antibody is preferred.

In particular embodiments, the biological substrate is an amino acid (including those that are protected or are substituted by phosphonates, carbohydrates, or $C_1$ to $C_{25}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins, chemokines and growth factors. In one preferred aspect, the conjugated protein is a polymer antibody conjugate.

In one aspect of the invention, the conjugated biological substrate may be an antibody (including intact antibodies, antibody fragments, and antibody sera, etc.), an amino acid, an angiostatin or endostatin, an avidin or streptavidin, a biotin (e.g. an amidobiotin, a biocytin, a desthiobiotin, etc.), a blood component protein (e.g. an albumin, a fibrinogen, a plasminogen, etc.), a dextran, an enzyme, an enzyme inhibitor, an IgG-binding protein (e.g. a protein A, protein G, protein A/G, etc.), a fluorescent protein (e.g. a phycobiliprotein, an aequorin, a green fluorescent protein, etc.), a growth factor, a hormone, a lectin (e.g. a wheat germ agglutinin, a conconavalin A, etc.), a lipopolysaccharide, a metal-binding protein (e.g. a calmodulin, etc.), a microorganism or portion thereof (e.g. a bacteria, a virus, a yeast, etc.), a neuropeptide and other biologically active factors (e.g. a dermorphin, a deltropin, an endomorphin, an endorphin, a tumor necrosis factor etc.), a non-biological microparticle (e.g. of ferrofluid, gold, polystyrene, etc.), a nucleotide, an oligonucleotide, a peptide toxin (e.g. an apamin, a bungarotoxin, a phalloidin, etc.), a phospholipid-binding protein (e.g. an annexin, etc.), a small-molecule drug (e.g. a methotrexate, etc.), a structural protein (e.g. an actin, a fibronectin, a laminin, a microtubule-associated protein, a tublin, etc.), or a tyramide.

In another aspect, the biological substrate may be a nucleic acid base, nucleoside, nucleotide or a nucleic acid polymer, including those that are modified to possess an additional linker or spacer for attachment of the polymer conjugates of the invention, such as an alkynyl linkage (U.S. Pat. No. 5,047,519), an aminoallyl linkage (U.S. Pat. No. 4,711,955), or a heteroatom-substituted linker (U.S. Pat. No. 5,684,142) or other linkage. In other embodiments, the conjugated biological substrate is a nucleoside or nucleotide analog that links a purine or pyrimidine base to a phosphate or polyphosphate moiety through a noncyclic spacer. In other embodiments, the polymer conjugate is conjugated to the carbohydrate portion of a nucleotide or nucleoside, typically through a hydroxyl group but additionally through a thiol or amino group (U.S. Pat. Nos. 5,659,025; 5,668,268; 5,679,785). Typically, the conjugated nucleotide is a nucleoside triphosphate or a deoxynucleoside triphosphate or a dideoxynucleoside triphosphate. Incorporation of methylene moieties or nitrogen or sulfur heteroatoms into the phosphate or polyphosphate moiety is also useful. Nonpurine and nonpyrimidine bases such as 7-deazapurines (U.S. Pat. No. 6,150,510) and nucleic acids containing such bases can also be coupled to polymer conjugates of the invention. Nucleic acid adducts prepared by reaction of depurinated nucleic acids with amine, hydrazide or hydroxylamine derivatives provide an additional means of labeling and detecting nucleic acids, e.g. "A method for detecting abasic sites in living cells: age-dependent changes in base excision repair." Atamna H, Cheung I, Ames B N. PROC. NATL. ACAD. SCI. U.S.A. 97, 686-691 (2000).

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates, or peptide nucleic acids such as N-(2-aminoethyl)glycine units. When the nucleic acid is a synthetic oligonucleotide, it typically contains fewer than 50 nucleotides, more typically fewer than 25 nucleotides. Conjugates of peptide nucleic acids (PNA) (Nielsen, et al. U.S. Pat. No. 5,539,082), may be preferred for some applications because of their generally faster hybridization rates.

In particular embodiments, the conjugated oligonucleotides of the invention are aptamers for a particular target molecule, such as a metabolite, polymer conjugate, hapten, or protein. That is, the oligonucleotides have been selected to bind preferentially to the target molecule. Methods of preparing and screening aptamers for a given target molecule have been previously described and are known in the art [for example, U.S. Pat. No. 5,567,588 to Gold (1996)].

In other embodiments, the biological substrate is a carbohydrate that is typically a polysaccharide, such as a dextran, heparin, glycogen, amylopectin, mannan, inulin, starch, agarose and cellulose. Alternatively, the carbohydrate is a polysaccharide that is a lipopolysaccharide. Preferred polysaccharide conjugates are dextran, or lipopolysaccharide conjugates.

Conjugates having an ion-complexing moiety serve as indicators for calcium, sodium, magnesium, zinc, potassium, or other biologically important metal ions. Preferred ion-complexing moieties are crown ethers (U.S. Pat. No. 5,405,975); derivatives of 1,2-bis-(2-aminophenoxyethane)-N,N,N',N'-tetraacetic acid (BAPTA chelators; U.S. Pat. Nos. 5,453,517; 5,516,911 and 5,049,673); derivatives of 2-carboxymethoxyaniline-N,N-di-acetic acid (APTRA chelators; AM. J. PHYSIOL., 256, C540 (1989)); or pyridine- and phenanthroline-based metal ion chelators (U.S. Pat. No. 5,648,270); or derivatives of nitrilotriacetic acid, see e.g. "Single-step synthesis and characterization of biotinylated nitrilotriacetic acid, a unique reagent for the detection of histidine-tagged proteins immobilized on nitrocellulose", McMahan S A and Burgess R R, ANAL. BIOCHEM., 236, 101-106 (1996). Preferably, the ion-complexing moiety is a crown ether chelator, a BAPTA chelator, an APTRA chelator or a derivative of nitrilotriacetic acid.

In certain embodiments according to all aspects of the invention, when the biological substrate is a biological polymer such as a peptide, protein, oligonucleotide or nucleic acid polymer, the biological substrate is also labeled with at least a second fluorescent dye conjugate, which is optionally an additional polymer conjugate of the present invention, to form an energy-transfer pair. An energy transfer pair according to the present disclosure broadly includes light sensitive molecules, such as chromophores or fluorophores, capable of transferring energy between them. For example, a donor chromophore/fluorophore, may be excited by a first wavelength of light to its electronic excited state, and then may transfer energy to an acceptor chromophore/fluorophore, such as for example through nonradiative dipole-dipole coupling. One chromophore/fluorophore may absorb energy of a first wavelength, energy is transferred to the second chromophore/fluorophore, and energy emission from the second chromophore/fluorophore is at a second, different wavelength. The efficiency of the energy transfer is inversely proportional to the distance between the two chromophores/fluorophores. According to certain aspects, the first chromophore/fluorophore may be located on a first monomer of the polymer described herein and the second chromophore/fluorophore may be located on a second monomer of the polymer but close enough for the first and second chromophores/fluorophores to constitute an energy transfer pair. Alternatively, the first chromophore/fluorophore may be located on a first monomer of the polymer described herein and the second chromophore/fluorophore may be located at a position close enough to the first chromophore/fluorophore within the system for the first and second chromophores/fluorophores to constitute an energy transfer pair, that is, for energy to transfer from the first chromophore/fluorophore to the second chromophore/fluorophore. Alternatively, two members of an energy transfer pair may be parts of a fluorescent protein which may be connected or fused to other molecules. When the parts of the fluorescent protein are close enough to each other, they form a fluorophore.

In some aspects of the invention, the labeled conjugate or biological substrate functions as an enzyme substrate, and enzymatic hydrolysis disrupts the energy transfer. In this manner, disruption of energy transfer between an energy transfer pair and the resulting disruption of fluorescence serves to indicate the activity of a target enzyme which has the labeled conjugate or biological substrate as the enzyme substrate. Enzymes which can be used to degrade or otherwise interfere with biological substrates such as an amino acid, a peptide, a protein, a tyramine, a polysaccharide, an ion-complexing moiety, a nucleoside, a nucleotide, an oligonucleotide, a nucleic acid, a hapten, a psoralen, a drug, a hormone, a lipid, a lipid assembly, a polymer, a polymeric microparticle, a biological cell or virus are known to those of skill in the art. Thus, for example, hydrolysis probes (such as TAQMAN® probes) may rely on the 5'-3' exonuclease activity of a polymerase to disrupt quenching of a fluorescent donor moiety.

In other embodiments of the invention, the energy-transfer pair that incorporates a polymer conjugate of the invention is conjugated to an oligonucleotide that displays efficient fluorescence quenching in its hairpin conformation [the so-called "molecular beacons" of Tyagi, et al., NATURE BIOTECHNOLOGY, 16, 49 (1998)] or fluorescence energy transfer. The disruption of the fluorescence energy transfer by a biological process might be used for monitoring the biological process.

The preparation of polymer conjugates using reactive polymer conjugates is well documented, e.g. U.S. Pat. No. 8,158,444; U.S. Pat. No. 8,455,613; U.S. Pat. No. 8,354,239; U.S. Pat. No. 8,362,193; and U.S. Pat. No. 8,575,303 to Gaylord, et al.; also WO 2013/101902 to Chiu et al. The other biological applications of polyfluorene polymers have been well documented by Thomas III et al. (Chem. Rev. 2007, 107, 1339); Zhu et al (Chem. Rev. 2012, 112, 4687) and Zhu et al. (Chem. Soc. Rev., 2011, 40, 3509). Conjugates typically result from mixing appropriate reactive polymers and biological substrate to be conjugated in a suitable solvent in which both are soluble. The polymer conjugates of the invention are readily soluble in aqueous solutions, facilitating conjugation reactions with most biological materials. For those reactive polymer conjugates that are photoactivated, conjugation requires illumination of the reaction mixture to activate the reactive polymer conjugates.

Reactive Polymer Synthesis

Figure 3:
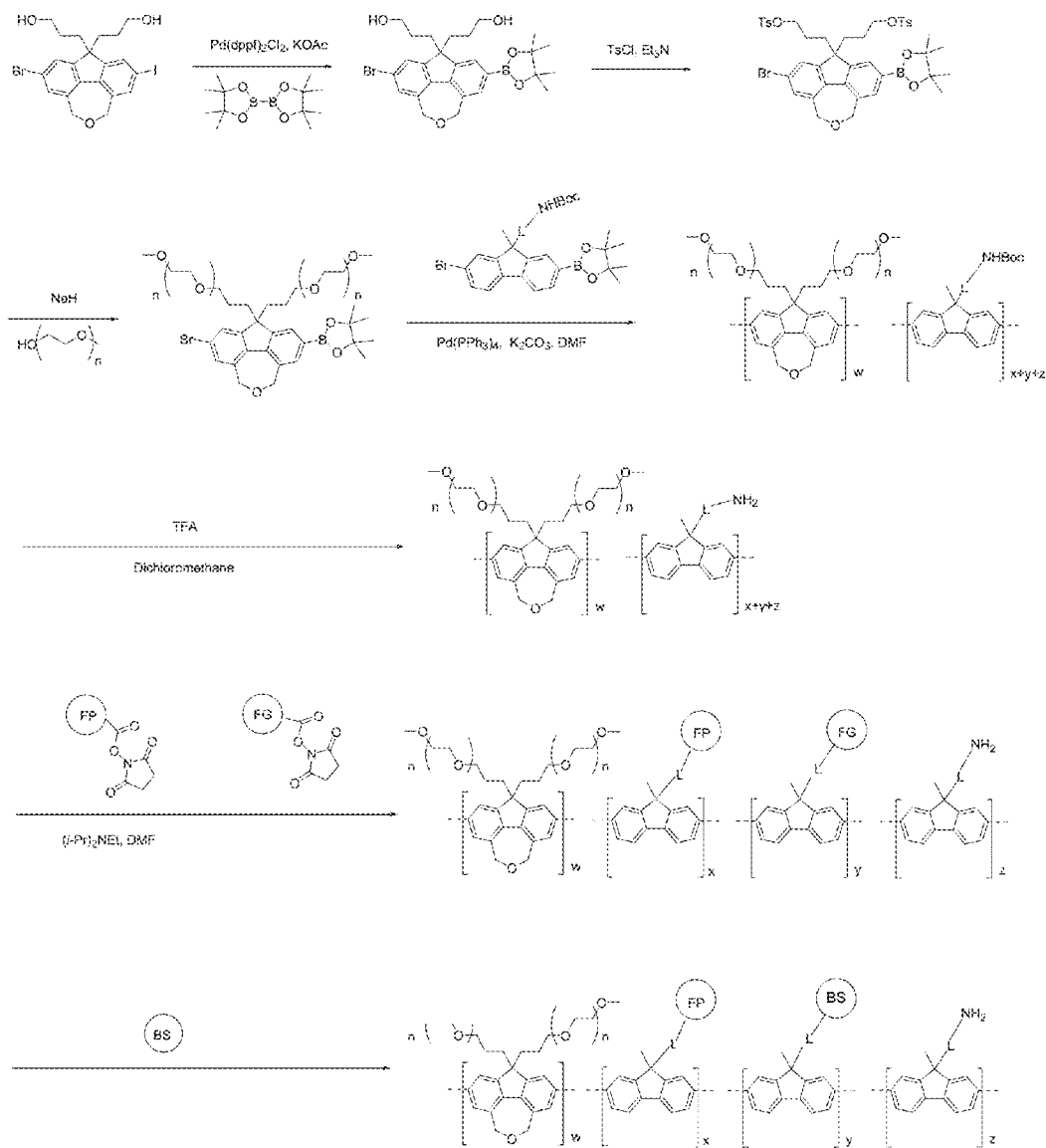
FIG. 3. A typical synthesis of polyfluoreno[4,5-cde]oxepine conjugates (See Examples 1-66). BS is a biological substrate. w, x, y and z represent the number of monomer units comprised within the main polymer conjugate chain. FG is a functional group used for conjugation as listed in Table 2. FP is a fluorophore as listed in Table 1. L is a linker.

Synthesis of the reactive polymers of the invention depends on initial preparation of certain key intermediates as illustrated in FIG. 3. For simplicity, all but a few of the possible substituents are shown as hydrogen. These basic structures are optionally further substituted, during or after synthesis, to give the corresponding polymer conjugate substituents as defined above. It is recognized that there are many possible variations that may yield equivalent results.

The methods for the synthesis of polymers that contain a variety of reactive functional groups such as those described in Table 2 are well documented in the art. Particularly useful are amine-reactive polymer conjugates such as "activated esters" of carboxylic acids, which are typically synthesized by coupling a carboxylic acid to a relatively acidic "leaving group". Other preferred amine-reactive groups include sulfonyl halides, which are prepared from sulfonic acids using a halogenating agent such as $PCl_5$ or $POCl_3$; halotriazines, which are prepared by the reaction of cyanuric halides with amines; and isocyanates or isothiocyanates, which are prepared from amines and phosgene or thiophosgene, respectively. Polymers containing azide, alkyne and tetrazine are particularly useful for conjugation to click group-modified substrates such as the antibodies modified by a click group-containing activated esters.

Polymers containing amines and hydrazides are particularly useful for conjugation to carboxylic acids, aldehydes and ketones. Most often these are synthesized by reaction of an activated ester of a carboxylic acid or a sulfonyl halide with a diamine, such as cadaverine, or with a hydrazine. Alternatively, aromatic amines are commonly synthesized by chemical reduction of a nitroaromatic compound. Amines and hydrazines are particularly useful precursors for synthesis of thiol-reactive haloacetamides or maleimides by standard methods.

Applications and Methods of Use

In one application, the polymer conjugates of the invention are used to directly stain or label a sample so that the sample can be identified or quantitated. Such uses may be in vitro applications. For instance, such polymer conjugates may be added as part of an assay for a biological target analyte, as a detectable tracer element in a biological or non-biological fluid; or for such purposes as photodynamic therapy of tumors, in which a polymer conjugated sample is irradiated to selectively destroy tumor cells and tissues; or to photoablate arterial plaque or cells, usually through the photosensitized production of singlet oxygen. In one preferred embodiment, the polymer conjugate is used to stain a sample that comprises a ligand for which the conjugated biological substrate is a complementary member of a specific binding pair. Representative binding pairs useful according to the invention are set forth in Table 3.

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

TABLE 3

Representative specific binding pairs

| Antigen | Antibody |
|---|---|
| Biotin | Anti-biotin or avidin or streptavidin or neutravidin |
| IgG* | Protein A or protein G or anti-IgG antibody |
| Drug | Drug receptor |
| Toxin | Toxin receptor |
| Carbohydrate | Lectin or carbohydrate receptor |
| Peptide | Peptide receptor |
| Nucleotide | Complimentary nucleotide |
| Protein | Protein receptor |
| Enzyme substrate | Enzyme |
| DNA (RNA) | aDNA (aRNA)** |
| Hormone | Hormone receptor |
| Psoralen | Nucleic acid |
| Target molecule | RNA or DNA aptamer |
| Ion | Ion chelator |

*IgG is an immunoglobulin;
**aDNA and aRNA are the antisense (complementary) strands used for hybridization In yet other embodiments, the sample may be present on or in solid or semi-solid matrix. In one aspect of the invention, the matrix is a membrane. In another aspect, the matrix is an electrophoretic gel, such as is used for separating and characterizing nucleic acids or proteins, or is a blot prepared by transfer from an electrophoretic gel to a membrane. In another aspect, the matrix is a silicon chip or glass slide, and the analyte of interest has been immobilized on the chip or slide in an array (e.g. the sample comprises proteins or nucleic acid polymers in a microarray). In yet another aspect, the matrix is a microwell plate or microfluidic chip, and the sample is analyzed by automated methods, typically by various methods of high-throughput screening, such as drug screening.

The polymer conjugates of the invention are generally utilized by combining a polymer conjugate of the invention as described above with the sample of interest under conditions selected to yield a detectable optical response. The term "polymer conjugate" is used herein to refer to all aspects of the claimed polymer conjugates. The polymer conjugate typically forms a covalent association or complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard or expected response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

For biological applications, the polymer conjugates of the invention are typically used in an aqueous, mostly aqueous or aqueous-miscible solution prepared according to methods generally known in the art. The exact concentration of polymer conjugate is dependent upon the experimental conditions and the desired results. The optimal concentration is determined by systematic variation until satisfactory results with minimal background fluorescence are accomplished.

The polymer conjugates are most advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acids, nucleic acids or carbohydrate polymers, or lipid membrane complexes). These polymer conjugates are generally non-toxic to living cells and other biological components, within the concentrations of use.

The polymer conjugate is combined with the sample in any way that facilitates contact between the polymer conjugate and the sample components of interest. Typically, the polymer conjugate or a solution containing the polymer conjugate is simply added to the sample. Certain polymer conjugates of the invention tend to be impermeant to membranes of biological cells, and once inside viable cells are typically well retained. Treatments that permeabilize the plasma membrane, such as electroporation, shock treatments or high extracellular ATP can be used to introduce selected polymer conjugates into cells. Alternatively, selected polymer conjugates can be physically inserted into cells, e.g. by pressure microinjection, scrape loading, patch clamp methods, or phagocytosis.

Polymer conjugates that incorporate an aliphatic amine or a hydrazine residue can be microinjected into cells, where they can be fixed in place by aldehyde fixatives such as formaldehyde or glutaraldehyde. This fixability makes such polymer conjugates useful for intracellular applications such as neuronal tracing.

Polymer conjugates that possess a lipophilic substituent, such as phospholipids, will non-covalently incorporate into lipid assemblies, e.g. for use as probes for membrane structure; or for incorporation in liposomes, lipoproteins, films, plastics, lipophilic microspheres or similar materials; or for tracing. Lipophilic polymer conjugates are useful as fluorescent probes of membrane structure.

Using polymer conjugates to label active sites on the surface of cells, in cell membranes or in intracellular compartments such as organelles, or in the cell's cytoplasm, permits the determination of their presence or quantity, accessibility, or their spatial and temporal distribution in the sample. Photoreactive polymer conjugates can be used similarly to photolabel components of the outer membrane of biological cells or as photo-fixable polar tracers for cells.

Optionally, the sample is washed after staining to remove residual, excess or unbound polymer conjugate. The sample is optionally combined with one or more other solutions in the course of staining, including wash solutions, permeabilization and/or fixation solutions, and solutions containing additional detection reagents. An additional detection reagent typically produces a detectable response due to the presence of a specific cell component, intracellular biological substrate, or cellular condition, according to methods generally known in the art. Where the additional detection reagent has, or yields a product with, spectral properties that differ from those of the subject polymer conjugates, multi-color applications are possible. This is particularly useful where the additional detection reagent is a polymer conjugate or polymer conjugate-conjugate of the present invention having spectral properties that are detectably distinct from those of the staining polymer conjugate.

The polymer conjugates of the invention are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. No. 5,332,666 to Prober, et al. (1994); U.S. Pat. No. 5,171,534 to Smith, et al. (1992); U.S. Pat. No. 4,997,928 to Hobbs (1991); and WO Appl. 94/05688 to Menchen, et al.). Conjugates comprising multiple independent polymer conjugates of the invention possess utility for multi-color applications.

At any time after or during staining, the sample is illuminated with a wavelength of light selected to give a detectable optical response, and observed with a means for detecting the optical response. Equipment that is useful for illuminating the polymer conjugates of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred embodiments of the invention are polymer conjugates that are excitable at or near the wavelength of 405 nm.

The optical response is optionally detected by visual inspection, or by use of any of the following devices: CCD cameras, video cameras, photographic films, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

One aspect of the instant invention is the formulation of kits that facilitate the practice of various assays using any of the polymer conjugates of the invention, as described above. The kits of the invention typically comprise a fluorescent polymer conjugate of the invention where the conjugated biological substrate is a specific binding pair member, or a nucleoside, a nucleotide, an oligonucleotide, a nucleic acid polymer, a peptide, or a protein. In other embodiments, the kits comprise unconjugated polymer and the biological substrate for conjugation thereto. After conjugation, the fluorescent polymer conjugate created is a polymer conjugate of the invention as described herein. The kits optionally further comprise one or more buffering agents, typically present as an aqueous solution. The kits of the invention optionally further comprise additional detection reagents, a purification medium for purifying the resulting labeled biological substrate, luminescence standards, enzymes, enzyme inhibitors, organic solvent, and/or instructions for carrying out an assay of the invention.

EXAMPLES

Examples of some synthetic strategies for selected polymer conjugates of the invention, as well as their characterization, synthetic precursors, conjugates and method of use are provided in the examples below. Further modifications and permutations will be obvious to one skilled in the art. The examples below are given so as to illustrate the practice of this invention. They are not intended to limit or define the entire scope of this invention. It is to be understood that this invention is not limited to particular aspects described, as such may vary. It is also to be understood that the terminology used herein is for the purpose of describing particular aspects only, and is not intended to be limiting since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Example 1. The preparation of 3,3'-(2-bromo-6-(4,4,5,5-tetramethyl-1,3,2-dioxaborolan-2-yl)-8,10-dihydro-4H-fluoreno[4,5-cde]oxepine-4,4-diyl)bis(propan-1-ol) (Compound 2)

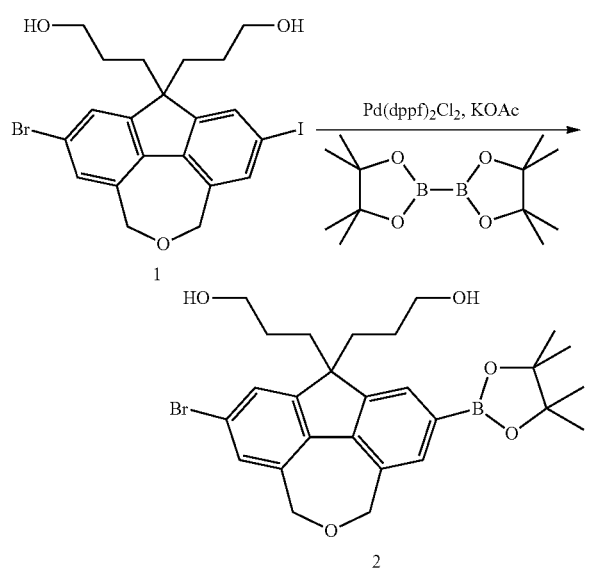

Under the argon, to the solution of 3-[2-Bromo-4-(3-hydroxypropyl)-6-iodo-8,10-dihydro-4H-9-oxacyclohepta[def]fluoren-4-yl]-propan-1-ol (Compound 1) (3 g, 5.67 mmol) in DMF (30 mL) solution, bis (pinacolato)diboron (2 g, 8 mmol), Pd(dppf)Cl$_2$ (0.2 g, 0.28 mmol) and potassium acetate (2.23 g, 22.7 mmol) were added. The mixture was heated at 60° C. for 2 hours. At room temperature, ethyl acetate (200 mL) was added and washed by water (100 mL), brine (100 mL). The organic layer was dried over anhydrous sodium sulfate and filtered. The solvent was removed and the crude product was purified by column chromatography (hexane-ethyl acetate) to give light brown foam (1.5 g, 50%).

Example 2. The preparation of (2-bromo-6-(4,4,5,5-tetramethyl-1,3,2-dioxaborolan-2-yl)-8,10-dihydro-4H-fluoreno[4,5-cde]oxepine-4,4-diyl)bis(propane-3,1-diyl) bis(4-methylbenzenesulfonate) (Compound 3)

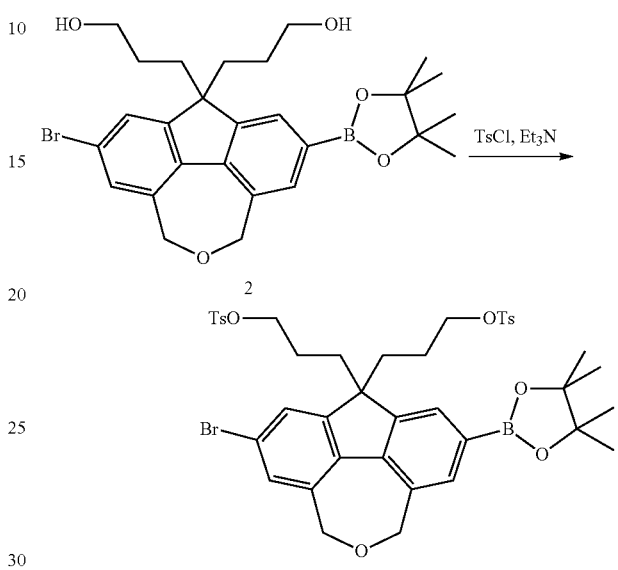

At room temperature under the argon, to the solution of compound 2 (5.84 g, 11 mmol) in dichloromethane (20 mL), triethylamine (9.2 mL, 66 mmol) was added, followed by p-toluenesulfonyl chloride (6.3 g, 33 mmol). The mixture was stirred at room temperature overnight. The mixture was concentrated. Ethyl acetate (200 mL) was added and washed by water (200 mL), brine (100 mL). The organic layer was dried over anhydrous sodium sulfate and filtered. The solvent was removed and the crude product was purified by column chromatography (hexane-ethyl acetate) to give white solid (5.2 g, 70%).

Example 3. The preparation of 2-(6-bromo-4,4-di(2,5,8,11,14,17,20,23,26,29,32,35-dodecaoxaoctatriacontan-38-yl)-8,10-dihydro-4H-fluoreno[4,5-cde]oxepin-2-yl)-4,4,5,5-tetramethyl-1,3,2-dioxaborolane (Compound 4)

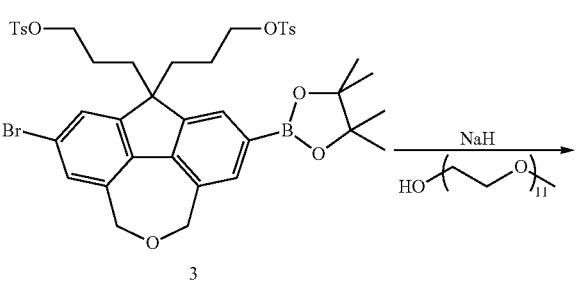

-continued

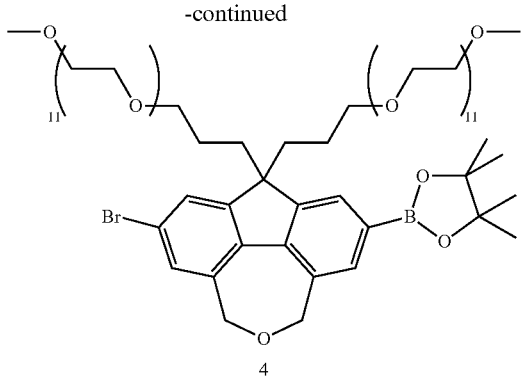

4

Under the argon, at 0° C., to the mixture of sodium hydride (0.24 g, 5.95 mmol) in dry THF (20 mL), mPEG11 alcohol (3.08 g, 5.95 mmol) was added. After 10 min at 0° C., the solution of compound 3 (1 g, 1.19 mmol) in dry THF (20 mL) was added dropwise. The mixture was stirred at room temperature overnight. Saturated ammonium chloride solution (100 mL) was added to quench the solution and the crude product was extracted with dichloromethane (2×100 mL). The combined organic layer was concentrated and purified by column chromatography with a gradient of dichloromethane/isopropyl alcohol to give colorless oil (1.0 g, 55%).

Example 4. The Preparation of Asymmetric PFO Polymer (Compound 7)

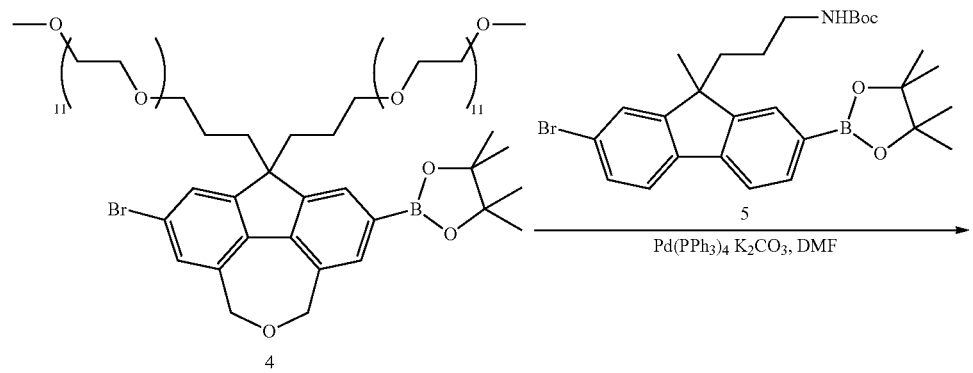

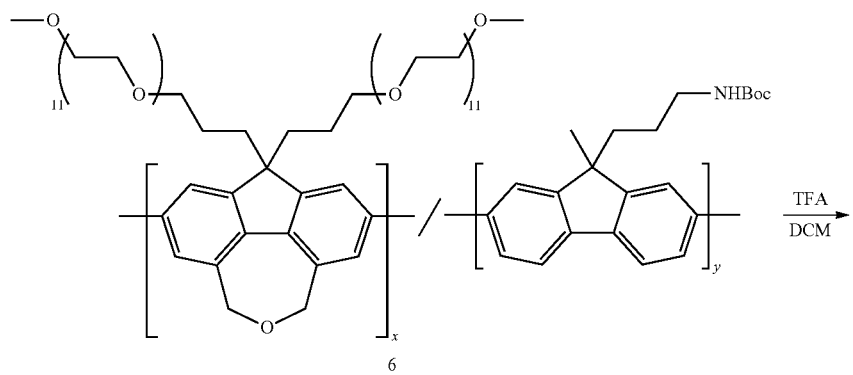

6

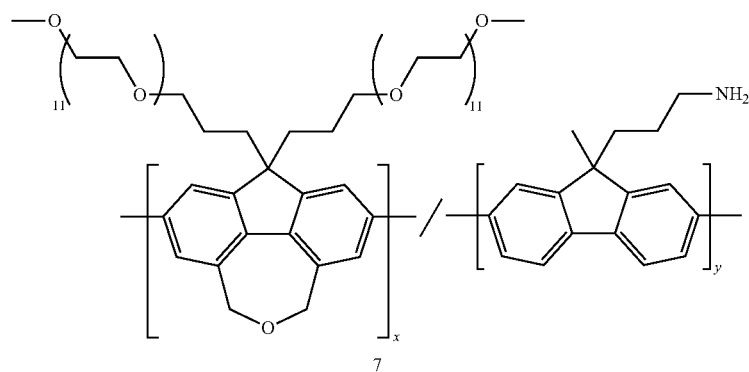

7

Under the argon, to the solution of Compound 4 (0.6 g, 0.4 mmol) and Compound 5 (0.023 g, 0.04 mmol) in DMF (6 mL) in a Schlenk flask, $K_2CO_3$ in water (2 M, 4 mL) was added, followed by palladium tetrakis(triphenylphosphine) (14 mg, 0.012 mol). The mixture was degassed via three freeze-pump-thaw cycles and then heated to 80° C. for 12 hours. At room temperature, to the reaction mixture EDTA (100 mg, 0.33 mmol) in 20% $EtOH/H_2O$ (20 mL) was added and stirred at room temperature for 1 hour. The resulting mixture was then filtered through a 0.45 m cup filter. The filtered solution was diluted to the concentration of 2 mg/mL using 20% $EtOH/H_2O$. The resulting dilution was then dialyzed into 20% $EtOH/H_2O$ using a tangential flow filtration system with 30,000 kD molecular weight cutoff membrane until there was less than 0.1 mg/mL of polymer in the elutant. The solution was concentrated and lyophilized to give a yellow, fibrous solid (0.41 g). Molecular weight was determined by SEC analysis relative to polystyrene standard (MW=85,000, MW=170,000, D=2.0). At room temperature, to the solution of Compound 6 (410 mg) in dichloromethane (20 ml), trifluoroacetic acid (5 mL) was added. The reaction mixture was stirred at room temperature for 2 hours. The solvent was removed and dried under high vacuum overnight to give pale yellow oil.

Example 5. The Preparation of Asymmetric PFO Polymer Succinimidyl Ester (Compound 8)

To the solution of Compound 7 (100 mg) in DMF (10 ml) was added 0.1 ml DMF solution of di(N-succinimidyl) glutarate (1 mg, AAT Bioquest) and 10 µl triethylamine. The reaction mixture was stirred at room temperature for 2 hours, and concentrated under high vacuum to remove DMF. The residue was washed with ether for multiple times until most of the unreacted di(N-succinimidyl) glutarate was removed. The residue was quickly dissolved in cold acidic water (pH=5), and extracted with ether for three times. The aqueous solution was frozen and dried to give the desired asymmetric PFO polymer succinimidyl ester.

Example 6. The Preparation of Asymmetric PFO Polymer Maleimide (Compound 9)

To the solution of Compound 7 (100 mg) in DMF (10 ml) was added 0.1 ml DMF solution of 3-maleimidopropionic acid N-hydroxysuccinimide ester (1 mg, AAT Bioquest) and 10 µl triethylamine. The reaction mixture was stirred at room temperature for 2 hours, and concentrated under high vacuum to remove DMF. The residue was dissolved in acidic water (pH=5), and extracted with ethyl acetate for three times. The aqueous solution was frozen and dried to give the desired asymmetric PFO polymer maleimide.

Example 7. The Preparation of Asymmetric PFO Polymer Dichlorotriazine (Compound 10)

To the solution of Compound 7 (100 mg) in DMF (10 ml) was added 0.1 ml DMF solution of cyanuric chloride (1 mg, Sigma) and 10 µl triethylamine. The reaction mixture was stirred at room temperature for 3 hours, and concentrated under high vacuum to remove DMF. The residue was washed with ethyl acetate for multiple times until most of the unreacted cyanuric chloride was removed. The residue was quickly dissolved in cold water (pH=6), and extracted with ethyl acetate for three times. The aqueous solution was frozen and dried to give the desired asymmetric PFO polymer dichlorotriazine.

Example 8. The Preparation of Asymmetric PFO Polymer DBCO (Compound 11)

To the solution of Compound 7 (100 mg) in DMF (10 ml) was added 0.1 ml DMF solution of DBCO-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted DBCO-PEG4 succinimidyl ester was removed. The residue was dissolved in water, and extracted with ethyl acetate for three times. The aqueous solution was frozen and dried to give the desired asymmetric PFO polymer DBCO.

Example 9. The preparation of asymmetric PFO polymer TCO (Compound 12)

To the solution of Compound 7 (100 mg) in DMF (10 ml) was added 0.1 ml DMF solution of TCO-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted TCO-PEG4 succinimidyl ester was removed. The residue was dissolved in water, and extracted with ethyl acetate for three times. The aqueous solution was frozen and dried to give the desired asymmetric PFO polymer TCO.

Example 10. The Preparation of Asymmetric PFO Polymer Methyltetrazine (Compound 13)

To the solution of Compound 7 (100 mg) in DMF (10 ml) was added 0.1 ml DMF solution of methyltetrazine-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted methyltetrazine-PEG4 succinimidyl ester was removed. The residue was dissolved in water, and extracted with ethyl acetate for three times. The aqueous solution was frozen and dried to give the desired asymmetric PFO polymer methyltetrazine.

Example 11. The Preparation of Asymmetric PFO Polymer Azide (Compound 14)

To the solution of Compound 7 (100 mg) in DMF (10 ml) was added 0.1 ml DMF solution of azido-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted azido-PEG4 succinimidyl ester was removed. The residue was dissolved in water, and extracted with ethyl acetate for three times. The aqueous solution was frozen and dried to give the desired asymmetric PFO polymer azide.

Example 12. The Preparation of Asymmetric PFO Polymer Alkyne (Compound 15)

To the solution of Compound 7 (100 mg) in DMF (10 ml) was added 0.1 ml DMF solution of alkynyl-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted alkynyl-PEG4 succinimidyl ester was removed. The residue was dissolved in water, and extracted with ethyl acetate for three times. The aqueous solution was frozen and dried to give the desired asymmetric PFO polymer alkyne.

Example 13. The Preparation of Asymmetric Cy3.5 Labeled PFO Polymer (Compound 16)

To the solution of Compound 7 (100 mg) in DMF (10 ml) was added 1 ml DMF solution of Cy3.5 monosuccinimidyl ester (10 mg, AAT Bioquest) and 20 µl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 14. The Preparation of Asymmetric Cy3.5 Labeled PFO Polymer DBCO (Compound 17)

To the solution of Compound 16 (100 mg) in DMF (10 ml) was added 0.1 ml DMF solution of DBCO-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted DBCO-PEG4 succinimidyl ester was removed. The residue was dissolved in water, and extracted with ethyl acetate for three times. The aqueous solution was frozen and dried to give the desired asymmetric PFO polymer DBCO.

Example 15. The Preparation of Asymmetric Cy3.5 Labeled PFO Polymer TCO (Compound 18)

To the solution of Compound 16 (100 mg) in DMF (10 ml) was added 0.1 ml DMF solution of TCO-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted TCO-PEG4 succinimidyl ester was removed. The residue was dissolved in water, and extracted with ethyl acetate for three times. The aqueous solution was frozen and dried to give the desired asymmetric PFO polymer TCO.

Example 16. The Preparation of Asymmetric Cy3.5 Labeled PFO Polymer Methyltetrazine (Compound 19)

To the solution of Compound 16 (100 mg) in DMF (10 ml) was added 0.1 ml DMF solution of methyltetrazine-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted methyltetrazine-PEG4 succinimidyl ester was removed. The residue was dissolved in water, and extracted with ethyl acetate for three times. The aqueous solution was frozen and dried to give the desired asymmetric PFO polymer methyltetrazine.

Example 17. The Preparation of Asymmetric Cy3.5 Labeled PFO Polymer Azide (Compound 20)

To the solution of Compound 16 (100 mg) in DMF (10 ml) was added 0.1 ml DMF solution of azido-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted azido-PEG4 succinimidyl ester was removed. The residue was dissolved in water, and extracted with ethyl acetate for three times. The aqueous solution was frozen and dried to give the desired asymmetric PFO polymer azide.

Example 18. The Preparation of Asymmetric Cy3.5 Labeled PFO Polymer Alkyne (Compound 21)

To the solution of Compound 16 (100 mg) in DMF (10 ml) was added 0.1 ml DMF solution of alkynyl-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted alkynyl-PEG4 succinimidyl ester was removed. The residue was dissolved in water, and extracted with ethyl acetate for three times. The aqueous solution was frozen and dried to give the desired asymmetric PFO polymer alkyne.

Example 19. The Preparation of Asymmetric Cy3.5 Labeled PFO Polymer Succinimidyl Ester (Compound 22)

To the solution of Compound 16 (100 mg) in DMF (10 ml) was added 0.1 ml DMF solution of di(N-succinimidyl) glutarate (1 mg, AAT Bioquest) and 10 µl triethylamine. The reaction mixture was stirred at room temperature for 2 hours, and concentrated under high vacuum to remove DMF. The residue was washed with ether for multiple times until most of the unreacted di(N-succinimidyl) glutarate was removed. The residue was quickly dissolved in cold water (pH=6), and extracted with ether for three times. The aqueous solution was frozen and dried to give the desired asymmetric PFO polymer succinimidyl ester.

Example 20. The Preparation of Asymmetric Cy3.5 Labeled PFO Polymer Maleimide (Compound 23)

To the solution of Compound 16 (100 mg) in DMF (10 ml) was added 0.1 ml DMF solution of 3-maleimidopropionic acid N-hydroxysuccinimide ester (1 mg, AAT Bioquest) and 10 µl triethylamine. The reaction mixture was stirred at room temperature for 2 hours, and concentrated under high vacuum to remove DMF. The residue was dissolved in water (pH=6), and extracted with ethyl acetate for three times. The aqueous solution was frozen and dried to give the desired asymmetric PFO polymer maleimide.

Example 21. The Preparation of Asymmetric Cy3.5 Labeled PFO Polymer Dichlorotriazine (Compound 24)

To the solution of Compound 16 (100 mg) in DMF (10 ml) was added 0.1 ml DMF solution of cyanuric chloride (1 mg, Sigma) and 10 μl triethylamine. The reaction mixture was stirred at room temperature for 3 hours, and concentrated under high vacuum to remove DMF. The residue was washed with ethyl acetate for multiple times until most of the unreacted cyanuric chloride was removed. The residue was quickly dissolved in cold water (pH=6), and extracted with ethyl acetate for three times. The aqueous solution was frozen and dried to give the desired asymmetric PFO polymer dichlorotriazine.

Example 22. The Preparation of Asymmetric Cy5 Labeled PFO Polymer DBCO (Compound 25)

To the solution of Compound 16 (100 mg) in DMF (10 ml) was added 0.1 ml DMF solution of DBCO-PEG4 Cy5 monosuccinimidyl ester (1 mg, AAT Bioquest) and 10 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 23. The Preparation of Asymmetric Cy5 Labeled PFO Polymer TCO (Compound 26)

To the solution of Compound 16 (100 mg) in DMF (10 ml) was added 0.1 ml DMF solution of TCO-PEG4 Cy5 monosuccinimidyl ester (1 mg, AAT Bioquest) and 10 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 24. The Preparation of Asymmetric Cy5 Labeled PFO Polymer Methyltetrazine (Compound 27)

To the solution of Compound 16 (100 mg) in DMF (10 ml) was added 0.1 ml DMF solution of methyltetrazine-PEG4 Cy5 monosuccinimidyl ester (1 mg, AAT Bioquest) and 20 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 25. The Preparation of Asymmetric Cy5 Labeled PFO Polymer Azide (Compound 28)

To the solution of Compound 27 (100 mg) in DMF (10 ml) was added 0.1 ml DMF solution of azido-PEG4 succinimidyl ester (1 mg, AAT Bioquest) and 10 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 26. The Preparation of Asymmetric Cy5 Labeled PFO Polymer (Compound 29)

To the solution of Compound 7 (100 mg) in DMF (10 ml) was added 1 ml DMF solution of Cy5 monosuccinimidyl ester (10 mg, AAT Bioquest) and 10 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 27. The Preparation of Asymmetric Cy5 Labeled PFO Polymer Succinimidyl Ester (Compound 30)

To the solution of Compound 29 (100 mg) in DMF (10 ml) was added 0.1 ml DMF solution of di(N-succinimidyl) glutarate (1 mg, AAT Bioquest) and 10 μl triethylamine. The reaction mixture was stirred at room temperature for 2 hours, and concentrated under high vacuum to remove DMF. The residue was washed with ether for multiple times until most of the unreacted di(N-succinimidyl) glutarate was removed. The residue was quickly dissolved in cold water (pH=6), and extracted with ether for three times. The aqueous solution was frozen and dried to give the desired asymmetric PFO polymer succinimidyl ester.

Example 28. The Preparation of Asymmetric Cy5 Labeled PFO Polymer Maleimide (Compound 31)

To the solution of Compound 29 (100 mg) in DMF (10 ml) was added 0.1 ml DMF solution of 3-maleimidopropionic acid N-hydroxysuccinimide ester (1 mg, AAT Bioquest) and 10 μl triethylamine. The reaction mixture was stirred at room temperature for 2 hours, and concentrated under high vacuum to remove DMF. The residue was dissolved in water (pH=6), and extracted with ethyl acetate for three times. The aqueous solution was frozen and dried to give the desired asymmetric PFO polymer maleimide.

Example 29. The preparation of asymmetric Cy5 labeled PFO polymer dichlorotriazine (Compound 31)

To the solution of Compound 29 (100 mg) in DMF (10 ml) was added 0.1 ml DMF solution of cyanuric chloride (1 mg, Sigma) and 10 μl triethylamine. The reaction mixture was stirred at room temperature for 3 hours, and concentrated under high vacuum to remove DMF. The residue was washed with ethyl acetate for multiple times until most of the unreacted cyanuric chloride was removed. The residue was quickly dissolved in cold water (pH=6), and extracted with ethyl acetate for three times. The aqueous solution was frozen and dried to give the desired asymmetric PFO polymer dichlorotriazine.

Example 30. The Preparation of Asymmetric Cy5 Labeled PFO Polymer DBCO (Compound 32)

To the solution of Compound 29 (100 mg) in DMF (10 ml) was added 0.1 ml DMF solution of DBCO-PEG4 succinimidyl ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted DBCO-PEG4 succinimidyl ester was removed. The residue was dissolved in water, and extracted with ethyl acetate for three times. The aqueous solution was frozen and dried to give the desired asymmetric PFO polymer DBCO.

Example 31. The Preparation of Asymmetric Cy5 Labeled PFO Polymer TCO (Compound 33)

To the solution of Compound 29 (100 mg) in DMF (10 ml) was added 0.1 ml DMF solution of TCO-PEG4 succinimidyl ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted TCO-PEG4 succinimidyl ester was removed. The residue was dissolved in water, and extracted with ethyl acetate for three times. The aqueous solution was frozen and dried to give the desired asymmetric PFO polymer TCO.

Example 32. The Preparation of Asymmetric Cy5 Labeled PFO Polymer Methyltetrazine (Compound 34)

To the solution of Compound 29 (100 mg) in DMF (10 ml) was added 0.1 ml DMF solution of methyltetrazine-PEG4 succinimidyl ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted methyltetrazine-PEG4 succinimidyl ester was removed. The residue was dissolved in water, and extracted with ethyl acetate for three times. The aqueous solution was frozen and dried to give the desired asymmetric PFO polymer methyltetrazine.

Example 33. The Preparation of Asymmetric Cy5 Labeled PFO Polymer Azide (Compound 35)

To the solution of Compound 29 (100 mg) in DMF (10 ml) was added 0.1 ml DMF solution of azido-PEG4 succinimidyl ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted azido-PEG4 succinimidyl ester was removed. The residue was dissolved in water, and extracted with ethyl acetate for three times. The aqueous solution was frozen and dried to give the desired asymmetric PFO polymer azide.

Example 34. The Preparation of Asymmetric Cy5 Labeled PFO Polymer Alkyne (Compound 36)

To the solution of Compound 29 (100 mg) in DMF (10 ml) was added 0.1 ml DMF solution of alkynyl-PEG4 succinimidyl ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted alkynyl-PEG4 succinimidyl ester was removed. The residue was dissolved in water, and extracted with ethyl acetate for three times. The aqueous solution was frozen and dried to give the desired asymmetric PFO polymer alkyne.

Example 35. The Preparation of Asymmetric TAMRA Labeled PFO Polymer (Compound 37)

To the solution of Compound 7 (100 mg) in DMF (10 ml) was added 1 ml DMF solution of 5-TAMRA succinimidyl ester (10 mg, AAT Bioquest) and 10 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 36. The Preparation of Asymmetric TAMRA Labeled PFO Polymer DBCO (Compound 38)

To the solution of Compound 37 (100 mg) in DMF (10 ml) was added 0.1 ml DMF solution of DBCO-PEG4 succinimidyl ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted DBCO-PEG4 succinimidyl ester was removed. The residue was dissolved in water, and extracted with ethyl acetate for three times. The aqueous solution was frozen and dried to give the desired asymmetric PFO polymer DBCO.

Example 37. The Preparation of Asymmetric TAMRA Labeled PFO Polymer TCO (Compound 39)

To the solution of Compound 37 (100 mg) in DMF (10 ml) was added 0.1 ml DMF solution of TCO-PEG4 succinimidyl ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted TCO-PEG4 succinimidyl ester was removed. The residue was dissolved in water, and extracted with ethyl acetate for three times. The aqueous solution was frozen and dried to give the desired asymmetric PFO polymer TCO.

Example 38. The Preparation of Asymmetric TAMRA Labeled PFO Polymer Methyltetrazine (Compound 40)

To the solution of Compound 37 (100 mg) in DMF (10 ml) was added 0.1 ml DMF solution of methyltetrazine-PEG4 succinimidyl ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted methyltetrazine-PEG4 succinimidyl ester was removed. The residue was dissolved in water, and extracted with ethyl acetate for three times. The aqueous solution was frozen and dried to give the desired asymmetric PFO polymer methyltetrazine.

Example 39. The Preparation of Asymmetric TAMRA Labeled PFO Polymer Azide (Compound 41)

To the solution of Compound 37 (100 mg) in DMF (10 ml) was added 0.1 ml DMF solution of azido-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted azido-PEG4 succinimidyl ester was removed. The residue was dissolved in water, and extracted with ethyl acetate for three times. The aqueous solution was frozen and dried to give the desired asymmetric PFO polymer azide.

Example 40. The preparation of asymmetric TAMRA labeled PFO polymer alkyne (Compound 42)

To the solution of Compound 37 (100 mg) in DMF (10 ml) was added 0.1 ml DMF solution of alkynyl-PEG4 succinimidyl ester (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted alkynyl-PEG4 succinimidyl ester was removed. The residue was dissolved in water, and extracted with ethyl acetate for three times. The aqueous solution was frozen and dried to give the desired asymmetric PFO polymer alkyne.

Example 41. The Preparation of Asymmetric TAMRA Labeled PFO Polymer Succinimidyl Ester (Compound 43)

To the solution of Compound 37 (100 mg) in DMF (10 ml) was added 0.1 ml DMF solution of di(N-succinimidyl) glutarate (1 mg, AAT Bioquest) and 10 µl triethylamine. The reaction mixture was stirred at room temperature for 2 hours, and concentrated under high vacuum to remove DMF. The residue was washed with ether for multiple times until most of the unreacted di(N-succinimidyl) glutarate was removed. The residue was quickly dissolved in cold water (pH=6), and extracted with ether for three times. The aqueous solution was frozen and dried to give the desired asymmetric PFO polymer succinimidyl ester.

Example 42. The Preparation of Asymmetric TAMRA Labeled PFO Polymer Maleimide (Compound 44)

To the solution of Compound 37 (100 mg) in DMF (10 ml) was added 0.1 ml DMF solution of 3-maleimidopropionic acid N-hydroxysuccinimide ester (1 mg, AAT Bioquest) and 10 µl triethylamine. The reaction mixture was stirred at room temperature for 2 hours, and concentrated under high vacuum to remove DMF. The residue was dissolved in water (pH=6), and extracted with ethyl acetate for three times. The aqueous solution was frozen and dried to give the desired asymmetric PFO polymer maleimide.

Example 43. The Preparation of Asymmetric TAMRA Labeled PFO Polymer Dichlorotriazine (Compound 45)

To the solution of Compound 37 (100 mg) in DMF (10 ml) was added 0.1 ml DMF solution of cyanuric chloride (1 mg, AAT Bioquest) and 10 µl triethylamine. The reaction mixture was stirred at room temperature for 3 hours, and concentrated under high vacuum to remove DMF. The residue was washed with ethyl acetate for multiple times until most of the unreacted cyanuric chloride was removed. The residue was quickly dissolved in cold water (pH=6), and extracted with ethyl acetate for three times. The aqueous solution was frozen and dried to give the desired asymmetric PFO polymer dichlorotriazine.

Example 44. The Preparation of Asymmetric Texas Red Labeled PFO Polymer DBCO (Compound 46)

To the solution of Compound 7 (100 mg) in DMF (10 ml) was added 0.1 ml DMF solution of 2-(Texas Red)sulfonamidyl-6-(TCO-PEG4)carboxamidyl-lysine monosuccinimidyl ester (1 mg, AAT Bioquest) and 10 µl triethylamine. The reaction mixture was stirred at room temperature for 3 hours, and concentrated under high vacuum to remove DMF. The residue was dissolved in water, dialyzed into 20% EtOH/H$_2$O using a tangential flow filtration system with 30,000 kD molecular weight cutoff membrane until there was less than 0.1 mg/mL of polymer in the elutant. The solution was concentrated and lyophilized to give the desired blue fibrous solid.

Example 45. The Preparation of Asymmetric Texas Red Labeled PFO Polymer TCO (Compound 47)

To the solution of Compound 7 (100 mg) in DMF (10 ml) was added 0.1 ml DMF solution of 2-(Texas Red) sulfonamidyl-6-(TCO-PEG4)carboxamidyl-lysine monosuccinimidyl ester (1 mg, AAT Bioquest) and 10 µl triethylamine. The reaction mixture was stirred at room temperature for 3 hours, and concentrated under high vacuum to remove DMF. The residue was dissolved in water, dialyzed into 20% EtOH/H$_2$O using a tangential flow filtration system with 30,000 kD molecular weight cutoff membrane until there was less than 0.1 mg/mL of polymer in the elutant. The solution was concentrated and lyophilized to give the desired blue fibrous solid.

Example 46. The Preparation of Texas Red-Labeled PFO Polymer Methyltetrazine (Compound 48)

To the solution of Compound 7 (100 mg) in DMF (10 ml) was added 0.1 ml DMF solution of 2-(Texas Red) sulfonamidyl-6-(methyltetrazine-PEG4) carboxamide-lysine monosuccinimidyl ester (1 mg, AAT Bioquest) and 10 µl triethylamine. The reaction mixture was stirred at room temperature for 3 hours, and concentrated under high vacuum to remove DMF. The residue was dissolved in water, dialyzed into 20% EtOH/H$_2$O using a tangential flow filtration system with 30,000 kD molecular weight cutoff membrane until there was less than 0.1 mg/mL of polymer in the elutant. The solution was concentrated and lyophilized to give the desired blue fibrous solid.

Example 47. The Preparation of Asymmetric Texas Red Labeled PFO Polymer Azide (Compound 49)

To the solution of Compound 7 (100 mg) in DMF (10 ml) was added 0.1 ml DMF solution of 2-(Texas Red) sulfonamidyl-6-(azido-PEG4)carboxamidyl-lysine monosuccinimidyl ester (1 mg, AAT Bioquest) and 10 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 48. The Preparation of Asymmetric TCO-Functionalized PFO Polymer (Compound 50)

To the solution of Compound 7 (100 mg) in DMF (10 ml) was added 0.1 ml DMF solution of TCO-PEG4 succinimidyl ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted TCO-PEG4 succinimidyl ester was removed. The residue was dissolved in water, and extracted with ethyl acetate for three times. The aqueous solution was frozen and dried to give the desired asymmetric TCO-functionalized PFO polymer.

Example 49. The Preparation of Asymmetric ROX Labeled PFO Polymer TCO (Compound 51)

To the solution of Compound 50 (10 mg) in DMF (10 ml) was added 0.1 ml DMF solution of 6-ROX succinimidyl ester (1 mg, AAT Bioquest) and 10 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 50. The Preparation of Asymmetric Maleimide-Functionalized PFO Polymer (Compound 52)

To the solution of Compound 7 (100 mg) in DMF (10 ml) was added 0.1 ml DMF solution of 3-maleimidopropionic acid N-hydroxysuccinimide ester (1 mg, AAT Bioquest) and 10 μl triethylamine. The reaction mixture was stirred at room temperature for 3 hours, and concentrated under high vacuum to remove DMF. The residue was washed with ethyl acetate for multiple times until most of the unreacted 3-maleimidopropionic acid N-hydroxysuccinimide ester is removed. The residue was dissolved in water, and extracted with ethyl acetate for three times. The aqueous solution was frozen and dried to give the desired asymmetric maleimide-functionalized PFO polymer.

Example 51. The Preparation of Asymmetric ROX Labeled PFO Polymer Malemide (Compound 53)

To the solution of Compound 52 (10 mg) in DMF (10 ml) was added 0.1 ml DMF solution of 6-ROX succinimidyl ester (1 mg, AAT Bioquest) and 10 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

Example 52. The Preparation of Asymmetric Cy7 Labeled PFO Polymer Maleimide (Compound 54)

To the solution of Compound 7 (100 mg) in DMF (10 ml) was added 1 ml DMF solution of Cy7 monomalemide, monosuccinimidyl ester (5 mg, AAT Bioquest) and 10 μl triethylamine. The reaction mixture was stirred at room temperature for 3 hours, and concentrated under high vacuum to remove DMF. The residue was dissolved in water, dialyzed into 20% EtOH/$H_2O$ using a tangential flow filtration system with 30,000 kD molecular weight cutoff membrane until there was less than 0.1 mg/mL of polymer in the elutant. The solution was concentrated and lyophilized to give the desired blue fibrous solid.

The above examples of some synthetic strategies for the selected polymers of the invention, as well as their characterization, synthetic precursors, conjugates and methods of use are provided in the examples for illustration. Their further modifications and permutations are obvious to one skilled in the art. For example, the second fluorophores (such as Cy3.5, Cy5, TAMRA and Texas Red in the above examples) conjugated to the polymers of the invention can be readily replaced with the commercial dyes listed in Table 1 to make the polymers have the different desired spectral properties. In addition, the polymers of the invention can be further functionalized with a different reactive functional group pairs as listed in Table 2. The well-known clickable groups can also be added to the polymers of the invention for the biorthogonal chemistry-based conjugations (see P. Agarwal and R. Bertozzi, Bioconjugate Chem., 2015, 26, 176-192; K. Lang and J. Chin, Chem. Reviews, 2014, 114, 4764-4806; M. D. Best, Biochemistry, 2009, 48, 6571-6584). Some other alternative methods for polymer functionalization were well described in the literature (see U.S. Pat. No. 8,158,444; U.S. Pat. No. 8,455,613; U.S. Pat. No. 8,354,239; U.S. Pat. No. 8,362,193; and U.S. Pat. No. 8,575,303 to Gaylord, et al.; also WO 2013/101902 to Chiu et al).

Example 53. Preparation of Phalloidin-PFO Polymer Conjugate (Compound 55)

To aminophalloidin (1 mg, AAT Bioquest) and the succinimidyl ester derivative Compound 8 (10 mg) in DMF (0.5 mL) was added N,N-diisopropylethylamine (25 μL). The mixture was stirred at room temperature for 3 hours. To this solution was added 5 mL of EtOAc. The solid was collected by centrifugation. The crude product was purified on SEP-HADEX LH-20, eluting with water, followed by preparative HPLC to give the pure phalloidin conjugate.

Figure 4:
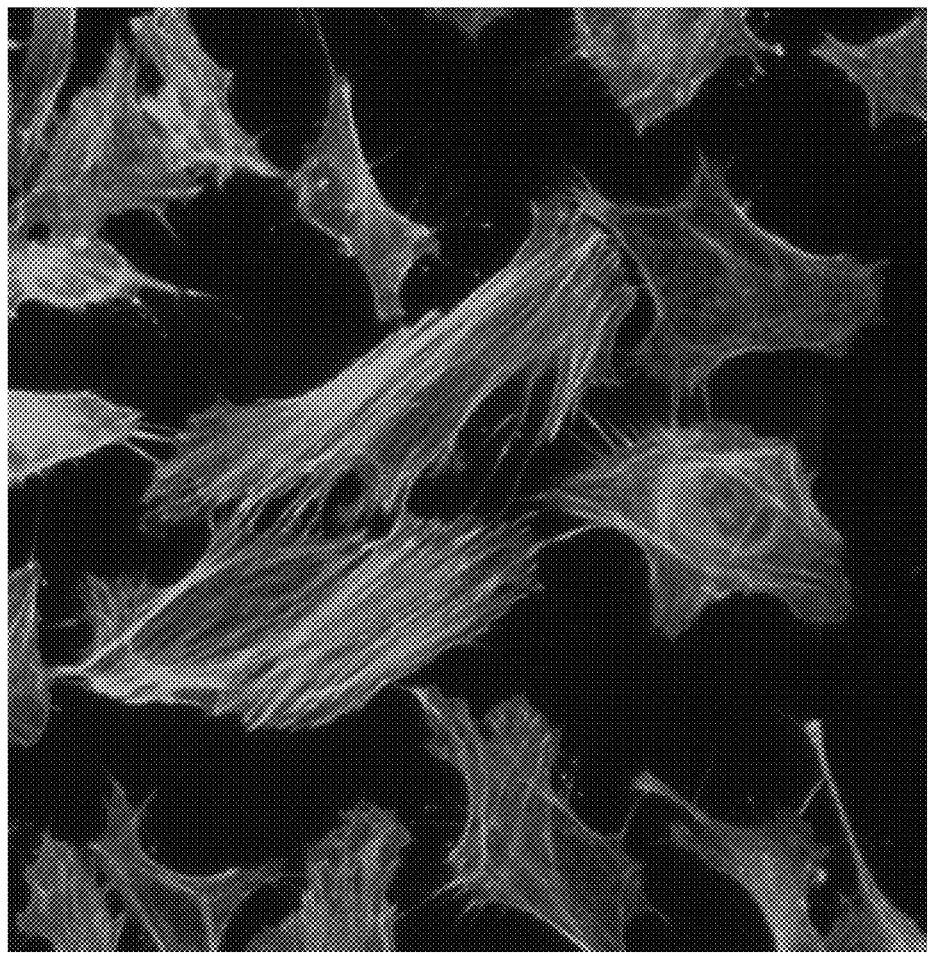
FIG. 4. The cellular F-actin staining with the conjugate of phalloidin and polyfluoreno[4,5-cde]oxepine (See Example 53). Hela cells were fixed with 3-4% formaldehyde in PBS at room temperature for 10-30 minutes. The fixed cells were washed with PBS buffer 3 times. 0.1% Triton was added to the fixed cells to increase conjugate permeability for 10 minutes. The cells were rinsed for 3 times with PBS. 5 µl of PFO-phalloidin conjugate solution (10 µg/ml) was added into the fixed cells (100 µL/well, 96-well plate). The cells were incubated at room temperature for 20 to 90 minutes, and rinsed gently with PBS 3 times to remove excess phalloidin conjugate before imaging under a fluorescence microscope.
Figure 5:
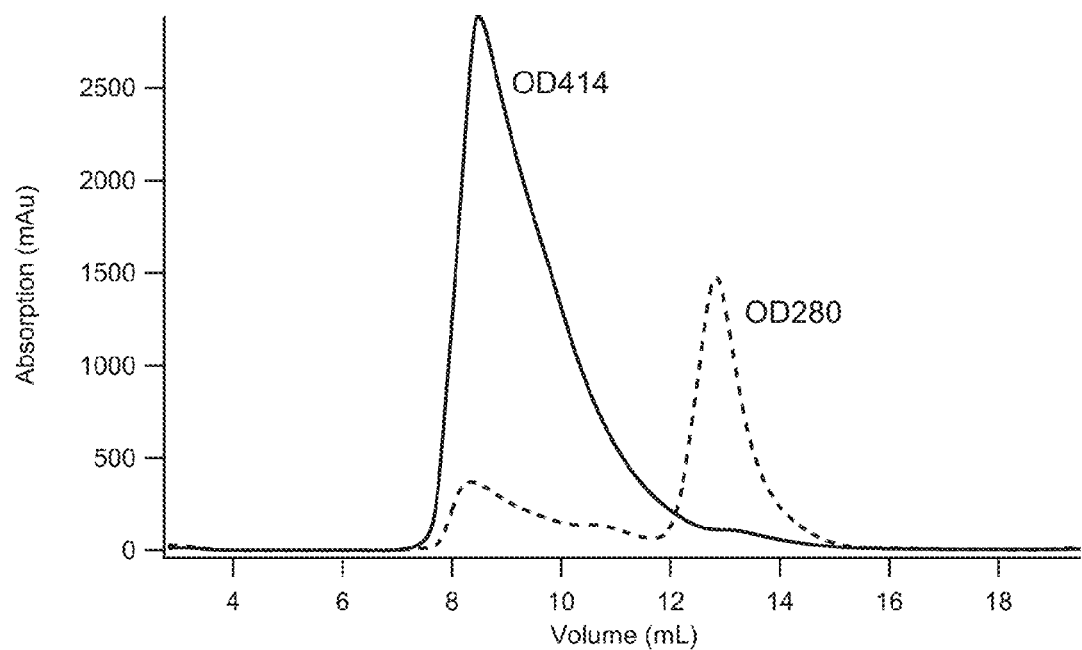
FIG. 5. Superdex 200 SEC purification of Cy3.5-PFO tandem-mCD8a antibody conjugate (See Examples 64 and 65). The first elution peak was collected as the purified product, the large OD280 peak around 13 mL is the free-antibody.
Figure 6:
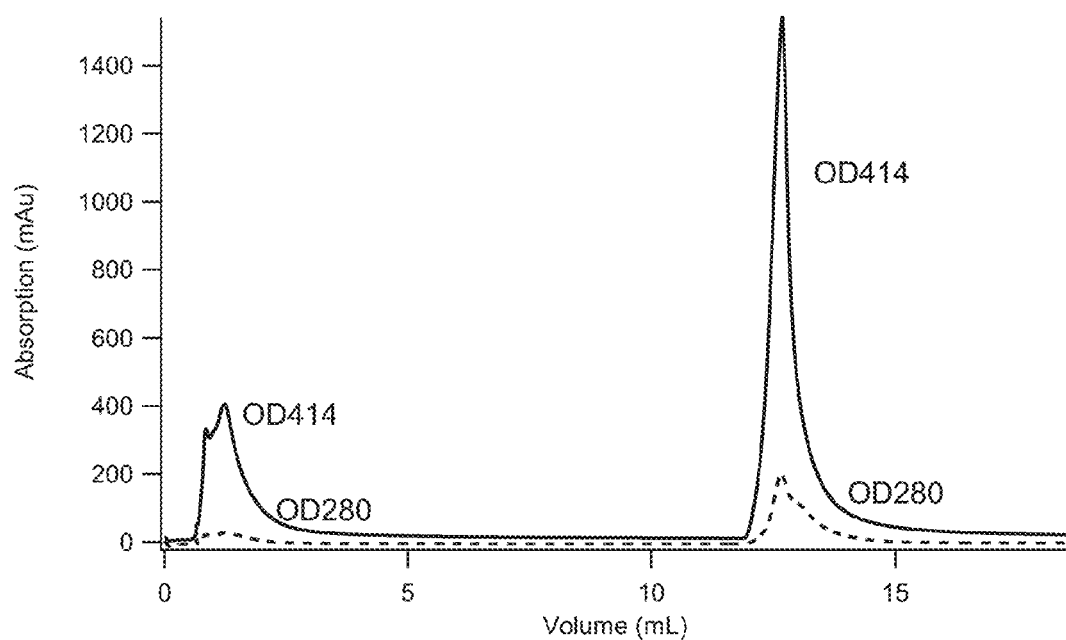
FIG. 6. The further protein G affinity purification of Cy3.5-PFO tandem-mCD8a antibody conjugate after S200 SEC purification (See Example 64). The free-polymer, i.e. not conjugated with the mCD8a antibody, was eluted in the first couple of column volumes, and the conjugate was eluted at low pH conditions starting around 12 mL.

Example 54. The Staining of F-Actin Filaments with Phalloidin-PFO Polymer Conjugates Actin is a globular, roughly 42-kDa protein found in almost all eukaryotic cells. It is also one of the most highly conserved proteins, differing by no more than 20% in species as diverse as algae and humans. Phalloidin-PFO polymer conjugate selectively binds to F-actins. Used at nanomolar concentrations, phalloidin-PFO polymer conjugate (Compound 55) can be used for labeling, identifying and quantitating F-actins in formaldehyde-fixed and permeabilized tissue sections, cell cultures or cell-free experiments. Cells were fixed with formaldehyde and incubated after the addition of DMSO stock solution of phalloidin-PFO polymer conjugate. The cells were gently rinsed with PBS for 2 to 3 times to remove excess phalloidin conjugate. The cells were plated, sealed and imaged with a fluorescence microscope (See FIG. 4). Other phalloidin-PFO polymer conjugates can be analogously used to stain of F-actin filaments with different fluorescence colors.

Example 55. Preparation of Aminodextran-PFO Polymer Conjugates

Aminodextran-dye conjugates were prepared as follows, described using 70,000 MW as an example. Aminodextran (50 mg) derivatized with an average of 13 amino groups. The aminodextran (50 mg) was dissolved at 10 mg/mL in 0.1 M NaHCO3. Compound 8 was added so as to give a PFO polymer/dextran ratio of about 10-15. After 6-12 hours, the resulting conjugate was purified by ion exchange chromatography. The conjugation mixture was loaded to UNO-sphere™ S resin (Bio-Rad) in low salt buffer [50 mM MES Buffer (pH=5.0)], and incubated at room temperature for 10 minutes, repeatedly loading the sample for 3 times to get the maximum binding. After loading, the medium was washed with low salt buffer, and run with a gradient of elevating pH and ionic strength [10 mM phosphate buffer (pH=7.4)+1.0 M NaCl buffer/methanol].

Example 56. Preparation of PFO Polymer-Labeled Microspheres

Microspheres can be labeled with a PFO polymer dye of the present invention using any of a number of well-known protocols. Microspheres chemically modified to have functional groups such as amino, carboxyl, or aldehydes on the surface can be surface-labeled by covalently conjugating the surface groups with a corresponding reactive dye, as listed in Table 2. For example, amine-modified microspheres were readily conjugated to the dyes of the invention through succinimidyl esters, such as Compound 8 or 22.

Example 57. Preparation of Nucleotide-PFO Polymer Conjugates

Nucleotides conjugated with the PFO polymer dyes of invention can be readily prepared by someone skilled in the art following the well-known, published procedures, such as those described in M. Nimmakayalu et al., Biotechniques 2000, 28, 518-522; Muhlegger et al., Biol Chem Hoppe Seyler 1990, 371, 953-965; and Giaid et al., Histochemistry 1989, 93, 191-196. To 2 mg of 5-(3-aminoallyl)-2'-deoxyuridine 5'-triphosphate (Sigma-Aldrich) in 100 µL water was added Compound 8 or 22 (5 mg) in 100 µL DMF and 5 µL triethylamine. After 3 hours, the solution was evaporated and the residue is purified by HPLC. The product fractions were lyophilized to give fluorescent nucleotide conjugate. Alternatively, fluorescent dye-conjugates of deoxyuridine 5'-triphosphate were prepared from 5-(3-amino-1-propynyl)-2'-deoxyuridine 5'-triphosphate, or by treating a thiolated nucleotide or a thiophosphate nucleotide with a thiol-reactive PFO polymer dye of the invention (such as the maleimide Compound 9 or 23).

Example 58. Preparation of Oligonucleotide-PFO Polymer Dye Conjugates

A 5'-amine-modified, 18-base M13 primer sequence (about 100 µg) was dissolved in 4 µl water. To this was added 1 mg of Compound 8 or 22 in 100 µl 0.1 M sodium borate, pH 8.5. After 16 hours, 10 µl of 5 M NaCl and 3 volumes of cold ethanol were added. The mixture was cooled to −20° C., centrifuged, the supernatant was decanted, the pellet was rinsed with ethanol, and the pellet was then dissolved in 100 µL water. The labeled oligonucleotide was purified by HPLC. The desired peak was collected and evaporated to give the fluorescent oligonucleotide-dye conjugate.

Example 59. Preparation of Goat Anti-Mouse IgG-PFO Polymer Dye Conjugates

Goat Anti-Mouse IgG (GAM) was dissolved in 10 mM $NaHCO_3$ (pH 8.2) buffer to make a 5 mg/mL solution. To the aqueous GAM protein solution was added the DMF solution of Compound 8 or 22 (20 equivalents). The solution was rotated at room temperature for 3 hours and the reaction mixture was transferred to an Amicon Ultra filter (MWCO=10 kDa) to remove DMF. The protein was recovered into the initial volume with PBS buffer.

Cation exchange chromatography was used to remove free polymer. Conjugation mixture was loaded to UNO-sphere™ S resin (Bio-Rad) in low salt buffer [50 mM MES Buffer (pH=5.0)], and incubated at room temperature for 10 minutes, repeatedly loading the sample for 3 times to get the maximum binding. After loading, the medium was washed with low salt buffer to the baseline (until the absorbance at 414 nm is lower than 0.01) to remove all free polymer. The retained PFO polymer dye-GAM conjugate on the cation exchange resin was released by elevating both the pH and ionic strength with high salt phosphate buffer [10 mM phosphate buffer (pH=7.4)+1.0M NaCl buffer/methanol, 90/10]. Protein A and Protein G affinity resins can also be used to remove free polymer with comparable results. A HiTrap Protein G HP 1 mL column (GE Lifesciences) was pre-equilibrated with 10 mM Phosphate buffer, pH 7.4, and the SEC-purified product was slowly injected at <1 mg/mL and allowed to incubate for 30 minutes to bind. The column was washed with >10 column volumes of 10 mM Phosphate buffer to wash unbound polymer material off while monitoring absorption of the eluate at 280 nm and 414 nm to ensure all excess material was removed. The conjugate was eluted by washing the column with 4 column volumes of 0.1 M Glycine pH 2.3. The eluted fractions were combined and pH-adjusted back to neutral using 1 M Tris pH 8. After free polymer was removed, the conjugate solution was concentrated with Amicon Ultra Filter (MWCO=30 kD) and loaded to a size exclusion column (Superdex 200, GE life sciences) to separate conjugate and unconjugated antibody. The column was equilibrated with PBS buffer, and the PFO polymer-antibody conjugate was eluted before free antibodies.

For effective labeling, the degree of substitution (DOS) should fall between 1-3 moles of PFO polymer dye to one mole of antibody for most antibodies. The ratio of biological substrate to polymer (BS/polymer) represents the degree of substitution by a biological substrate. For example, when using the polymer to label a biological substrate, there might be unlabeled free polymer. Thus the average degree of substitution might be less than 1. As is well known in the art, the optima DOS depends on the properties of antibody to be labeled. The optimal labeling DOS is determined empirically by preparing a series of dye-conjugates over a range of DOS and comparing the desired signal/background. In some cases, a higher DOS may provide bright signal while in other cases higher DOS could reduce the affinity of the antibody to be labeled.

Example 60. Preparation of Goat Anti-Rabbit IgG-PFO Polymer Dye Conjugate

Goat Anti-Rabbit IgG (GAR) was dissolved in 1 M NaHCO$_3$ (pH=8.6) to make the concentration of 10 mg/ml. To the GAR solution was added methyltetrazine-PEG4-Sulfo-NHS Ester (10 mg/ml DMSO solution, 3 equivalents). The mixture was rotated at room temperature on a tube rotator for 1~2 hours, and purified with a desalting column filled with P-6-DG Gel medium (Bio-Rad) to remove the free methyltetrazine-PEG4-Sulfo-NHS Ester. The methyltetrazine-modified GAR was recovered into PBS. The modified GAR solution was mixed with the PBS stock solution of Compound 13 (4 mg/ml, 5 equivalents). The mixed solution was rotated at room temperature for 1 to 3 hours. The resulted solution was loaded to a cation exchange column used to remove the unreactive free polymer. The PFO polymer-GAR solution was purified as described in Example 59. The pure desired PFO polymer-GAR conjugate were pooled, combined, and concentrated with Amicon Ultra Filter (MWCO=30 kD) to a desired concentration.

Example 61. Preparation of Sheep Anti-Mouse IgG-PFO Polymer Dye Conjugate

Sheep Anti-Mouse IgG (SAM) was reduced with MEA, DTT or TCEP (G. T. Hermanson, Bioconjugate Techniques, 1996, 463-469). The reduced GAM was dissolved in 50 mM MES Buffer (pH=6.0) to make a 5 mg/mL solution. To the aqueous SAM protein solution was added the DMF solution of Compound 9 or 23 (10 equivalents). The solution was rotated at room temperature for 3 hours and the reaction mixture was transferred to an Amicon Ultra filter (MWCO=10 kDa) to remove DMF. The protein was recovered into the initial volume with PBS buffer. The PFO polymer-SAM solution was purified as described in Example 59. The pure desired PFO polymer-SAM conjugate were pooled, combined, and concentrated with Amicon Ultra Filter (MWCO=30 kD) to a desired test concentration.

Example 62. Preparation of Goat Anti-Human IgG-PFO Polymer Dye Conjugate

Goat Anti-Rabbit IgG (GAH) was dissolved in 1 M NaHCO$_3$ (pH=8.6) to make the concentration of 10 mg/ml. To the GAH solution was added azido-PEG4-Sulfo-NHS Ester (10 mg/ml DMSO solution, 3 equivalents). The mixture was rotated at room temperature on a tube rotator for 1~2 hours, and purified with a desalting column filled with P-6-DG Gel medium (Bio-Rad) to remove the free azido-PEG4-Sulfo-NHS Ester. The azido-modified GAH was recovered into PBS. The modified GAH solution was mixed with the PBS stock solution of Compound 11 (4 mg/ml, 5 equivalents). The mixed solution was rotated at room temperature for 1 to 3 hours. The resulted solution was loaded to a cation exchange column used to remove the unreactive free polymer. The PFO polymer-GAH solution was purified as described in Example 59. The pure desired PFO polymer-GAH conjugate were pooled, combined, and concentrated with Amicon Ultra Filter (MWCO=30 kD) to a desired concentration.

Example 63. Preparation of Donkey Anti-Mouse IgG-PFO Polymer Dye Conjugate

Donkey Anti-Mouse IgG (DAM) was dissolved in 1 M NaHCO$_3$ (pH=8.6) to make the concentration of 10 mg/ml. To the DAM solution was added azido-PEG4-Sulfo-NHS Ester (10 mg/ml DMSO solution, 3 equivalents). The mixture was rotated at room temperature on a tube rotator for 1~2 hours, and purified with a desalting column filled with P-6-DG Gel medium (Bio-Rad) to remove the free azido-PEG4-Sulfo-NHS Ester. The azido-modified DAM was recovered into PBS. The modified DAM solution was mixed with the PBS stock solution of Compound 17 (4 mg/ml, 5 equivalents). The mixed solution was rotated at room temperature for 1 to 3 hours. The resulted solution was loaded to a cation exchange column used to remove the unreactive free polymer. The PFO polymer-DAM solution was purified as described in Example 59. The pure desired PFO polymer-DAM conjugate were pooled, combined, and concentrated with Amicon Ultra Filter (MWCO=30 kD) to a desired concentration.

Example 64. Preparation of PFO Polymer Dye-Conjugates of Anti-CD8 Antibodies PFO polymer dye-CD antibody conjugates were prepared using antibodies specific to anti-mouse CD8a (clone 53-6.7, eBioscience) and anti-human CD8a (clone SK1, eBioscience), each conjugated, in separate preparations, to Compounds 8, 9, 11 and 12 over a range of dye-to-protein ratios analogously as described in examples 59-63. The antibody-polymer conjugates were purified from the free antibodies over Superdex200 Size Exclusion Chromatography (SEC) using a Bio-Rad NGC FPLC chromatography system. The conjugates were first spun at 15 k rpm for 5 minutes to pellet any precipitated or cross-linked conjugate. The supernatants were then injected onto a Superdex 200 10/300 GL column (GE Lifesciences) at <1.5% v/v and eluted at 1.0 mL/min with 10 mM phosphate buffer (pH 7.4). For each PFO polymer-antibody conjugation, the first elution peak at 280 nm was collected, which contained the antibody-polymer conjugate and any free polymer and any subsequent peaks were discarded.

If excess polymer needed to be removed from the conjugate solution, protein G affinity purification was used to separate the conjugate from free-polymer. A HiTrap Protein G HP 1 mL column (GE Lifesciences) was pre-equilibrated with 10 mM phosphate buffer (pH 7.4), and the SEC-purified product was slowly injected at <1 mg/mL and allowed to incubate for 10 minutes to bind. The column was washed with >10 column volumes of 10 mM phosphate buffer to wash unbound polymer material off while monitoring absorption of the eluate at 280 nm and 414 nm to ensure all excess material had been removed. The conjugate was eluted by washing the column with 4 column volumes of 0.1 M Glycine pH 2.3. The eluted fractions were combined and pH-adjusted back to neutral using 1 M Tris (pH 8). The final purified product was then buffer exchanged 4× in Amicon Ultra-4 30 k molecular weight centrifugal concentrators with 10 mM phosphate, 0.5 M NaCl, 0.09% sodium azide (pH 7.4) and stored at 0.1 mg/mL antibody concentration at 4° C. until ready for use. For each antibody, the optimal PFO polymer dye-to-protein ratios for each of the three dyes were quite similar. In general, each the optimal dye-to-protein ratio was determined empirically (by routine optimization) for each specific antibody to be labeled.

Example 65. Preparation of PFO Polymer Tandem Dye-Conjugates of Anti-CD8 Antibodies PFO polymer dye-CD antibody conjugates were prepared using antibodies specific to anti-mouse CD8a (clone 53-6.7, eBioscience) and anti-human CD8a (clone SK1, eBioscience), each conjugated, in separate preparations, to Compounds 17, 18, 22, 23, 25, 32, 36 and 38 over a range of dye-to-protein ratios as described in examples 59-63. The antibody-polymer conjugates were purified as described in Example 64.

Example 66. Preparation of Streptavidin-PFO Polymer Conjugate

Streptavidin was dissolved in 10 mM $NaHCO_3$ buffer (pH 8.2) to make a 1 mg/mL solution. To the aqueous streptavidin protein solution was added the DMF solution of Compound 8 or 22 (20 eq). The solution was shaken at room temperature for 3 hours and the reaction transferred to an Amicon Ultra filter (MWCO=10 kDa) to remove DMF. The protein was recovered into the initial volume with PBS buffer. Cation exchange chromatography was used to remove free polymer. Conjugation mixture was loaded to UNOsphere™ S resin (Bio-Rad) in low salt buffer [50 mM MES Buffer (pH=5.0)], and incubated at room temperature for 10 minutes, repeatedly loading the sample for 3 times to get the maximum binding. After loading, the medium was washed with low salt buffer to the baseline (until the absorbance at 414 nm is lower than 0.01) to remove all free polymer. The retained PFO polymer dye-streptavidin conjugate on the cation exchange resin was released by elevating both the pH and ionic strength with high salt phosphate buffer [10 mM phosphate buffer (pH=7.4)+1.0M NaCl buffer/methanol, 90/10]. The eluted fractions were combined and concentrated to desired concentration.

Example 67. PFO Polymer Conjugates for Use in Flow Cytometry

Analyte-specific antibodies conjugated to a PFO polymer dye of the present invention (i.e, labeled antibodies) are useful for the analysis of blood cells (for example, in whole blood samples) by flow cytometry. The labeled-antibodies were used to stain cellular proteins, and the labeled cells were detected using a flow cytometer. PFO Polymer bioconjugates were evaluated by Stain Index, as defined by BD Biosciences on a flow cytometer. See, e.g., H. Maeker and J. Trotter, BD Biosciences Application Note: "Selecting Reagents for Multicolour Flow Cytometry", September 2009. The stain index reports a measure of the polymer's brightness, nonspecific binding. Flow cytometry provides a method through which to measure cells of a specific phenotype or analytes of interest on specific microspheres. This can be done with direct labeling of a primary antibody or, if signal amplification is desired, through a secondary antibody or the avidin-biotin complexation with avidin-polymer conjugates. Cells of interest were taken up in sufficient quantity, spun down, washed in DPBS+0.2% BSA and 0.05% $NaN_3$, then resuspended in staining buffer of PFO polymer conjugates.

For primary incubation, cells were incubated with a primary conjugate (e.g., PFO polymer-CD8 antibodies in Examples 64 and 65) specific to an antigen of interest, negative cells served as a negative non-specific binding reference. A control population or an established commercial conjugate was used as a positive control. Primary antibody-polymer conjugates were incubated at concentrations with volume dilutions from 10-500 nM for 30 minutes.

For secondary antibody labeling, an unlabeled primary antibody to the antigen of interest was incubated at 1-50 μg/ml, or other titrated amount. Following primary incubation, cells were rinsed with 5 volumes staining buffer and spun down for 3-5 minutes. Species reactive secondary PFO polymer conjugates (e.g., Examples 59-63) were incubated at concentrations with volume dilutions from 10-500 nM for 30-60 minutes. Following secondary incubation, cells were rinsed with 3-5 volumes staining buffer and spun down for 3-5 minutes. Cells were resuspended for testing in DPBS+ 0.2% BSA, 0.05% sodium azide.

For streptavidin-polymer conjugate labeling, cells were incubated with a biotinylated primary antibody to the marker of interest, as detailed above for the secondary antibody labeling, instead of an unlabeled primary. Following the primary washing, cells were resuspended and incubated with streptavidin-polymer conjugates (Example 66) at 1-100 nM volume dilutions for 30 minutes. Following secondary incubation, cells were rinsed with 5 volumes staining buffer and spun down for 3-5 minutes. Cells were resuspended for testing. If further signal amplification was desired, cells could be incubated with an unlabeled primary antibody and then subsequently followed with a species reactive biotinylated secondary antibody prior to incubation with streptavidin conjugates.

Example 68. PFO Polymer-AntiCD8 Conjugates for Analyzing Blood Samples

The cell staining was prepared essentially as described in example 67. The PFO polymer-CD8 antibody conjugates were used to analyze lymphocytes in whole blood samples. Samples (100 μL) of whole blood (preferably collected in EDTA) typically were stained with antibody-PFO polymer dye conjugates for 30-60 minutes in the dark at a dye-conjugate concentration of 1-20 μg/ml of blood. Following staining, proper amount of cell lysing solution was added to the cell sample. The treated sample was mixed at medium speed on vortex mixer and then incubated at room temperature for 10 min. The sample was centrifuged at 200-500 g for 5 minutes and the supernatant is decanted. The sample was washed (resuspended in 2 mL of 0.5% BSA/PBS wash buffer, mixed, and centrifuged) twice, re-suspended in wash buffer, and held at 4° C. until flow cytometric analysis.

Figure 7:
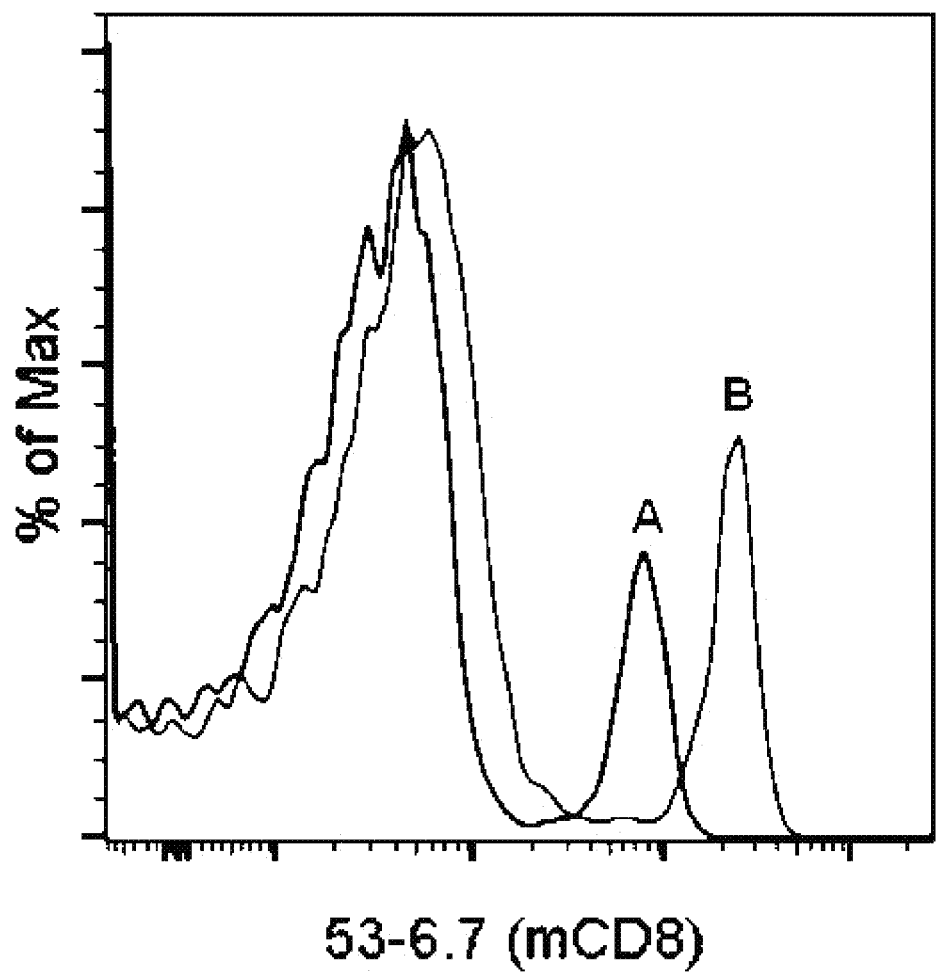
FIG. 7. Staining of mouse splenocytes with Anti-Mouse CD8a (clone 53-6.7) antibody conjugated to PFO and analyzed by flow cytometry. Single cell suspensions were stained with Cy3.5-PFO tandem conjugated to rat anti-mouse CD8a (clone 53-6.7) antibody or with BD Horizon™ BV605 Rat Anti-Mouse CD8 (clone 53-6.7, available from BD Bioscience) respectively under the same conditions. The conjugation of Cy3.5-PFO tandem and rat anti-mouse CD8a was prepared as described in Example 64. The cell suspensions were stained for 30 min at 2-8° C., washed once, and then analyzed by flow cytometry using a 405 nm laser line for excitation and a 605/40 bandpass filter as described in Examples 67 and 68. The Rat Anti-mouse CD8a conjugate of Cy3.5-PFO tandem (FIG. 7: labelled B) demonstrated stronger signal than the polyfluorene-based BD Horizon™ BV605 Rat Anti-Mouse CD8 (FIG. 7: labelled A).
Figure 8:
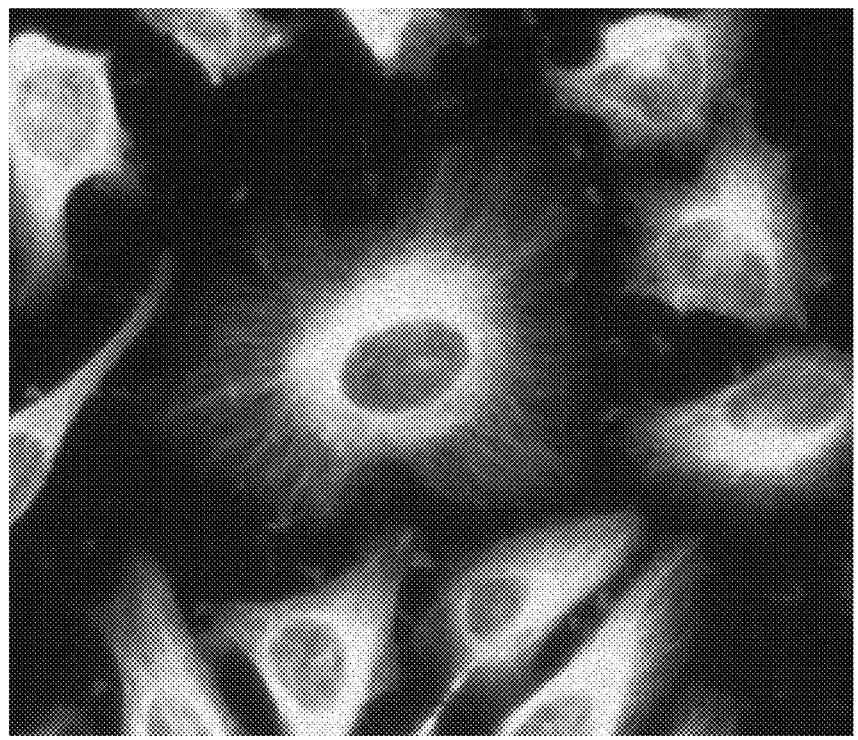
FIG. 8. The fluorescence imaging of tubulin in Hela cells with goat anti-mouse IgG conjugated to polyfluoreno[4,5-cde]oxepine (See Example 59). The Hela cells were fixed with 4% formaldehyde. Mouse anti-tubulin was incubated with the fixed cells. Following the primary incubation, cells were rinsed with 5 volumes of staining buffer and spun down for 3-5 minutes. The cells were then incubated with Goat anti-mouse IgG-PFO polymer conjugates at concentrations within the range 10-500 nM for 30-60 minutes. Following the secondary incubation, cells were rinsed with 3-5 volumes of staining buffer and spun down for 3-5 minutes. The cells were imaged with an Olympus fluorescence microscope.

Analysis of the blood samples was carried out using a flow cytometer. Flow cytometric analysis of the sample of stained cells was carried out according to the manufacturer's protocols, and the data was analyzed using standard techniques well known in the field to obtain the median fluorescence intensity for the cell population of interest. Flow testing was performed using the voltage settings determined from daily calibration of the cytometer with calibration particles by flow facility staff. Lymphocyte specific gating by forward scatter vs. side scatter was performed on unstained cell samples as a background control. Standard doublet gating was performed for both forward scatter and side scatter area vs. width profiles. With only a single color, no compensation was required. Data were collected for all forward and side scatter parameters and fluorescence measurements were made using BD's standard Pacific Blue channel. PFO-antibody conjugate data utilized excitation with the 405 nm Violet lasers and a 605/40 BP filter (See FIG. 7).

It will be understood that the particular antibody conjugate used and the specific reaction components and particular reaction conditions used can have an effect on the results obtained. Routine experimentation should be carried out to determine preferred reaction components, such as buffers or lyse solutions, and reaction conditions, including staining times and temperatures. Such routine optimization of assay conditions is standard practice in the field of immunostaining-based assays.

What is claimed is:

1. A polymer comprising monomers of formula A

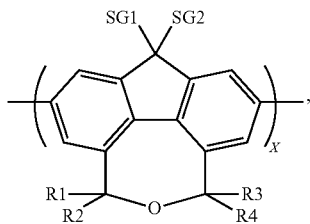

wherein X is the number of monomer A units in the polymer wherein the monomer units are consecutive or nonconsecutive and wherein X is from 6 to 100; and one or more monomers selected from the group consisting of monomer of formula B

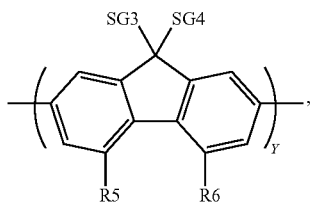

wherein Y is the number of monomer B units in the polymer wherein the monomer units are consecutive or nonconsecutive and wherein Y is from 0 to 99; and monomer of formula C

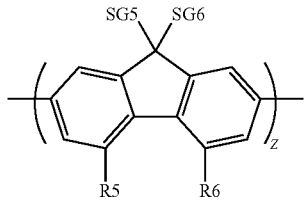

wherein Z is the number of monomer C units in the polymer wherein the monomer units are consecutive or nonconsecutive and wherein Z is from 0 to 99;

wherein R1 to R6 independently is hydrogen, an alkyl, a polyethyleneglycol (PEG), an aryl, a heteroaryl group, or a biological substrate conjugated via a linker (L-BS);

wherein SG1 to SG6 independently is an alkyl, a water soluble group or a L-BS; and wherein the polymer includes end groups HG1 and HG2 wherein HG1 and HG2 independently is a hydrogen, an alkyl, a halogen, a boronyl, an aryl, a heteroaryl group or a L-BS;

wherein the ratio of X to Y+Z is >1, wherein the sum of X+Y+Z is >10.

2. The polymer of claim 1, wherein the polymer comprises an L-BS and the ratio of BS to polymer is 0.2-3.

3. The polymer of claim 1 wherein monomer unit B and monomer unit C are different.

4. The polymer of claim 1, wherein the monomer units are directly connected to one another.

5. The polymer of claim 1, wherein the linker comprises an alkyl, a PEG, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenylphosphonyl-benzoamide, an isoxazole or a succinimide group.

6. The polymer according to claim 1, wherein:
   (i) R1 to R6 independently represent hydrogen, methyl, or ethyl; and/or
   (ii) SG1 to SG6 independently represent a PEG, an alkyl, a carboxyalkyl, a sulfonylalkyl, a phosphonylalkyl, an aminoalkyl or L-BS; and/or
   (iii) L is an alkyl chain or a PEG chain; and/or
   (iv) BS is an antibody, a peptide, a protein, an oligonucleotide, a nucleic acid or a carbohydrate; and/or
   (v) HG1 and HG2 independently represent a hydrogen, an aryl, a halogen or a boronyl; and/or
   (vi) x is an integer from 11-80 and y and z are each an integer independently selected from 0-80, provided that (1) the ratio of BS/polymer is 1-2, (2) the ratio of x/(y+z) is >1, and (3) the sum of x+y+z is >20.

7. The polymer according to claim 1, wherein:
   (i) R1 to R6 are hydrogen; and/or
   (ii) SG1 and SG2 are PEG; and/or
   (iii) SG3 to SG6 independently represent a PEG, an alkyl, a carboxyalkyl, a sulfonylalkyl, a phosphonylalkyl, an aminoalkyl or a L-BS.

8. The polymer according to claim 1, wherein:
   (i) SG3 to SG6 independently represent a PEG, an alkyl, a carboxyalkyl, or a L-BS; or
   (ii) SG3 to SG6 independently represent a PEG, an alkyl, an aminoalkyl or a L-BS.

9. The polymer of claim 8, wherein alkyl is a methyl group.

10. The polymer of claim 1, wherein R1 to R6 are hydrogen; wherein SG1 to SG6 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L comprises an alkyl chain or a PEG chain; wherein BS is an antibody, a peptide, a protein, an oligonucleotide, a nucleic acid or a carbohydrate; and wherein x is an integer from 16-80 and y and z are each an integer independently selected from 0-80, provided that (1) the ratio of BS/polymer is 1-2, (2) the ratio of x/(y+z) is >1, and (3) the sum of x+y+z is >20.

11. The polymer according to claim 1, wherein SG1 and SG2 are independently PEG6 to PEG18.

12. The polymer according to claim 1, wherein the ratio of BS/polymer is 1; x is an integer from 16-80, y and z are each an integer independently selected from 0-64 and wherein the sum of x+y+z is 30-80.

13. The polymer according to claim 1, wherein:
   (i) HG1 and HG2 independently represent a hydrogen, a carboxyaryl, or a L-BS; or
   (ii) HG1 and HG2 independently represent a halogen, a boronyl, a carboxyaryl, or a L-BS.

14. A polymer comprising monomers of formula D

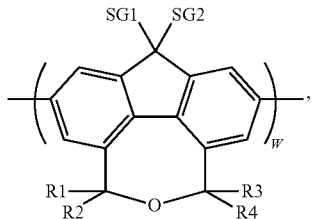

wherein W is the number of monomer D units in the polymer wherein the monomer units are consecutive or nonconsecutive and wherein W is from 6 to 100; and one or more monomers selected from the group consisting of
monomer of formula E

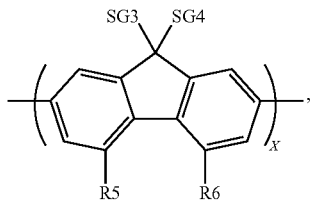

wherein X is the number of monomer E units in the polymer wherein the monomer units are consecutive or nonconsecutive and wherein X is from 0 to 98;
monomer of formula F

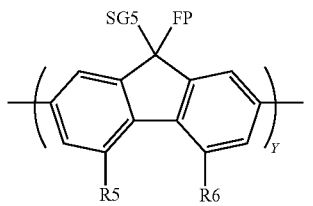

wherein Y is the number of monomer F units in the polymer wherein the monomer units are consecutive or nonconsecutive and wherein Y is from 1 to 20; and
monomer of formula G

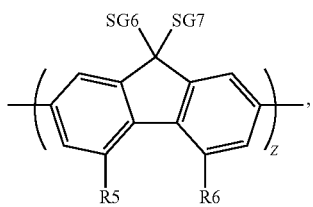

wherein Z is the number of monomer G units in the polymer wherein the monomer units are consecutive or nonconsecutive and wherein Z is from 0 to 98; and
wherein R1 to R6 independently is hydrogen, an alkyl, a polyethyleneglycol (PEG), an aryl, a heteroaryl group, or a biological substrate conjugated via a linker (L-BS);

wherein SG1 to SG7 independently is an alkyl, a water soluble group or a L-BS; and
wherein the polymer includes end groups HG1 and HG2 wherein HG1 and HG2 independently is a hydrogen, an alkyl, a halogen, a boronyl, an aryl, a heteroaryl group or a L-BS;
wherein the ratio of W to X+Y+Z is >1,
wherein the sum of W+X+Y+Z is >10,
wherein FP is a fluorophore or fluorescent dye that has absorption maximum longer than 450 nm and emission maximum longer than 500 nm with fluorescence quantum yield greater than 5%.

15. The polymer of claim 14, wherein the polymer comprises an L-BS and the ratio of BS to polymer is 0.2-3.

16. The polymer of claim 14 wherein monomer unit E and monomer unit G are different.

17. The polymer according to claim 14, wherein the monomer units are directly connected to one another.

18. The polymer according to claim 14, wherein the linker comprises an alkyl, a PEG, an FP, a carboxamide, a thioether, an ester, an imine, a hydrazine, an oxime, an alkyl amine, an ether, an aryl amine, a boronate ester, an N-acylurea or anhydride, a platinum complex, an aminotriazine, a triazinyl ether, an amidine, a urea, a urethane, a thiourea, a phosphite ester, a silyl ether, a sulfonamides, a sulfonate ester, a 1,2,3-triazole, a pyradazine, a thiazolidine, a 2-diphenylphosphonyl-benzoamide, an isoxazole or a succinimide group.

19. The polymer according to claim 14, wherein:
(a) FP is a fluorescein, a rhodamine, a rhodol, a cyanine, a bodipy, a squaraine, a coumarin, a perylenediimide, a diketopyrrolopyrrole, a porphyrin or a phthalocyanine; and/or
(b) R1 to R6 independently represent hydrogen, methyl, or ethyl; and/or
(c) SG1 to SG7 independently represent a PEG, an alkyl, a carboxyalkyl, a sulfonylalkyl, a phosphonylalkyl, an aminoalkyl or a L-BS; and/or
(d) L is an alkyl chain, a FP or a PEG chain; and/or
(e) BS is an antibody, a peptide, a protein, an oligonucleotide, a nucleic acid or a carbohydrate; and/or
(f) HG1 and HG2 independently represent a hydrogen, an aryl, a halogen or a boronyl; and/or
(g) w is an integer from 11-80, x and z are each integers independently selected from 0-80; and wherein y is an integer from 1 to 10, provided that (1) the ratio of BS/polymer is 1-2, (2) the ratio of w/(x+y+z) is >1, and (3) the sum of w+x+y+z is >20.

20. The polymer according claim 14, wherein R1 to R6 are hydrogen.

21. The polymer according to claim 14, wherein the ratio of BS/polymer is 1; w is an integer from 16-79, x and z are each integers independently selected from 0-63 and wherein the sum of w+x+y+z is 30-80.

22. The polymer of claim 14, wherein FP is a fluorescein, a rhodamine, a rhodol, a cyanine, a bodipy, a squaraine, a coumarin, a perylenediimide, a diketopyrrolopyrrole, a porphyrin or a phthalocyanine; wherein R1 to R6 are hydrogen; wherein SG1 to SG7 independently represent a PEG, an alkyl, a carboxyalkyl, a sulfonylalkyl, a phosphonylalkyl, or an aminoalkyl; wherein HG1 and HG2 independently represent a hydrogen, an aryl, a halogen, a boronyl or a L-BS; wherein L comprises an alkyl chain, a FP or a PEG chain; wherein BS is an antibody, a peptide, a protein, an oligonucleotide, a nucleic acid or a carbohydrate; wherein w is an integer from 11-80, x and z are each integers independently selected from 0-80; and wherein y is an integer from 1 to 10, provided that (1) the ratio of BS/polymer is 1-2, (2) the ratio of w/(x+y+z) is >1, and (3) the sum of w+x+y+z is >20.

23. The polymer according to claim 14, wherein FP is a fluorescein, a rhodamine, a cyanine, a bodipy, a squaraine, a perylenediimide, or a phthalocyanine.

24. The polymer of claim 22, wherein:
   (a) FP is a rhodamine; or
   (b) FP is a cyanine.

25. The polymer according to claim 14, wherein the ratio of BS/polymer is 1; and wherein the sum of x+y+z is 30-80.

26. The polymer according to claim 14, wherein:
   (a) HG1 and HG2 independently represent a hydrogen, a carboxyaryl, or a L-BS; and/or
   (b) HG1 and HG2 independently represent a halogen, a boronyl, a carboxyaryl, or a L-BS.

* * * * *